US011807869B2

(12) United States Patent
Mashimo et al.

(10) Patent No.: US 11,807,869 B2
(45) Date of Patent: Nov. 7, 2023

(54) METHOD FOR PRODUCING DNA-EDITED EUKARYOTIC CELL, AND KIT USED IN THE SAME

(71) Applicant: OSAKA UNIVERSITY, Suita (JP)

(72) Inventors: Tomoji Mashimo, Suita (JP); Junji Takeda, Suita (JP); Hiroyuki Morisaka, Suita (JP); Kazuto Yoshimi, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 801 days.

(21) Appl. No.: 16/611,308

(22) PCT Filed: Jun. 8, 2018

(86) PCT No.: PCT/JP2018/022066

§ 371 (c)(1),
(2) Date: Nov. 6, 2019

(87) PCT Pub. No.: WO2018/225858

PCT Pub. Date: Dec. 13, 2018

(65) Prior Publication Data

US 2020/0102580 A1 Apr. 2, 2020

(30) Foreign Application Priority Data

Jun. 8, 2017 (JP) ............................ JP2017-113747

(51) Int. Cl.

| | |
|---|---|
| ***C12N 1/15*** | (2006.01) |
| ***C12N 5/14*** | (2006.01) |
| ***C12N 5/16*** | (2006.01) |
| ***C12N 9/22*** | (2006.01) |
| ***C12N 15/85*** | (2006.01) |
| ***A61K 48/00*** | (2006.01) |
| ***C12N 15/90*** | (2006.01) |

(52) U.S. Cl.

CPC ............ *C12N 15/907* (2013.01); *A61K 48/00* (2013.01); *C12N 5/14* (2013.01); *C12N 5/16* (2013.01); *C12N 9/22* (2013.01); *C12N 15/85* (2013.01); *C12N 15/8509* (2013.01); *C12N 2310/20* (2017.05); *C12N 2800/22* (2013.01); *C12N 2800/80* (2013.01)

(58) Field of Classification Search

CPC ......... C12N 5/14; C12N 5/16; C12N 2310/20

See application file for complete search history.

(56) References Cited

U.S. PATENT DOCUMENTS

| | | | | |
|---|---|---|---|---|
| 2014/0294773 | A1 | 10/2014 | Brouns et al. | |
| 2017/0028083 | A1 | 2/2017 | Beisel et al. | |
| 2018/0334688 | A1* | 11/2018 | Gersbach | C12N 15/52 |
| 2019/0323038 | A1* | 10/2019 | Wiedenheft | C12N 9/22 |

FOREIGN PATENT DOCUMENTS

| | | | |
|---|---|---|---|
| CN | 107557373 | A | 1/2018 |
| CN | 107557378 | A | 1/2018 |
| JP | 2015-503535 | A | 2/2015 |
| JP | 2017-512481 | A | 5/2017 |
| WO | 2014/093595 | A1 | 6/2014 |
| WO | 2016/205613 | A1 | 12/2016 |
| WO | 2017/043573 | A1 | 3/2017 |
| WO | 2017/066497 | A2 | 4/2017 |
| WO | 2017/219033 | A1 | 12/2017 |

OTHER PUBLICATIONS

Huo et al., "Structures of CRISPR Cas3 offer mechanistic insights into Cascade-activated DNA unwinding and degradation", Nat. Struct. Mol. Biol. 21:771-777, 2014 (Year: 2014).*

Hsu et al., Development and Applications of CRISPR-Cas9 for Genome Engineering. Cell (2014), 157: 1262 (Year: 2014).*

Westra et al., CRISPR Immunity Relies on the Consecutive Binding and Degradation of Negatively Supercoiled Invader DNA by Cascade and Cas3, Molecular Cell (2014), 46: 595-605 (Year: 2014).*

Huo et al., Structures of CRISPR Cas3 offer mechanistic insights into Cascade-activated DNA unwinding and degradation. Nature Structural and Molecular Biology (2014), 21(9): 771-777 (Year: 2014).*

Gomaa et al., Programmable Removal of Bacterial Strains by Use of Genome Targeting CRISPR-Cas Systems. MBio (2014), 5(1): e00928-13, 1-9 (Year: 2014).*

Bindal et al., Type I-E CRISPR-Cas System as a Defense System in *Saccharomyces cerevisiae*. MSphere (2022); 7(3): 1-9 (Year: 2022).*

Pyne et al., Harnessing heterologous and endogenous CRISPR-Cas machineries for efficient markerless genome editing in Clostridium Scientific Reports (2016), 6:25666 | DOI: 10.1038/srep25666 (Year: 2016).*

Nelson et al., In vivo genome editing improves muscle function in a mouse model of Duchenne muscular dystrophy. Science (2016), 351: 403-407 and Supplemental material (Year: 2016).*

Morisaka et al., Genome editing in mammalian cells by cascade and Cas3. Journal of Investigative Dermatology (2017), vol. 137; Abstract 490 (Year: 2017).*

Koonin et al., Diversity, classification and evolution of CRISPR-Cas systems. Current Opinion in Microbiology (2017), 37: 67-78 (Year: 2017).*

Makarova et al., Evolutionary classification of CRISPR-Cas systems: a burst of class 2 and derived variants. Nature Reviews Microbiology (2020), 18: 67-83; p. 71, ¶6 (Year: 2020).*

Hochstrasser et al., DNA Targeting by a Minimal CRISPR RNA-Guided Cascade, Mol. Cell (2016), 63: 840-851; Fig 6A (Year: 2016).*

Tan et al., Cas11 enables genome engineering in human cells with compact CRISPR-Cas3 systems. Mol Cell (2022), 82: 852-867 (Year: 2022).*

(Continued)

*Primary Examiner* — Samuel C Woolwine
*Assistant Examiner* — Catherine Konopka
(74) *Attorney, Agent, or Firm* — Sughrue Mion, PLLC

(57) ABSTRACT

A CRISPR-Cas3 system was successfully established in a eukaryotic cell.

5 Claims, 24 Drawing Sheets

Specification includes a Sequence Listing.

(56) References Cited

OTHER PUBLICATIONS

Van der Oost et al., Unravelling the structural and mechanistic basis of CRISPR-Cas systems. Nature Reviews Microbiology (2014), 12: 479-492 (Year: 2014).*
Communication, dated Mar. 3, 2021, issued by the European Patent Office in European Patent Application No. 18812837.5.
Hochstrasser, et al., "CasA mediates Cas3-catalyzed target degradation during CRISPR RNA-guided interference," Proceedings of the National Academy of Sciences, vol. 111, No. 18, 2014, pp. 6618-6623.
Westra et al., "CRISPR Immunity Relies on the Consecutive Binding and Degradation of Negatively Supercoiled Invader DNA by Cascade and Cas3," Molecular Cell, vol. 46, No. 5, 2012, pp. 595-605.
Gong, et al., "Molecular insights into DNA interference by CRISPR-associated nuclease-helicase Cas3," Proceedings of the National Academy of Sciences, vol. 111, No. 46, 2014, p. 16359-16364.
Jore et al., "Structural basis for CRISPR RNA-guided DNA recognition by Cascade," Nature Structural & Molecular Biology, vol. 18, No. 5, 2011, pp. 529-536.
Martin Jinek et al., "A Programmable Dual-RNA-Guided DNA Endonuclease in Adaptive Bacterial Immunity", Science, Aug. 17, 2012, pp. 816-821, vol. 337.
Sabin Mulepati et al., "In Vitro Reconstitution of an *Escherichia coli* RNA-guided Immune System Reveals Unidirectional, ATP-dependent Degradation of DNA Target", The Journal of Biological Chemistry, Aug. 2, 2013, pp. 22184-22192, vol. 288, No. 31.
Ahmed A. Gomaa et al., "Programmable Removal of Bacterial Strains by Use of Genome-Targeting CRISPR-Cas Systems", mBio, Jan./Feb. 2014, pp. 1-9, vol. 5, Issue 1.
Keiichiro Suzuki et al., "In vivo genome editing via CRISPR/Cas9 mediated homology—independent targeted integration", Nature, Dec. 1, 2016, 24 pgs., vol. 540.
H. Morisaka et al., "Genetic Disease, Gene Regulation and Gene Therapy", Journal of Investigative Dermatology, May 2017, 3 pgs., vol. 137, No. 5.
Hiroyuki Morisaka et al., "Genome editing in mammalian cells by Cascade and Cas3", The 42nd Annual Meeting of the Japanese Society for Investigative Dermatology, Nov. 2, 2017, P07-20 [04-12], 3pgs.
International Search Report for PCT/JP2018/022066 dated, Sep. 4, 2018 (PCT/ISA/210).
Communication, dated Dec. 12, 2019, issued in International Application No. PCT/JP2018/022066.

* cited by examiner

| | | | | | | | | | | | | |
|---|---|---|---|---|---|---|---|---|---|---|---|---|
| Cas3 | + | - | + | + | + | + | + | + | - | + | + | - |
| Cse1(Cas8) | + | + | - | + | + | + | + | + | - | + | + | - |
| Cse2(Cas11) | + | + | + | - | + | + | + | + | - | + | + | - |
| Cas7 | + | + | + | + | - | + | + | + | - | + | + | - |
| Cas5 | + | + | + | + | + | - | + | + | - | + | + | - |
| Cas6 | + | + | + | + | + | + | - | + | - | + | + | - |
| CCR5-crRNA | + | + | + | + | + | + | + | - | - | - | + | - |
| CCR5-target | + | + | + | + | + | + | + | + | - | - | - | - |
| spacer-crRNA | - | - | - | - | - | - | - | + | - | + | - | - |
| spacer-target | - | - | - | - | - | - | - | - | - | + | + | - |

Fig. 3A

CLONE 1 ccacttggaggggtgaggtgagaggattgcttgagcccgggatggtccaggctgcagtgagccatgatcgtg
ccactgcactccagcctgggcgacagagtgagaccctgtctcacaacaacaacaacaacaacaaaaggct
gagctgcaccatgcttgacccagtttcttaaaattgttgtcaaagcttcattcactccatggtgctatagagca
caagattttatttggtgagatggtgctttcatgaattcccccaacagagccaagctctccatctagtggacag
ggaagctagcagcaaaccttcccttcactacaaaacttcattgcttggccaaaaagagagttaattcaatgt
agacatctatgtaggcaattaaaaacctattgatgtataaaacagtttgcattcatggagggcaactaaata
cattctaggactttataaaagatcacttttttatttatgcacagGGTGGAACAAGATGGATTAT
CAAGTGTCAAGTCCAATCTATGACATCAATTATTATACATCGGAG
CCCTGCCAAAAAATCAATGTGAAGCAAATCGCAGCCCGCCTCCTGCCTC
CGCTCTACTCACTGGTGTTCATCTTTGGTTTTGTGGGCAACATGCTGGT
CATCCTCATCCTGATAAACTGCAAAAGGCTGAAGAGCATGACTGACATC
TACCTGCTCAACCTGGCCATCTCTGACCTGTTTTTCCTTCTTACTGTCCC
CTTCTGGGCTCACTATGCTGCCGCCCAGTGGGACTTTGGAAATACAATG
TGTCAACTCTTGACAGGGCTCTATTTTATAGGCTTCTTCTCTGGAATCT
TCTTCATCATCCTCCTGACAATCGATAGGTACCTGGCTGTCGTCCATGC
TGTGTTTGCTTTAAAAGCCAGGACGGTCACCTTTGGGGTGGTGACAAG
TGTGATCACTTGGGTGGTGGCTGTGTTTGCGTCTCTCCCAGGAATCATC
TTTA □ : 401bp deletion (FOR LAST CA, THERE IS CA IMMEDIATELY BEFORE DELETION)

— : PAM + target sequence

Fig. 3B

CLONE 2 ccacttggaggggtgaggtgagaggattgcttgagcccgggatggtccaggctgcagtgagccatgatcgtg
ccactgcactccagcctgggcgacagagtgagaccctgtctcacaacaacaacaacaacaacaaaaaggct
gagctgcaccatgcttgacccagtttcttaaaattgttgtcaaagcttcattcactccatggtgctatagagca
caagattttatttggtgagatggtgctttcatgaattcccccaacagagccaagctctccatctagtggacag
ggaagctagcagcaaaccttcccttcactacaaaacttcattgcttggccaaaaagagagttaattcaatgt
agacatctatgtaggcaattaaaaacctattgatgtataaaacagtttgcattcatggagggcaactaaata
cattctaggactttataaaagatcagttttatttatgcacagGGTGGAACAAGATGGATTAT
CAAGTGTCAAGTCCAATCTATGACATCAATTATTATACATCGGAG
CCCTGCCAAAAAATCAATGTGAAGCAAATCGCAGCCCGCCTCCTGCCTC
CGCTCTACTCACTGGTGTTCATCTTTGGTTTTGTGGGCAACATGCTGGT
CATCCTCATCCTGATAAACTGCAAAAGGCTGAAGAGCATGACTGACATC
TACCTGCTCAACCTGGCCATCTCTGACCTGTTTTTCCTTCTTACTGTCCC
CTTCTGGGCTCACTATGCTGCCGCCCAGTGGGACTTTGGAAATACAATG
TGTCAACTCTTGACAGGGCTCTATTTTATAGGCTTCTTCTCTGGAATCT
TCTTCATCATCCTCCTGACAATCGATAGGTACCTGGCTGTCGTCCATGC
TGTGTTTGCTTTAAAAGCCAGGACGGTCACCTTTGGGGTGGTGACAAG
TGTGATCACTTGGGTGGTGGCTGTGTTTGCGTCTCTCCCAGGAATCATC
TTTA □ : 341bp deletion (FOR LAST AC, THERE IS AC IMMEDIATELY BEFORE DELETION)

— : PAM + target sequence

Fig. 3C

CLONE 3 ccacttggaggggtgaggtgagaggattgcttgagcccgggatggtccaggctgcagtgagccatgatcgtg
ccactgcactccagcctgggcgacagagtgagaccctgtctcacaacaacaacaacaacaacaaaaaggct
gagctgcaccatgcttgacccagtttcttaaaattgttgtcaaagcttcattcactccatggtgctatagagca
caagattttatttggtgagatggtgctttcatgaattccccaacagagccaagctctccatctagtggacag
ggaagctagcagcaaaccttcccttcactacaaacttcattgcttggccaaaaagagagttaattcaatgt
agacatctatgtaggcaattaaaaacctattgatgtataaaacagtttgcattcatggagggcaactaaata
cattctaggactttataaaagatcactttttatttatgcacagGGTGGAACAAGATGGATTAT
CAAGTGTCAAGTCCAATCTATGACATCAATTATTATACATCGGAG
CCCTGCTAAAAAAATCAATGTGAAGCAAATCGCAGCCCGCCTCCTGCCT
CCGCTCTACTCACTGGTGTTCATCTTTGGTTTTGTGGGCAACATGCTGG
TCATCCTCATCCTGATAAACTGCAAAAGGCTGAAGAGCATGACTGACAT
CTACCTGCTCAACCTGGCCATCTCTGACCTGTTTTTCCTTCTTACTGTCC
CCTTCTGGGCTCACTATGCTGCCGCCCAGTGGGACTTTGGAAATACAAT
GTGTCAACTCTTGACAGGGCTCTATTTTATAGGCTTCTTCTCTGGAATC
TTCTTCATCATCCTCCTGACAATCGATAGGTACCTGGCTGTCGTCCATG
CTGTGTTTGCTTTAAAAGCCAGGACGGTCACCTTTGGGGTGGTGACAA
GTGTGATCACTTGGGTGGTGGCTGTGTTTGCGTCTCTCCCAGGAATCAT
CTTTA □ : 268bp deletion (NO HOMOLOGY BEFORE AND AFTER DEL)

— : PAM + target sequence

= : C>TA WAVEFORM OF SEQ IS CLEAR

Fig. 3D

CLONE 4 ccacttggaggggtgaggtgagaggattgcttgagcccgggatggtccaggctgcagtgagccatgatcgtg
ccactgcactccagcctgggcgacagagtgagaccctgtctcacaacaacaacaacaacaacaaaaaggct
gagctgcaccatgcttgacccagtttcttaaaattgttgtcaaagcttcattcactccatggtgctatagagca
caagattttatttggtgagatggtgctttcatgaattccccaacagagccaagctctccatctagtggacag
ggaagctagcagcaaaccttcccttcactacaaacttcattgcttggccaaaaagagagttaattcaatgt
agacatctatgtaggcaattaaaaacctattgatgtataaacagtttgcattcatggagggcaactaaata
cattctaggactttataaaagatcactttttatttatgcacagGGTGGAACAAGATGGATTAT
CAAGTGTCAAGTCCAATCTATGACATCAATTATTATACATCGGAG
CCCTGCCAAAAAATCAATGTGAAGCAAATCGCAGCCCGCCTCCTGCCTC
CGCTCTACTCACTGGTGTTCATCTTTGGTTTTGTGGGCAACATGCTGGT
CATCCTCATCCTGATAAACTGCAAAAGGCTGAAGAGCATGACTGACATC
TACCTGCTCAACCTGGCCATCTCTGACCTGTTTTTCCTTCTTACTGTCCC
CTTCTGGGCTCACTATGCTGCCGCCCAGTGGGACTTTGGAAATACAATG
TGTCAACTCTTGACAGGGCTCTATTTTATAGGCTTCTTCTCTGGAATCT
TCTTCATCATCCTCCTGACAATCGATAGGTACCTGGCTGTCGTCCATGC
TGTGTTTGCTTTAAAAGCCAGGACGGTCACCTTTGGGGTGGTGACAAG
TGTGATCACTTGGGTGGTGGCTGTGTTTGCGTCTCTCCCAGGAATCATC
TTTA ☐ : 344bp deletion (NO HOMOLOGY BEFORE AND AFTER DEL)

DELETED SEQUENCE HAS BEEN REPLACED WITH CATCTACAT

~ : PAM + target sequence

Fig. 6A

CLONE 1

GGGCTTCTCCTGACTGTTCCTTGTGTGACCTGTTCCCACATCTGGATGGGCTGCAGGA
GCCAGTGCTGTGGGGACAGAAGGTCTGGAGCTGCCCGTGAAGGGCAGAATGCTGCCC
TCAGACCCGCTTCCTCCCTGTCCTTGTCTGTCCAAGGAGAATGAGGTCTCACTGGTGG
ATTTCGGACTACCCTGAGGAGCTGGCACCTGAGGGACAAGGCCCCCACCTGCCCAGC
TCCAGCCTCTGATGAGGGGTGGGAGAGAGCTACATGAGGTTGCTAAGAAAGCCTCCCC
TGAAGGAGACCACACAGTGTGTGAGGTTGGAGTCTCTAGCAGCGGTTCTGTGCCCCC
AGGGATAGTCTGGCTGTCCAGGCACTGCTCTTGATATAAACACCACCTCCTAGTTATGA
AACCATGCCCATTCTGCCTCTCTGTATGGAAAAGAGCATGGGGCTGGCCCGTGGGGTG
GTGTCCACTTTAGGCCCTGTGGGAGATCATGGGAACCCACGCAGTGGGTCATAGGCTC
TCTCATTTACTACTCACATCCACTCTGTGAAGAAGCGATTATGATCTCTCCTCTAGAAA
CTCGTAGAGTCCCATGTCTGCCGGCTTCCAGAGCCTGCACTCCTCCACCTTGGCTTGG
CTTTGCTGGGGCTAGAGGAGCTAGGATGCACAGCAGCTCTGTGACCCTTTGTTTGAGA
GGAACAGGAAAACCACCCTTCTCTCTGGCCCACTGTGTCCTCTTCCTGCCCTGCCATCC
CCTTCTGTGAATGTTAGACCCATGGGAGCAGCTGGTCAGAGGGGACCCCGGCCTGGG
GCCCCTAACCCTATGTAGCCTCAGTCTTCCCATCAGGCTCTCAGCTCAGCCTGAGTGTT
GAGGCCCCAGTGGCTGCTCTGGGGGCCTCCTGAGTTTCTCATCTGTGCCCCTCCCTCC
CTGGCCCAGGTGAAGGTGTGGTTCCAGAACCGGAGGACAAAGTACAAACGGCAGAAG
CTGGAGGAGGAAGGGCCTGAGTCCGAGCAGAAGAAGAAGGGCTCCCATCACATCAAC
CGGTGGCGCATTGCCACGAAGCAGGCCAATGGGGAGGACATCGATGTCACCTCCAATG
ACTAGGGTGGGCAACCACAAACCCACGAGGGCAGAGTGCTGCTTGCTGCTGGCCAGG
CCCCTGCGTGGGCCCAAGCTGGACTCTGGCCACTCCCTGGCCAGGCTTTGGGGAGGCC
TGGAGTCATGGCCCCACAGGGCTTGAAGCCCGGGGCCGCCATTGACAGAGGGACAAG
CAATGGGCTGGCTGAGGCCTGGGACCACTTGGCCTTCTCCTCGGAGAGCCTGCCTGCC
TGGCGGGCCCGCCCGCCACCGCAGCCTCCCAGCTGCTCTCCGTGTCTCCAATCTCCC
TTTTGTTTTGATGCATTTCTGTTTTAATTTATTTTCCAGGCACCACTGTAGTTTAGTGAT
CCCCAGTGTCCCCCTTCCCTATGGGAATAATAAAAGTCTCTCTCTTAATGACACGGGCA
TCCAGCTCCAGCCCCAGAGCCTGGGGTGGTAGATTCCGGCTCTGAGGGCCAGTGGGG
GCTGGTAGAGCAAACGCGTTCAGGGCCTGGGAGCCTGGGGTGGGGTACTGGTGGAGG
GGGTCAAGGGTAATTCATTAACTCCTCTCTTTTGTTGGGGGACCCTGGTCTCTACCTCC
AGCTCCACAGCAGGAGAAACAGGCTAGACATAGGGAAGGGCCATCCTG

☐ : 513bp, 363bp del micro homology: CTC, T

— : PAM + target sequence

Fig. 6B

CLONE 2

GGGCTTCTCCTGACTGTTCCTTGTGTGACCTGTTCCCACATCTGGATGGGCTGCAGGA
GCCAGTGCTGTGGGGACAGAAGGTCTGGAGCTGCCCGTGAAGGGCAGAATGCTGCCC
TCAGACCCGCTTCCTCCCTGTCCTTGTCTGTCCAAGGAGAATGAGGTCTCACTGGTGG
ATTTCGGACTACCCTGAGGAGCTGGCACCTGAGGGACAAGGCCCCCCACCTGCCCAGC
TCCAGCCTCTGATGAGGGGTGGGAGAGAGCTACATGAGGTTGCTAAGAAAGCCTCCCC
TGAAGGAGACCACACAGTGTGTGAGGTTGGAGTCTCTAGCAGCGGGTTCTGTGCCCCC
AGGGATAGTCTGGCTGTCCAGGCACTGCTCTTGATATAAACACCACCTCCTAGTTATGA
AACCATGCCCATTCTGCCTCTCTGTATGGAAAAGAGCATGGGCTGGCCCGTGGGGTG
GTGTCCACTTTAGGCCCTGTGGGAGATCATGGGAACCCACGCAGTGGGTCATAGGCTC
TCTCATTTACTACTCACATCCACTCTGTGAAGAAGCGATTATGATCTCTCCTCTAGAAA
CTCGTAGAGTCCCATGTCTGCCGGCTTCCAGAGCCTGCACTCCTCCACCTTGGCTTGG
CTTTGCTGGGGCTAGAGGAGCTAGGATGCACAGCAGCTCTGTGACCCTTTGTTTGAGA
GGAACAGGAAAACCACCCTTCTCTCTGGCCCACTGTGTCCTCTTCCTGCCCTGCCATCC
CCTTCTGTGAATGTTAGACCCATGGGAGCAGCTGGTCAGAGGGGACCCCGGCCTGGG
GCCCCTAACCCTATGTAGCCTCAGTCTTCCCATCAGGCTCTCAGCTCAGCCTGAGTGTT
GAGGCCCCAGTGGCTGCTCTGGGGGCCTCCTGAGTTTCTCATCTGTGCCCCTCCCTCC
CTGGCCCAGGTGAAGGTGTGGTTCCAGAACCGGAGGACAAAGTACAAACGGCAGAAG
CTGGAGGAGGAAGGGCCTGAGTCCGAGCAGAAGAAGAAGGGCTCCCATCACATCAAC
CGGTGGCGCATTGCCACGAAGCAGGCCAATGGGGAGGACATCGATGTCACCTCCAATG
ACTAGGGTGGGCAACCACAAACCCACGAGGGCAGAGTGCTGCTTGCTGCTGGCCAGG
CCCCTGCGTGGGCCCAAGCTGGACTCTGGCCACTCCCTGGCCAGGCTTTGGGGAGGCC
TGGAGTCATGGCCCCACAGGGCTTGAAGCCCGGGGCCGCCATTGACAGAGGGACAAG
CAATGGGCTGGCTGAGGCCTGGGACCACTTGGCCTTCTCCTCGGAGAGCCTGCCTGCC
TGGGCGGGCCCGCCCGCCACCGCAGCCTCCCAGCTGCTCTCCGTGTCTCCAATCTCCC
TTTTGTTTTGATGCATTTCTGTTTTAATTTATTTTCCAGGCACCACTGTAGTTTAGTGAT
CCCCAGTGTCCCCCTTCCCTATGGGAATAATAAAAGTCTCTCTCTTAATGACACGGGCA
TCCAGCTCCAGCCCCAGAGCCTGGGGTGGTAGATTCCGGCTCTGAGGGCCAGTGGGG
GCTGGTAGAGCAAACGCGTTCAGGGCCTGGGAGCCTGGGGTGGGGTACTGGTGGAGG
GGGTCAAGGGTAATTCATTAACTCCTCTCTTTTGTTGGGGGACCCTGGTCTCTACCTCC
AGCTCCACAGCAGGAGAAACAGGCTAGACATAGGGAAGGGCCATCCTG

□ : 694bp del  micro homology

~ : PAM + target sequence

| | 1 | 2 | 3 | 4 | 5 | 6 | 7 | 8 |
|---|---|---|---|---|---|---|---|---|
| Cas3 | + | − | + | + | − | + | + | − |
| Cascade(2A) | + | + | − | + | − | + | + | − |
| CCR5 crRNA | + | + | + | − | − | − | + | − |
| CCR5 target | + | + | + | + | + | − | - | − |
| Spacer1 crRNA | − | − | − | + | − | + | − | − |
| Spacer1 target | − | − | − | - | − | + | + | + |

Fig. 10A

PRE-crRNA (LRSR) : TGGATGTGTTGTTTGTGTGATACTATAAAGTTGGT
AGATTGTGACTGGCTTAAAAAATCATTAATTAATAATAGGTTATGTTTAG
A|GTGTTCCCCGCGCCAGCGGGGATAAACCG|CAGGCCAATGGGGAGG
ACATCGATGTCACCTC|GTGTTCCCCGCGCCAGCGGGGATAAACCG (SEQ ID NO: 71)

PRE-crRNA (RSR) : GTGTTCCCCGCGCCAGCGGGGATAAACCG|CAGGC
CAATGGGGAGGACATCGATGTCACCTC|GTGTTCCCCGCGCCAGCGGG
GATAAACCG (SEQ ID NO: 72)

MATURE crRNA : ATAAACCG|CAGGCCAATGGGGAGGACATCGATGTCACCT
C|GTGTTCCCCGCGCCAGCGGGG (SEQ ID NO: 73)

Fig. 16

```
Emx1                                                    1.7 Kbp
 WT    TGC//TCACATCAACCGGTGGCGCATTGCCACG AAGCAG//CTT
                        SEQ ID NO: 75

 #3    TGC//CTGCC---(~1447bp)--- --------CTACC//CTT
                        SEQ ID NO: 76

 #5    TGC//GCCCA---(~1370bp)--- --------CCTGG//CTT
                        SEQ ID NO: 77

 #6    TGC//GAGCT---(~797bp)---GAGGA//CG AAGCAG//CTT
                        SEQ ID NO: 78

 #19   TGC//ACCCT---(~994bp)--- --------CAGCT//CTT
                        SEQ ID NO: 79

 #27   TGC//GCCCA---(~1370bp)--- --------CCTGG//CTT

 #33   TGC//TGAGG---(~690bp)---TCTCA//CG AAGCAG//CTT
                        SEQ ID NO: 80

 #38   TGC//GGACT---(~690bp)---AGGCC//CG AAGCAG//CTT
                        SEQ ID NO: 81

 #41   TGC//GGACT---(~834bp)---AAGAA//CG AAGCAG//CTT
                        SEQ ID NO: 82

 #93   TGC//TGATG---(~820bp)--- ---CAGGCCAATGGG//CTT
                        SEQ ID NO: 83
```

METHOD FOR PRODUCING DNA-EDITED EUKARYOTIC CELL, AND KIT USED IN THE SAME

CROSS REFERENCE TO RELATED APPLICATIONS

This application is a National Stage of International Application No. PCT/JP2018/022066 filed on Jun. 8, 2018, claiming priority based on Japanese Patent Application No. 2017-113747 filed on Jun. 8, 2017.

INCORPORATION BY REFERENCE OF SEQUENCE LISTING

The instant application contains a Sequence Listing which has been filed electronically in ASCII plain text format and is hereby incorporated by reference in its entirety. Said text copy, created on Apr. 21, 2023, is named Substitute_Sequence_Listing.txt and is 126 KB in size.

TECHNICAL FIELD

The present invention relates to a method for producing DNA-edited eukaryotic cells, animals, and plants, and to a kit used in the method.

BACKGROUND ART

Bacteria and archaea have adaptive immune mechanisms which specifically recognize and eliminate organisms such as foreign phages that intend to intrude from the outside. These systems, called the CRISPR-Cas systems, first introduce genomic information on the foreign organisms into the self genome (adaptation). Then, when the same foreign organisms intend to intrude again, the systems cleave and eliminate the foreign genomes by using the complementarity of the information introduced in the self genome and the genome sequence (interference).

Recently, genome editing (DNA editing) techniques using the above CRISPR-Cas systems as “DNA editing tools” have been developed (NPL 1).

The CRISPR-Cas systems are roughly divided into “Class 1” and “Class 2,” in which effectors working in the process of cleaving DNA are composed of multiple Cas and a single Cas, respectively. Among other things, as the Class 1 CRISPR-Cas systems, “type I” involving Cas3 and Cascade complexes (meaning Cascade-crRNA complexes, and the same applies below) is widely known. As the Class 2 CRISPR-Cas systems, “type II” involving Cas9 is widely known (hereinafter, regarding the CRISPR-Cas systems, “Class 1 type I” and “Class 2 type II” may be simply referred to as “type I” and “type II,” respectively). In addition, what have been widely used in the conventional DNA editing techniques are the Class 2 CRISPR-Cas systems involving Cas9 (which hereinafter may be referred to as the “CRISPR-Cas9 systems”). For example, NPL 1 reports a Class 2 CRISPR-Cas system which cleaves DNA using Cas9.

On the other hand, for the Class 1 CRISPR-Cas systems, which cleave DNA using Cas3 and Cascade complexes (which hereinafter may also be referred to as the “CRISPR-Cas3 systems”), no successful example of genomic editing has been reported in eukaryotic cells despite a lot of effort. For example, NPL 2 and NPL 3 reported that simple use of a CRISPR-Cas3 system made it possible to completely degrade target DNA in a cell-free system and selectively remove specific *E. coli* strains. However, these do not mean the success of genome editing, nor have they been demonstrated at all in eukaryotic cells. In addition, PTL 1 proposes to perform genome editing using the FokI nuclease in place of Cas3 in eukaryotic cells (Example 7, FIG. 7, and FIG. 11) because the CRISPR-Cas3 systems degrade target DNA in *E. coli* by helicase activity and exonuclease activity of Cas3 (Example 5 and FIG. 6). Moreover, PTL 2 proposes deletion of cas3 and repurposing for programmable gene repression by use of inactivated Cas3 (Cas3' and Cas3') (for example, Example 15 and claim 4(e)) because the CRISPR-Cas3 systems degrade target DNA in *E. coli* (FIG. 4).

CITATION LIST

Patent Literature

[PTL 1] Published Japanese Translation of PCT International Application No. 2015-503535

[PTL 2] Published Japanese Translation of PCT International Application No. 2017-512481

Non Patent Literature

[NPL 1] Jinek M et al. (2012) A Programmable Dual-RNA Guided DNA Endonuclease in Adaptive Bacterial Immunity, Science, Vol. 337 (Issue 6096), pp. 816-821

[NPL 2] Mulepati S & Bailey S (2013) In Vitro Reconstitution of an Escherichia coli RNA-guided Immune System Reveals Unidirectional, ATP-dependent Degradation of DNA Target, Journal of Biological Chemistry, Vol. 288 (No. 31), pp. 22184-22192

[NPL 3] Ahmed A. Gomaa et al. (2014) Programmable Reomoval of Bacterial Strains by Use of Genome Targeting CRISPR-Cas Systems, mbio.asm.org, Volume 5, Issue 1, e00928-13

SUMMARY OF INVENTION

Technical Problem

The present invention has been made in view of the above circumstances, and an object thereof is to establish a CRISPR-Cas3 system in eukaryotic cells.

Solution to Problem

The present inventors have made earnest studies to achieve the above object, and finally succeeded in establishing a CRISPR-Cas3 system in eukaryotic cells. The most widely used CRISPR-Cas9 system has succeeded in genome editing in various eukaryotic cells, but this system usually uses a mature crRNA as a crRNA. However, it was surprising that, in the CRISPR-Cas3 systems, genome editing was difficult in eukaryotic cells in the case of using a mature crRNA and that efficient genomic editing was possible only by using a pre-crRNA, which usually was not used as a constituent element of a system. That is, in order to make the CRISPR-Cas3 systems function in eukaryotic cells, cleaving of a crRNA by proteins constituting the Cascade was found to be important. The CRISPR-Cas3 systems using this pre-crRNA were widely applicable not only to the type I-E system but also to the type I-F and type I-G systems. Moreover, addition of a nuclear localization signal, particularly a bipartite nuclear localization signal to Cas3 made it possible to further improve the genome editing efficiency for the CRISPR-Cas3 systems in eukaryotic cells.

Furthermore, the present inventors have found that the CRISPR-Cas3 systems, unlike the CRISPR-Cas9 systems can cause a large deletion in a region containing a PAM sequence or in an upstream region thereof. These findings have led to the completion of the present invention.

Specifically, the present invention relates to a CRISPR-Cas3 system in eukaryotic cells, and more specifically to the following invention.

[1] A method for producing a DNA-edited eukaryotic cell, comprising: introducing a CRISPR-Cas3 system into a eukaryotic cell, wherein the CRISPR-Cas3 system includes the following (A) to (C).

(A) a Cas3 protein, a polynucleotide encoding the protein, or an expression vector containing the polynucleotide, (B) a Cascade protein, a polynucleotide encoding the protein, or an expression vector containing the polynucleotide, and (C) a crRNA, a polynucleotide encoding the crRNA, or an expression vector containing the polynucleotide.

[2] A method for producing a DNA-edited animal (excluding a human) or plant, comprising: introducing a CRISPR-Cas3 system into an animal (excluding a human) or plant, wherein the CRISPR-Cas3 system includes the following (A) to (C).

(A) a Cas3 protein, a polynucleotide encoding the protein, or an expression vector containing the polynucleotide, (B) a Cascade protein, a polynucleotide encoding the protein, or an expression vector containing the polynucleotide, and (C) a crRNA, a polynucleotide encoding the crRNA, or an expression vector containing the polynucleotide.

[3] The method according to [1] or [2], further comprising cleaving the crRNA with a protein constituting the Cascade protein after introducing the CRISPR-Cas3 system into the eukaryotic cell.

[4] The method according to [1] or [2], wherein the crRNA is a pre-crRNA.

[5] The method according to any one of [1] to [4], wherein a nuclear localization signal is added to the Cas3 protein and/or the Cascade protein.

[6] The method according to [5], wherein the nuclear localization signal is a bipartite nuclear localization signal.

[7] A kit for use in the method according to any one of [1] to [6], the kit comprising the following (A) and (B).

(A) a Cas3 protein, a polynucleotide encoding the protein, or an expression vector containing the polynucleotide and (B) a Cascade protein, a polynucleotide encoding the protein, or an expression vector containing the polynucleotide.

[8] The kit according to [7], further comprising a crRNA, a polynucleotide encoding the crRNA, or an expression vector containing the polynucleotide.

[9] The kit according to [8], wherein the crRNA is a pre-crRNA.

[10] The kit according to any one of [7] to [9], wherein a nuclear localization signal is added to the Cas3 protein and/or the Cascade protein.

[11] The kit according to [10], wherein the nuclear localization signal is a bipartite nuclear localization signal.

Note that in the present specification, the term "polynucleotide" intends a polymer of nucleotides and is used synonymously with the term "gene," "nucleic acid," or "nucleic acid molecule." The polynucleotide may also be present in the form of DNA (for example, cDNA or genomic DNA) or in the form of RNA (for example, mRNA). Also, the term "protein" is used synonymously with "peptide" or "polypeptide."

Advantageous Effects of Invention

Use of the CRISPR-Cas3 system of the present invention made it possible to edit DNA in eukaryotic cells.

BRIEF DESCRIPTION OF DRAWINGS

FIG. 3A is a diagram showing the CCR5 gene (clone 1, SEQ ID NO: 64) in which a part of the nucleic acid sequence has been deleted by the CRISPR-Cas3 system.

FIG. 3B is a diagram showing the CCR5 gene (clone 2, SEQ ID NO: 65) in which a part of the nucleic acid sequence has been deleted by the CRISPR-Cas3 system.

FIG. 3C is a diagram showing the CCR5 gene (clone 3, SEQ ID NO: 66) in which a part of the nucleic acid sequence has been deleted by the CRISPR-Cas3 system.

FIG. 3D is a diagram showing the CCR5 gene (clone 4, SEQ ID NO: 67) in which a part of the nucleic acid sequence has been deleted by the CRISPR-Cas3 system.

FIG. 4(*b*) is a schematic diagram showing the structure of a Cas3 plasmid. FIG. 4(*c*) is a schematic diagram showing the structure of a pre-crRNA plasmid. FIG. 4(*d*) is a schematic diagram showing the structure of a reporter vector (including the target sequence).

FIG. 6A is a diagram showing the EMX1 gene (clone 1, SEQ ID NO: 69) deleted in part of the nucleic acid sequence by the CRISPR-Cas3 system.

FIG. 6B is a diagram showing the EMX1 gene (clone 2, SEQ ID NO: 70) deleted in part of the nucleic acid sequence by the CRISPR-Cas3 system.

FIG. 10A is a diagram showing the structures of the pre-crRNAs (LRSR and RSR, SEQ ID NOs: 71 and 72 respectively) and the mature crRNA (SEQ ID NO: 73) used in Examples. In the figure, the underlines show the 5' handle (Cas5 handle), and the double underlines shows the 3' handle (Cash handle).

FIG. 16 is a diagram showing the magnitude of deletion by the CRISPR-Cas3 system detected by the sequencing of a TA cloning sample of a PCR product.

DESCRIPTION OF EMBODIMENTS

[1] Method for Producing DNA-Edited Eukaryotic Cells, Animals, and Plants

A method of the present invention comprises introducing a CRISPR-Cas3 system into a eukaryotic cell, wherein the CRISPR-Cas3 system includes the following (A) to (C).

(A) a Cas3 protein, a polynucleotide encoding the protein, or an expression vector containing the polynucleotide, (B) a Cascade protein, a polynucleotide encoding the protein, or an expression vector containing the polynucleotide, and (C) a crRNA, a polynucleotide encoding the crRNA, or an expression vector containing the polynucleotide The Class 1 CRISPR-Cas systems are classified into type I and type III, and depending on the types of proteins constituting the Cascade (hereinafter simply referred to as the "Cascade" or the "Cascade proteins"), type I is further classified into six types of type I-A, type I-B, type I-C, type I-D, type I-E, and type I-F as well as type I-G, a subtype of type I-B (for example, see [van der Oost J et al. (2014) Unravelling the structural and mechanistic basis of CRISPR-Cas systems, Nature Reviews Microbiologym, Vol. 12 (No. 7), pp. 479-492] and [Jackson RN et al. (2014) Fitting CRISPR-associated Cas3 into the Helicase Family Tree, Current Opinion in Structural Biology, Vol. 24, pp. 106-114]).

The type I CRISPR-Cas systems have the function of cleaving DNA by cooperation of Cas3 (protein having nuclease activity and helicase activity), Cascade, and crRNAs. They are referred to as the "CRISPR-Cas3 system" in the present invention because Cas3 is used as a nuclease.

Use of the CRISPR-Cas3 system of the present invention makes it possible to obtain, for example, the following advantages.

First, the crRNA used in the CRISPR-Cas3 system generally recognizes a target sequence of 32 to 37 bases (Ming Li et al., Nucleic Acids Res. 2017 May 5; 45(8): 4642-4654). On the other hand, the crRNA used in the CRISPR-Cas9 system generally recognizes a target sequence of 18 to 24 bases. Therefore, it is considered that the CRISPR-Cas3 system can recognize target sequences more accurately than the CRISPR-Cas9 system.

Figure 12:
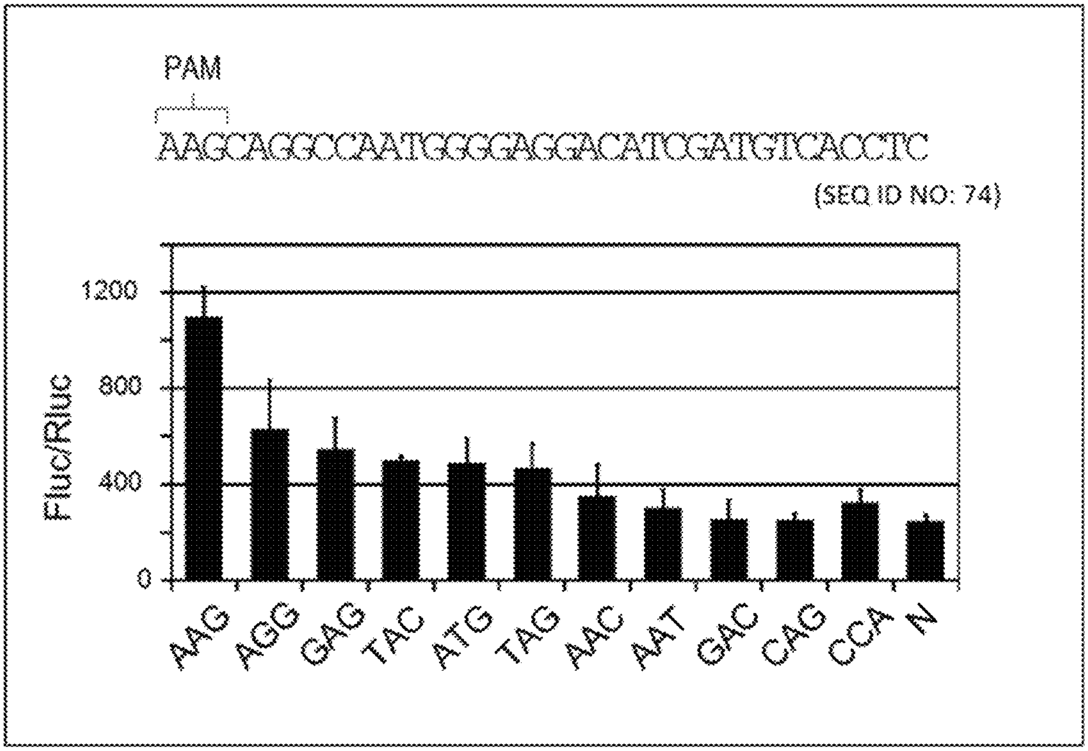
FIG. 12 is a diagram showing the effects of the PAM sequence on the DNA cleavage activity of the CRISPR-Cas3 system.

In addition, the PAM sequence of the Class 2 type II system, the CRISPR-Cas9 system, is "NGG (N is an arbitrary base)" adjacent to the 3' side of the target sequence. Also, the PAM sequence of the Class 2 type V system, the CRISPR-Cpf1 system, is "AA" adjacent to the 5' side of the target sequence. On the other hand, the PAM sequence of the CRISPR-Cas3 system of the present invention is "AAG" adjacent to the 5' side of the target sequence or a nucleic acid sequence similar to that (for example, "AGG," "GAG," "TAC," "ATG," "TAG," and the like) (FIG. 12). Thus, it is considered that, by using the CRISPR-Cas3 system of the present invention, regions which cannot be recognized by conventional methods can be subjected to DNA editing.

Furthermore, unlike the above Class 2 CRISPR-Cas systems, the CRISPR-Cas3 system causes DNA cleavages at multiple locations. Therefore, use of the CRISPR-Cas3 system of the present invention makes it possible to generate a wide range of deletion mutations ranging from one hundred to several thousand, and possibly even more bases (FIGS. 3, 6, and 16 to 18). It is considered that this function can be used for knocking out a long genomic region or knocking in long DNA. When performing knock-in, donor DNA is usually used, and the donor DNA is also a molecule constituting the CRISPR-Cas3 system of the present invention.

Note that, when simply described as "Cas3" in the present specification, it means a "Cas3 protein." The same applies to Cascade proteins.

Figure 15:
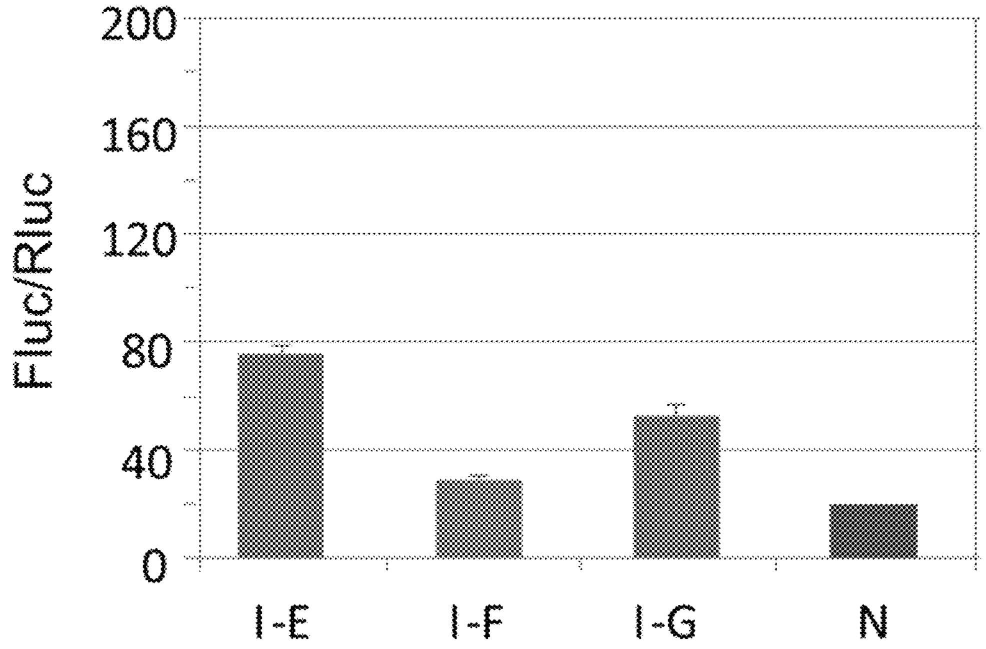
FIG. 15 shows a comparison of the DNA cleavage activity of the type I-E, type I-F, and type I-G CRISPR-Cas3 systems.

The CRISPR-Cas3 system of the present invention includes all six subtypes of type I. That is, although proteins constituting the CRISPR-Cas3 system may differ slightly in constitution and the like depending on the subtype (for example, the proteins constituting the Cascade are different), the present invention includes all of these proteins. Indeed, in the present example, it was found that genomic editing is possible not only for type I-E but also for type 1-G and type I-F systems (FIG. 15).

The type I-E CRISPR-Cas3 system, which is common among type I CRISPR-Cas3 systems, cleaves DNA when a crRNA cooperates with Cas3 and Cascade (Cse1 (Cas8), Cse2 (Cas11), Cas5, Cas6, and Cas7). The type I-A system has Cascade constituent elements of Cas8a1, Csa5 (Cas11), Cas5, Cas6, and Cas7, the type I-B has Cascade constituent elements of Cas8b1, Cas5, Cas6, and Cas7, the type I-C has Cascade constituent elements of Cas8c, Cas5, and Cas7, the type I-D has Cascade constituent elements of Cas10d, Csc1 (Cas5), Cas6, and Csc2 (Cas7), the type I-F has Cascade constituent elements of Csy1 (Cas8f), Csy2 (Cas5), Cas6, and Csy3 (Cas7), and the type I-G system has Cascade constituent elements Cst1 (Cas8a1), Cas5, Cas6, and Cst2 (Cas7). In the present invention, Cas3 and Cascade are collectively referred to as the "Cas protein group."

Hereinafter, the type I-E CRISPR-Cas3 system is described as a representative example. For other types of CRISPR-Cas3 systems, the Cascade constituting the systems may be interpreted as appropriate.

Cas Protein Group

In the CRISPR-Cas3 system of the present invention, the Cas protein group can be introduced into eukaryotic cells in the form of a protein, in the form of a polynucleotide encoding the protein, or in the form of an expression vector containing the polynucleotide. When the Cas protein group is introduced into eukaryotic cells in the form of a protein, it is possible to appropriately prepare the amount and the like of each protein, which is excellent from the viewpoint of handling. Moreover, taking into consideration, for example, the efficiency of cleavage in cells, it is also possible to first forma complex of the Cas protein group and then to introduce it to eukaryotic cells.

In the present invention, it is preferable to add a nuclear localization signal to the Cas protein group. The nuclear localization signal can be added to the N-terminus side and/or the C-terminus side of the Cas protein group (5'-end side and/or the 3'-end side of the polynucleotide encoding each Cas protein group). In this way, addition of a nuclear localization signal to the Cas protein group promotes localization to the nucleus in a cell, making it possible to efficiently perform DNA editing as a result.

The above nuclear localization signal is a peptide sequence composed of several to several tens of basic amino acids, and its sequence is not particularly limited as long as proteins are transferred into the nucleus. A specific example of such nuclear localization signal is described in, for example, [Wu J et al. (2009) The Intracellular Mobility of Nuclear Import Receptors and NLS Cargoes, Biophysical journal, Vol. 96 (Issue 9), pp. 3840-3849]. Any nuclear localization signal usually used in the technical field can be used in the present invention.

The nuclear localization signal may be, for example, PKKKRKV (SEQ ID NO: 52) (encoded by the nucleic acid sequence CCCAAGAAGAAGCGGAAGGTG (SEQ ID NO: 53)). When the above nuclear localization signal is used, it is preferable to arrange, for example, a polynucleotide composed of the nucleic acid sequence with SEQ ID NO: 53 on the 5'-end side of the polynucleotide encoding each Cas protein group. In addition, the nuclear localization signal can be, for example, KRTADGSEFESPKKKRKVE (SEQ ID NO: 54) (encoded by the nucleic acid sequence AAGCGGACTGCTGATGGCAGTGAATTTGAGTCCC-CAAAGAAGAAGAGAAAGGT GGAA (SEQ ID NO: 55)). When the above nuclear localization signal is used, it is preferable to arrange, for example, polynucleotides composed of the nucleic acid sequences with SEQ ID NO: 55 on both sides of the polynucleotide encoding each Cas protein group (specifically, to use a "bipartite nuclear localization signal (bpNLS)").

Such modifications are important for allowing the CRISPR-Cas3 system of the present invention to be expressed and to function efficiently in eukaryotic cells, together with the utilization of pre-crRNAs described later.

One preferred embodiment of the Cas protein group used in the present invention is as follows.

Cas3; a protein encoded by a polynucleotide composed of a nucleic acid sequence represented by SEQ ID NO: 1 or SEQ ID NO: 7

Cse1 (Cas8); a protein encoded by a polynucleotide composed of a nucleic acid sequence represented by SEQ ID NO: 2 or SEQ ID NO: 8

Cse2 (Cas11); a protein encoded by a polynucleotide composed of a nucleic acid sequence represented by SEQ ID NO: 3 or SEQ ID NO: 9

Cas5; a protein encoded by a polynucleotide composed of a nucleic acid sequence represented by SEQ ID NO: 4 or SEQ ID NO: 10

Cas6; a protein encoded by a polynucleotide composed of a nucleic acid sequence represented by SEQ ID NO: 5 or SEQ ID NO: 11

Cas7; a protein encoded by a polynucleotide composed of a nucleic acid sequence represented by SEQ ID NO: 6 or SEQ ID NO: 12

The above Cas protein group is (1) a protein obtained by adding PKKKRKV (SEQ ID NO: 52) as a nuclear localization signal to the N-termini of Cas3, Cse1 (Cas8), Cse2 (Cas11), Cas5, Cas6, and Cas7 of wild type *E. coli*, or (2) a protein obtained by adding KRTADGSEFESPKKKRKVE (SEQ ID NO: 54) as a nuclear localization signal to the N-termini and C-termini of Cas3, Cse1 (Cas8), Cse2 (Cas11), Cas5, Cas6, and Cas7 of wild type *E. coli*. With proteins having such amino acid sequences, the above Cas protein group can be transferred into the nucleus of a eukaryotic cell. The above Cas protein group transferred to the nucleus in this way cleaves the target DNA. In addition, it is possible to edit target DNA even in a DNA region having a strong structure considered to be difficult in the CRISPAR-Cas9 system (heterochromatin and the like).

Another embodiment of the proteins in the Cas protein group used in the present invention is a protein encoded by a nucleic acid sequence having 90% or more sequence identity with the nucleic acid sequence of the above Cas protein group. Another embodiment of the proteins in the Cas protein group used in the present invention is a protein encoded by a polynucleotide which hybridizes with a polynucleotide composed of a nucleic acid sequence complementary to the nucleic acid sequence of the Cas protein group described above under stringent conditions. Each of the above proteins has DNA cleavage activity when forming a complex with another protein constituting the Cas protein group. The meanings of terms such as "sequence identity" and "stringent conditions" are described later.

Polynucleotide Encoding Cas Protein Group

Polynucleotides encoding wild type proteins constituting the type I-E CRISPR-Cas system include polynucleotides modified to be efficiently expressed in eukaryotic cells. That is, it is possible to use a polynucleotide which encodes the Cas protein group and which has been modified. One preferred embodiment of the modification of polynucleotides is modification to a nucleic acid sequence suitable for expression in eukaryotic cells, for example, optimization of a codon to be expressed in eukaryotic cells.

One preferred embodiment of polynucleotides encoding the Cas protein group used in the present invention is as follows Cas3; a polynucleotide composed of a nucleic acid sequence represented by SEQ ID NO: 1 or SEQ ID NO: 7

Cse1 (Cas8); a polynucleotide composed of a nucleic acid sequence represented by SEQ ID NO: 2 or SEQ ID NO: 8

Cse2 (Cas11); a polynucleotide composed of a nucleic acid sequence represented by SEQ ID NO: 3 or SEQ ID NO: 9

Cas5; a polynucleotide composed of a nucleic acid sequence represented by SEQ ID NO: 4 or SEQ ID NO: 10

Cas6; a polynucleotide composed of a nucleic acid sequence represented by SEQ ID NO: 5 or SEQ ID NO: 11

Cas7; a polynucleotide composed of a nucleic acid sequence represented by SEQ ID NO: 6 or SEQ ID NO: 12

Each of these is a polynucleotide made to function and be expressed in mammalian cells by artificially modifying the nucleic acid sequences encoding the wild type Cas protein group of *E. coli* (Cas3; SEQ ID NO: 13, Cse1 (Cas8); SEQ ID NO: 14, Cse2 (Cas11); SEQ ID NO: 15, Cas5; SEQ ID NO: 16, Cas6; SEQ ID NO: 17, Cas7; SEQ ID NO: 18).

The above artificial modification of polynucleotides is to modify to a nucleic acid sequence suitable for expression in eukaryotic cells and to add a nuclear localization signal. Modification of a nucleic acid sequence and addition of a nuclear localization signal are as described above. As a result, it can be expected that, for the Cas protein group, the expression level will be sufficiently increased and the functions will be improved.

Another embodiment of polynucleotides encoding the Cas protein group used in the present invention is a polynucleotide formed by modifying a nucleic acid sequence encoding the wild type Cas protein group, composed of a nucleic acid sequence having 90% or more sequence identity with the nucleic acid sequence of the above Cas protein group. Proteins expressed from these polynucleotides have DNA cleavage activity when forming a complex with proteins expressed from other polynucleotides constituting the Cas protein group.

The sequence identity of nucleic acid sequences may be at least 90% or more and more preferably 95% or more (for example, 95%, 96%, 97%, 98%, and 99% or more) in the entire nucleic acid sequence (or the region encoding the site required for the functions of Cse3). It is possible to determine the identity of nucleic acid sequences using a program such as BLASTN (see [Altschul S F (1990) Basic local alignment search tool, Journal of Molecular Biology, Vol. 215 (Issue 3), pp. 403-410]). Examples of the parameters for analyzing nucleic acid sequences by BLASTN include score=100 and word length=12. Specific methods for analysis by BLASTN are known to those skilled in the art. Addition or deletion (gap and the like) may be allowed in order to align the nucleic acid sequences to be compared with the optimal state.

Moreover, "having DNA cleavage activity" is intended to mean the ability to cleave at least one site of a polynucleotide strand.

It is preferable for the CRISPR-Cas3 system of the present invention to cleave DNA by specifically recognizing the target sequence. For example, the dual-Luciferase assay described in Example A-1 makes it possible to know whether or not the CRISPR-Cas3 system specifically recognizes the target sequence.

Another embodiment of polynucleotides encoding the Cas protein group used in the present invention is a polynucleotide which hybridizes with a polynucleotide composed of a nucleic acid sequence complementary to the nucleic acid sequence of the Cas protein group described above under stringent conditions. Proteins expressed from these polynucleotides have DNA cleavage activity when forming a complex with proteins expressed from other polynucleotides constituting the Cas protein group.

Here, the "stringent conditions" refer to the conditions under which two polynucleotide strands form a double-stranded polynucleotide specific for a nucleic acid sequence but does not form a nonspecific double-stranded polynucleotide. The phrase "hybridizes under stringent conditions" can be said in other words as conditions capable of hybridizing in a temperature range from a melting temperature (Tm value) of nucleic acids with high sequence identity (for example, perfectly matched hybrids) to a temperature lower by 15° C., preferably by 10° C., and more preferably by 5° C.

Examples of the stringent conditions are shown as follows. First, two types of polynucleotides are hybridized for 16 to 24 hours at 60 to 68° C. (preferably 65° C. and more preferably 68° C.) in a buffer solution (pH 7.2) composed of 0.25 M $Na_2HPO_4$, 7% SDS, 1 mM EDTA, and 1×Denhardt's solution. Thereafter, washing is carried out twice for 15 minutes in a buffer solution (pH 7.2) composed of 20 mM $Na_2HPO_4$, 1% SDS, and 1 mM EDTA at 60 to 68° C. (preferably 65° C. and more preferably 68° C.)

Other examples include the following method. First, prehybridization is carried out overnight at 42° C. in a hybridization solution containing 25% formamide (50% formamide under more severe conditions), 4×SSC (sodium chloride/sodium citrate), 50 mM Hepes (pH 7.0), 10×Denhardt's solution, and 20 μg/mL of denatured salmon sperm DNA. Thereafter, labeled probes are added, and incubation is carried out overnight at 42° C. to hybridize the two kinds of polynucleotides.

Next, washing is carried out under any of the following conditions. Normal condition; 1×SSC and 0.1% SDS are used as washing liquids for washing at about 37° C. Severe condition; 0.5×SSC and 0.1% SDS are used as washing liquids for washing at about 42° C. More severe condition; 0.2×SSC and 0.1% SDS are used as washing liquids for washing at about 65° C.

As the washing conditions for hybridization become more severe, the specificity of hybridization becomes higher. Note that the above combination of conditions SSC, SDS, and temperature is merely illustrative. Stringency similar to the above can be achieved by appropriately combining the above-mentioned elements for determining the stringency of hybridization or other elements (for example, probe concentration, probe length, and hybridization reaction time). This is described in, for example, [Joseph Sambrook & David W. Russell, Molecular cloning: a laboratory manual 3rd Ed., New York: Cold Spring Harbor Laboratory Press, 2001].

Expression Vector Containing Polynucleotide Encoding Cas Protein Group

In the present invention, it is possible to use an expression vector for expressing the Cas protein group. Regarding the expression vector, various types of commonly used vectors can be used as a base vector, and it can be appropriately selected depending on the cells for introduction or the introduction method. Specific examples usable include plasmids, phages, cosmids, and the like. The specific type of the vector is not particularly limited, and it suffices to appropriately select a vector which can be expressed in the host cell.

Examples of the expression vectors described above include phage vectors, plasmid vectors, viral vectors, retroviral vectors, chromosome vectors, episomal vectors, virus-derived vectors (bacterial plasmids, bacteriophages, yeast episomes, and the like), yeast chromosomal elements and viruses (baculoviruses, papova viruses, vaccinia viruses, adenoviruses, tripox viruses, pseudorabies viruses, herpes viruses, lentiviruses, retroviruses, and the like), and vectors derived from combinations thereof (cosmids, phagemids, and the like).

Preferably, the expression vector further contains a site for transcription initiation and transcription termination as well as a ribosome binding site in the transcription region. The coding site of the mature transcript in the vector will contain the transcription initiation codon AUG at the beginning and an appropriately located termination codon at the end of the polypeptide to be translated.

In the present invention, the expression vector for expressing the Cas protein group may contain a promoter sequence. The above promoter sequence may be appropriately selected depending on the type of eukaryotic cell serving as a host. In addition, the expression vector may contain a sequence for enhancing transcription from DNA, for example an enhancer sequence. Examples of enhancers include the SV40 enhancer (which is arranged at 100-270 bp downstream of the replication origin), the early promoter enhancer of the cytomegalovirus, and the polyoma enhancer and the adenovirus enhancer arranged downstream of the replication origin. Additionally, the expression vector may contain a sequence for stabilizing a transcribed RNA, for example a poly(A) addition sequence (polyadenylation sequence, polyA). Examples of poly(A) addition sequences include poly(A) addition sequences derived from the growth hormone gene, poly(A) addition sequences derived from the bovine growth hormone gene, poly(A) addition sequences derived from the human growth hormone gene, poly(A)

addition sequences from the SV40 virus, and poly(A) additional sequences derived from the human or rabbit β-globin gene.

The number of polynucleotides encoding the Cas protein group to be incorporated into the same vector is not particularly limited as long as it is possible to exhibit the functions of the CRISPR-Cas systems in the host cell into which the expression vector has been introduced. For example, it is possible to make such a design that the polynucleotide encoding the Cas protein group is mounted on vectors of one type (of the same type). Furthermore, it is also possible to make such a design that all or some of the polynucleotide encoding the Cas protein groups is mounted on separate vectors. For example, it is possible to make such a design that the polynucleotide encoding Cascade proteins is mounted on vectors of one type (of the same type) and the polynucleotide encoding Cas3 is mounted on other vectors. It is preferable to use a method for mounting the polynucleotide encoding Cas protein groups on six different types of vectors from the viewpoint of expression efficiency and the like.

Otherwise, multiple polynucleotides encoding the same proteins may be mounted on the same vectors for the purpose of controlling the expression level and the like. For example, it is possible to make such a design that the polynucleotides encoding Cas3 are arranged at two sites of vectors of one type (of the same type).

Figure 8:
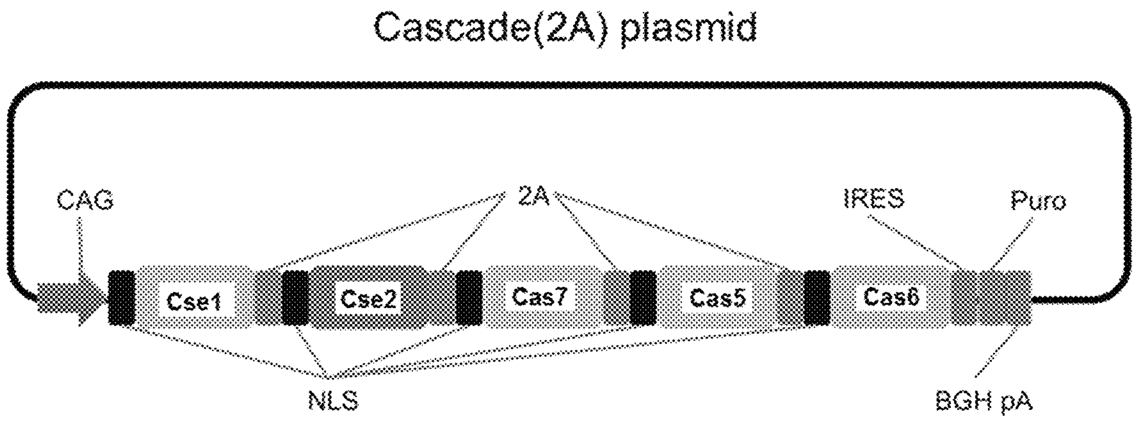
FIG. 8 is a schematic diagram showing the structure of a Cascade (2A) plasmid.

In addition, it is possible to use an expression vector which contains multiple nucleic acid sequences encoding the Cas protein group and which has nucleic acid sequences that are inserted between those multiple nucleic acid sequences and that encode amino acid sequences (2A peptides and the like) to be cleaved by intracellular proteases (for example, see the vector structure of FIG. 8). When polynucleotides having such nucleic acid sequences are transcribed and translated, polypeptide strands linked in the cell are expressed. Subsequently, due to the action of intracellular proteases, the Cas protein groups are separated, become separate proteins, and then form complexes to function. This makes it possible to regulate the amount ratio of Cas protein groups expressed intracellularly. For example, it is predicted that Cas3 and Cse1 (Cas8) will be expressed in equal amounts from an "expression vector containing one nucleic acid sequence encoding Cas3 and one nucleic acid sequence encoding Cse1 (Cas8)." In addition, it is possible to express multiple Cas protein groups with one type of expression vector, which is advantageous in excellence of handling property. On the other hand, the embodiment is usually superior in which the Cas protein groups are expressed by different expression vectors from the viewpoint of high DNA cleavage activity.

It is possible to prepare the expression vectors used in the present invention by known methods. Examples of such methods include the method described in the manual attached to a kit for preparing vectors as well as methods described in various handbooks. An example of a comprehensive handbook is [Joseph Sambrook & David W. Russell, Molecular cloning: a laboratory manual 3rd Ed., New York: Cold Spring Harbor Laboratory Press, 2001].

Expression Vector Containing crRNA, Polynucleotide Encoding the crRNA, or the Polynucleotide The CRISPR-Cas3 system of the present invention includes a crRNA, a polynucleotide encoding the crRNA, or an expression vector containing the polynucleotide for the purpose of targeting to DNA for genome editing.

The crRNA is an RNA which forms part of the CRISPR-Cas system and has a nucleic acid sequence complementary to the target sequence. The CRISPR-Cas3 system of the present invention makes it possible with a crRNA to specifically recognize a target sequence and cleave the sequence. In CRISPR-Cas systems typified by the CRISPR-Cas9 system, mature crRNAs have been usually used as cRNAs. However, although the reason is not clear, it was found that use of a mature crRNA is not suitable when the CRISPR-Cas3 system is made to function in eukaryotic cells. Moreover, it was surprisingly found that it is possible to highly efficiently perform genome editing in eukaryotic cells by using a pre-crRNA instead of a mature crRNA. This fact is apparent from a comparative experiment between a mature crRNA and pre-crRNAs (FIG. 10). Therefore, it is particularly preferable to use pre-crRNAs as the crRNAs of the present invention.

The pre-crRNAs used in the present invention typically have the structures of "leader sequence-repeated sequence-spacer sequence-repeated sequence (LRSR structure)" and "repeated sequence-spacer sequence-repeated sequence (RSR structure)." The leader sequence is an AT-rich sequence and functions as a promoter to express a pre-crRNA. The repeated sequence is a sequence repeating with a spacer sequence in between, and the spacer sequence is a sequence designed in the present invention as a sequence complementary to the target DNA (originally it is a sequence derived from a foreign DNA incorporated in the course of adaptation). The pre-crRNA becomes a mature crRNA when cleaved by proteins constituting the Cascade (for example, Cas6 for types I-A, B, and D to E and Cas5 for type I-C).

Typically, the strand length of a leader sequence is 86 bases, and the strand length of a repeated sequence is 29 bases. The strand length of a spacer sequence is, for example, 10 to 60 bases, preferably 20 to 50 bases, more preferably 25 to 40 bases, and typically 32 to 37 bases. Thus, in the case of the LRSR structure, the pre-crRNA used in the present invention has a strand length of, for example, 154 to 204 bases, preferably 164 to 194 bases, more preferably 169 to 184 bases, and typically 176 to 181 bases. In addition, in the case of the RSR structure, the strand length is, for example, 68 to 118 bases, preferably 78 to 108 bases, more preferably 83 to 98 bases, and typically 90 to 95 bases.

In order to make the CRISPR-Cas3 system of the present invention function in eukaryotic cells, it is considered that the process is important by which the repeated sequences of a pre-crRNA are cleaved by the proteins constituting the Cascade. Thus, it should be understood that the above repeated sequences may be shorter or longer than the above strand length as long as such cleavage takes place. Specifically, it can be said that the pre-crRNA is a crRNA formed by adding sequences sufficient for cleavage by proteins constituting the Cascade to both ends of the mature crRNA described below. In this way, a preferred embodiment of the method of the present invention includes the step of cleaving a crRNA with proteins constituting the Cascade after introducing the CRISPR-Cas3 system into eukaryotic cells.

On the other hand, the mature crRNA generated by cleavage of a pre-crRNA has a structure of "5'-handle sequence-spacer sequence-3'-handle sequence." Typically, the 5'-handle sequence is composed of 8 bases from positions 22 to 29 of the repeated sequence and is held in Cas5. In addition, the 3'-handle sequence is typically composed of 21 bases from positions 1 to 21 in the repeated sequence, forms a stem loop structure with the bases of positions 6 to 21, and is held at Cas6. Thus, the strand length of a mature crRNA is usually 61 to 66 bases. Note that, since there are also mature crRNAs having no 3'-handle sequence depending on the type of the CRISPR-Cas3 system, the strand length is shortened by 21 bases in this case.

Note that the sequence of an RNA may be appropriately designed according to the target sequence for which DNA editing is desired. In addition, it is possible to synthesize an RNA using any method known in the art.

Eukaryotic Cell

Examples of "eukaryotic cells" in the present invention include animal cells, plant cells, algae cells, and fungal cells. In addition, examples of animal cells include mammalian cells as well as cells of, for example, fish, birds, reptiles, amphibians, and insects.

Examples of the "animal cells" include cells constituting animal bodies, cells constituting organs/tissues excised from animals, and cultured cells derived from animal tissues. Specific examples include germ cells such as oocytes and sperm; embryonic cells of embryos at various stages (such as 1-cell embryos, 2-cell embryos, 4-cell embryos, 8-cell embryos, 16-cell embryos, and morula embryos); stem cells such as induced pluripotent stem (iPS) cells and embryonic stem (ES) cells; and somatic cells such as fibroblasts, hematopoietic cells, neurons, muscle cells, bone cells, liver cells, pancreatic cells, brain cells, and kidney cells. It is possible to use oocytes before fertilization and after fertilization as the oocytes used for preparing genome-edited animals, preferably oocytes after fertilization, that is, fertilized eggs. Particularly preferably, the fertilized eggs are from pronuclear stage embryos. Oocytes can be thawed and used after freezing.

In the present invention, "mammalian" is a concept including human and non-human mammals. Examples of non-human mammals include cloven-hoofed mammals such as cattle, boars, pigs, sheep, and goats, odd-toed mammals such as horses, rodents such as mice, rats, guinea pigs, hamsters, and squirrels, lagomorphs such as rabbits, and carnivores such as dogs, cats, and ferrets. The non-human mammals described above may be livestock or companion animals (pets), or may be wild animals.

Examples of the "plant cells" include cells of cereals, oil crops, feed crops, fruits, and vegetables. Examples of the "plant cells" include cells constituting plant bodies, cells constituting organs and tissues separated from plants, and cultured cells derived from plant tissues. Examples of organs and tissues of plants include leaves, stems, shoot apexes (growing points), roots, tubers, and calli. Examples of plants include rice, corn, banana, peanut, sunflower, tomato, oilseed rape, tobacco, wheat, barley, potato, soybean, cotton, and carnation as well as propagation materials thereof (for example, seeds, tuberous roots, and tubers).

DNA Editing

In the present invention, "editing the DNA of a eukaryotic cell" may be a step in which the DNA of a eukaryotic cell is edited in vivo or in vitro. In addition, "editing the DNA" means the operations exemplified by the following types (including combinations thereof).

Note that, in the present specification, the DNA used in the above context includes not only DNA present in the nucleus of a cell but also exogenous DNA and DNA present other than the nucleus of a cell such as mitochondrial DNA.

1. cleaving the DNA strand at the target site
2. deleting a base of the DNA strand at the target site
3. inserting abase into the DNA strand at the target site
4. replacing a base of the DNA strand at the target site
5. modifying a base of the DNA strand at the target site
6. modulating the transcription of the DNA (gene) at the target site.

One embodiment of the CRISPR-Cas3 system of the present invention uses a protein having an enzymatic activity for modifying the target DNA by a method other than introducing DNA cleavage. This embodiment can be achieved by, for example, fusing Cas3 or Cascade with a heterologous protein having a desired enzymatic activity into a chimeric protein. Thus, "Cas3" and "Cascade" in the present invention also include such fusion proteins. Examples of the enzymatic activity of the protein to be fused include, but not limited to, deaminase activity (for example, cytidine deaminase activity and adenosine deaminase activity), methyl transferase activity, demethylation enzyme activity, DNA repair activity, DNA damage activity, dismutase activity, alkylation activity, depurination activity, oxidation activity, pyrimidine dimer formation activity, integrase activity, transposase activity, recombinase activity, polymerase activity, ligase activity, photoreactivation enzyme activity, and glycosylase activity. In this case, the nuclease activity or the helicase activity of Cas3 is not necessarily required. For this reason, it is possible to use as Cas3 a mutant in which some or all of these activities are deleted (for example, a mutant of D domain H74A (dnCas3), a mutant of K320N of SF2 domain motif 1 (dhCas3), and a double mutant of S483A/T485A of SF2 domain motif 3 (dh2Cas3)). Precise genome editing is possible by replacing bases without causing large deletion at the target site if, for example, a fusion protein of a deaminase and a mutant in which some or all of the nuclease activities of Cas3 have been eliminated is used as a constituent element of the CRISPR-Cas3 system of the present invention. The method for applying a deaminase to the CRISPR-Cas systems is well known (Nishida K. et al., Targeted nucleotide editing using hybrid prokaryotic and vertebrate adaptive immune systems, Science, DOI: 10.1126/science.aaf8729, (2016)), and it suffices to apply the method to the CRISPR-Cas3 system of the present invention.

Another embodiment of the CRISPR-Cas3 system of the present invention regulates gene transcription at the binding site of the present system without DNA cleavage. This embodiment can be achieved by, for example, fusing Cas3 or Cascade with the desired transcription regulating protein into a chimeric protein. Thus, "Cas3" and "Cascade" in the present invention also include such fusion proteins. Examples of the transcription regulating protein include, but not limited to, light inducible transcriptional regulators, small molecule/drug responsive transcriptional regulators, transcription factors, and transcriptional repressors. In this case, the nuclease activity or the helicase activity of Cas3 is not necessarily required. For this reason, it is possible to use as Cas3 a mutant in which some or all of these activities are deleted (for example, a mutant of D domain H74A (dnCas3), a mutant of K320N of SF2 domain motif 1 (dhCas3), and a double mutant of S483A/T485A of SF2 domain motif 3 (dh2Cas3)). Methods for applying a transcription regulating protein to the CRISPR-Cas systems are known to those skilled in the art.

Additionally, in the CRISPR-Cas3 system of the present invention, consider the case of, for example, using a mutant in which some or all of the nuclease activities of Cas3 are deleted. Proteins having other nuclease activities may be fused with Cas3 or Cascade. Such embodiment is included in the present invention.

Besides, in the CRISPR-Cas3 system of the present invention, consider the case of using a mutant in which some or all of the nuclease activities of Cas3 are deleted and using the activities of other proteins in editing DNA. The "DNA cleavage activity" in the present specification is appropriately interpreted as various activities which those proteins have.

Moreover, DNA editing may be performed on DNA contained in a specific cell within an individual. Such DNA editing can be performed on, for example, a specific cell as a target among cells constituting the body of an animal or plant.

No limitation is imposed on the method for introducing the molecules constituting the CRISPR-Cas3 system of the present invention into eukaryotic cells in the form of a polynucleotide or an expression vector containing the polynucleotide. Examples of the method include electroporation, the calcium phosphate method, the liposome method, the DEAE dextran method, the microinjection method, cationic lipid mediated transfection, electroporation, transduction, and infection using virus vectors. Such methods are described in many standard laboratory manuals such as "Leonard G. Davis et al., Basic methods in molecular biology, New York: Elsevier, 1986."

No limitation is imposed on the method for introducing the molecules of the CRISPR-Cas3 system of the present invention into eukaryotic cells in the form of a protein. Examples thereof include electroporation, cationic lipid mediated transfection, and microinjection.

The DNA editing according to the present invention can be applied to various fields. Application examples include gene therapy, breed improvement, production of transgenic animals or cells, production of useful substances, and life science research.

Known methods can be used as methods for preparing non-human individuals from cells. Germ cells or pluripotent stem cells are usually used in the case of producing non-human individuals from cells of animals. For example, molecules constituting the CRISPR-Cas3 system of the present invention are introduced into an oocyte. The obtained oocyte is then transplanted into the uterus of a female non-human mammal which has been placed in a pseudopregnant state. After that, a litter is obtained. The transplantation can be carried out in a fertilized egg of 1-cell embryo, 2-cell embryo, 4-cell embryo, 8-cell embryo, 16-cell embryo, or morula embryo. If desired, the oocyte can be cultured under suitable conditions until transplantation. Transplantation and culture of the oocyte can be carried out based on a conventionally known method (Nagy A. et al., Manipulating the Mouse Embryo, Cold Spring Harbour, New York: Cold Spring Harbour Laboratory Press, 2003). It is also possible to obtain, from the obtained non-human individual, clones or descendants in which the desired DNA has been edited.

In addition, it has long been known that somatic cells of plants possess differentiation totipotency, and methods for regenerating plants from plant cells of various plants have been established. Therefore, it is possible to obtain a plant in which the desired DNA is knocked in by introducing the molecules constituting the CRISPR-Cas3 system of the present invention into plant cells and regenerating plants from the obtained plant cells. It is also possible to obtain progeny, clones, or propagation materials in which the desired DNA has been edited. As a method of redifferentiating a plant tissue by tissue culture to obtain an individual, it is possible to use a method established in the present technical field (Protocols for Plant Transformation, edited by TABEI Yutaka, Kagaku-Dojin, pp. 340-347 (2012)).

[2] Kit Used in CRISPR-Cas3 System

A kit used in the CRISPR-Cas3 system of the present invention comprises the following (A) and (B).

(A) a Cas3 protein, a polynucleotide encoding the protein, or an expression vector containing the polynucleotide, and (B) a Cascade protein, a polynucleotide encoding the protein, or an expression vector containing the polynucleotide.

The kit may further comprises a crRNA, a polynucleotide encoding the crRNA, or an expression vector containing the polynucleotide The constituent elements of the kit of the present invention may be in an embodiment in which all or some of them are mixed, or may be in an embodiment in which each of them is independent.

It is possible to use the kit of the present invention in fields such as pharmaceutical preparations, food, animal husbandry, fishery, industry, bioengineering, and life science research.

Hereinafter, the kit of the present invention is described assuming pharmaceutical preparations (drugs). Note that, in the case of using the above-described kit in fields such as animal husbandry, bioengineering, and life science research, the kit can be used by appropriately interpreting the following explanation based on common technical knowledge in those fields.

It is possible to prepare a pharmaceutical preparation for editing DNA of animal cells including humans by usual methods using the CRISPR-Cas3 system of the present invention. More specifically, the pharmaceutical preparation can be prepared by formulating the molecules constituting the CRISPR-Cas3 system of the present invention with, for example, a pharmaceutical preparation additive.

Here, the "pharmaceutical preparation additive" means a substance other than the active ingredients contained in the pharmaceutical preparation. The pharmaceutical preparation additive is a substance contained in a pharmaceutical preparation for the purpose of facilitating formulation, stabilizing the quality, enhancing the utility, and the like. Examples of the pharmaceutical preparation additive described above can include excipients, binders, disintegrants, lubricants, fluidizers (solid antistatic agents), colorants, capsule coats, coating agents, plasticizers, taste-making agents, sweeteners, flavoring agents, solvents, dissolution assisting agents, emulsifiers, suspending agents (pressure sensitive adhesives), thickeners, pH adjusters (acidifiers, alkalizers, and buffers), humectants (solubilizers), antibacterial preservatives, chelating agents, suppository bases, ointment bases, curing agents, softeners, medical water, propellants, stabilizers, and preservatives. These pharmaceutical preparation additives can readily be selected by those skilled in the art according to the intended dosage form and route of administration as well as standard pharmaceutical practice.

In addition, the pharmaceutical preparation for editing DNA of animal cells using the CRISPR-Cas3 system of the present invention may contain additional active ingredients. The additional active ingredients are not particularly limited and can be appropriately designed by those skilled in the art.

Specific examples of the active ingredients and pharmaceutical preparation additives described above can be learned according to the standards established by, for example, the US Food and Drug Administration (FDA), the European Medicines Authority (EMA), the Japanese Ministry of Health, Labor and Welfare.

Examples of methods for delivering a pharmaceutical preparation to the desired cells include methods using virus vectors targeting the cells (adenovirus vectors, adeno-associated virus vectors, lentivirus vectors, Sendai virus vectors, and the like) or antibodies specifically recognizing the cells. The pharmaceutical preparation can take any dosage form depending on the purpose. Also, the above pharmaceutical preparation is properly prescribed by doctors or medical professionals.

The kit of the present invention preferably further includes an instruction manual.

EXAMPLES

Hereinafter, the present invention is described in more detail with reference to Examples, but the present invention is not limited only to the following examples.

A. Establishment of CRISPR-Cas3 System in Eukaryotic Cell

Material and Method

[1] Preparation of Reporter Vectors Containing Target Sequences

The target sequences were the sequence derived from the human CCR5 gene (SEQ ID NO: 19) and the spacer sequence of *E. coli* CRISPR (SEQ ID NO: 22).

For the purpose of inserting the target sequences into the vectors, a synthetic polynucleotide (SEQ ID NO: 20) containing the target sequence derived from the human CCR5 gene (SEQ ID NO: 19) and a synthetic polynucleotide (SEQ ID NO: 21) containing a sequence complementary to the above target sequence (SEQ ID NO: 19) were prepared. Similarly, a synthetic polynucleotide (SEQ ID NO: 23) containing the target sequence derived from the spacer sequence of *E. coli* CRISPR (SEQ ID NO: 22) and a synthetic polynucleotide (SEQ ID NO: 24) containing a sequence complementary to the above target sequence (SEQ ID NO: 22) were prepared. All of the above synthetic polynucleotides were obtained from Hokkaido System Science Co., Ltd.

The above polynucleotides were inserted into the reporter vectors by the method described in [Sakuma T et al. (2013) Efficient TALEN construction and evaluation methods for human cell and animal applications, Genes to Cells, Vol. 18 (Issue 4), pp. 315-326]. The outline is as follows. First, polynucleotides having sequences complementary to each other (the polynucleotide of SEQ ID NO: 20 and the polynucleotide of SEQ ID NO: 21; the polynucleotide of SEQ ID NO: 23 and the polynucleotide of SEQ ID NO: 24) were heated at 95° C. for 5 minutes, and then cooled to room temperature and hybridized. A block incubator (BI-515A, Astec) was used for the above step. Next, the polynucleotide hybridized to form a double-stranded structure was inserted into the base vector to prepare a reporter vector.

Figure 4:
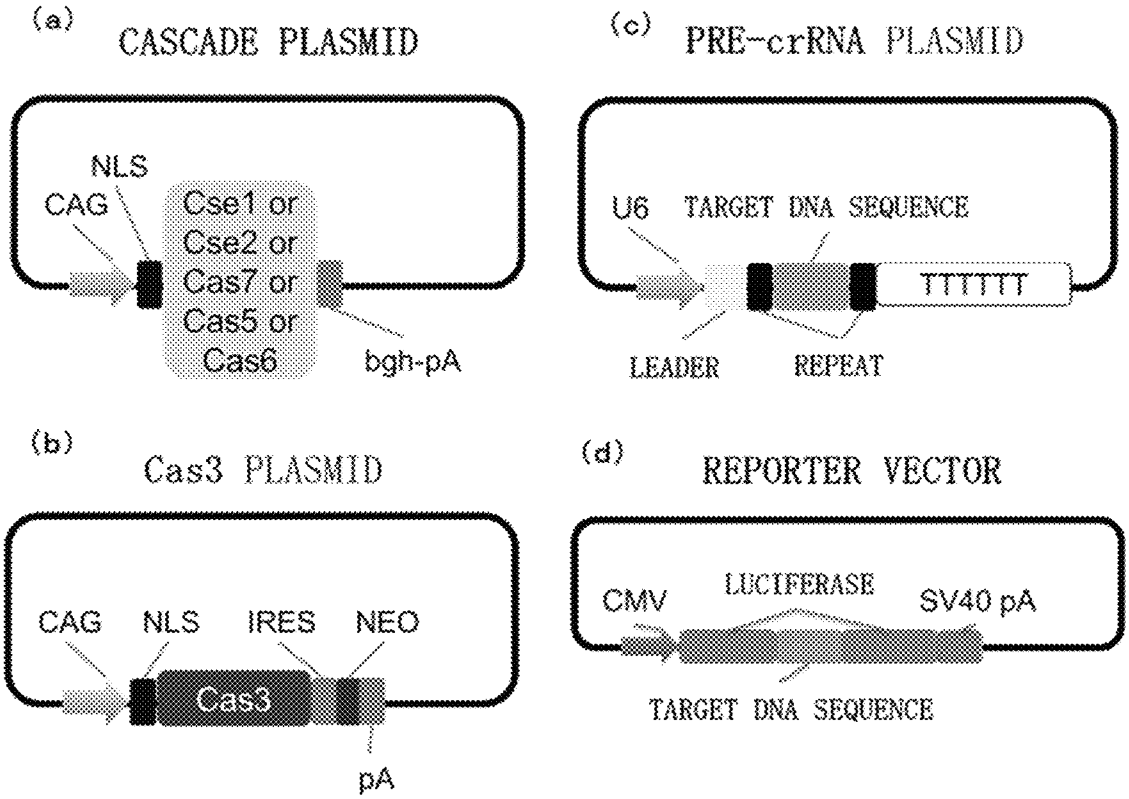
FIG. 4(*a*) is a schematic diagram showing the structure of a Cascade plasmid.

The sequences of the prepared reporter vectors are shown at SEQ ID NO: 31 (reporter vector containing the target sequence derived from the human CCR5 gene) and SEQ ID NO: 32 (reporter vector containing the target sequence derived from the spacer sequence of *E. coli* CRISPR). In addition, the structure of reporter vector is shown in FIG. 4(*d*).

[2] Preparation of Cse1 (Cas8), Cse2 (Cas11), Cas5, Cas6, Cas7, and crRNA Expression Vectors

Amplification and Preparation of Inserts

Consider polynucleotides having modified nucleic acid sequences encoding Cse1 (Cas8), Cse2 (Cas11), Cas5, Cas6, and Cas7 (with SEQ ID NO: 2, SEQ ID NO: 3, SEQ ID NO: 4, SEQ ID NO: 5, and SEQ ID NO: 6, respectively). First, production of polynucleotides linked in the order of SEQ ID NO: 2-SEQ ID NO: 3-SEQ ID NO: 6-SEQ ID NO: 4-SEQ ID NO: 5 (polynucleotides having linked nucleic acid sequences for encoding Cse1 (Cas8)-Cse2 (Cas11)-Cas7-Cas5-Cas6 in this order) was outsourced to GenScript Corporation for purchase. The nucleic acid sequences encoding the proteins of Cse1 (Cas8)-Cse2 (Cas11)-Cas7-Cas5-Cas6 were linked with 2A peptides (amino acid sequence: GSGATNFSLLKQAGDVEENPGP (SEQ ID NO: 58)).

Note that the nucleic acid sequences encoding the 2A peptides were slightly different depending on the Cas protein linkage sites and were as follows. The sequence between Cse1 (Cas8) and Cse2 (Cas11): GGAAGCGGAGCAACCAACTTCAGCCTGCTGAAGCAGGCCGGCGATGTGGAGGA GAATCCAGGCCCC (SEQ ID NO: 59). The sequence between Cse2 (Cas11) and Cas7: GGCTCCGGCGCCACCAATTTTTCTCTGCTGAAGCAGGCAGGCGATGTGGAGGA GAACCCAGGACCT (SEQ ID NO: 60). The sequence between Cas7 and Cas5: GGATCTGGAGCCACCAATTTCAGCCTGCTGAAGCAAGCAGGCGACGTGGAAGA AAACCCAGGACCA (SEQ ID NO: 61). The sequence between Cas5 and Cas6: GGATCTGGGGCTACTAATTTTTCTCTGCTGAAGCAAGCCGGCGACGTGGAAGA GAATCCAGGACCG (SEQ ID NO: 62).

Next, each of the polynucleotides was amplified under the PCR conditions (primer and time course) in the following table. For PCR, 2720 Thermal cycler (applied biosystems) was used.

TABLE 1

| Primer | Sequence | Timecourse |
|---|---|---|
| Cse1-U | GCAAAGAATTCAGATCTCCACCATGCCTAAGAAGAAGAGAAAAGTGAACCTGCTGATTGAC (SEQ ID NO: 36) | 98° C. (10 Sec) → 68° C. (1 Min) 35 Cycles |
| Cse1-L | TCATCGATGCATCTCGAGTTATCCATTAGAAGGTCCTCCCTGTGGCTTC (SEQ ID NO: 37) | |
| Cse2-U | GCAAAGAATTCAGATCTCCACCATGCCCAAGAAGAAGCGGAAGGTGGCCGATGAGATCGAC (SEQ ID NO: 38) | 98° C. (10 Sec) → 68° C. (1 Min) 35 Cycles |
| Cse2-L | TCATCGATGCATCTCGAGTTAGGCGTTCTTATTTGTGGTCAGCACGAAG (SEQ ID NO: 39) | |
| Cas5-U | GCAAAGAATTCAGATCTCCACCATGCCCAA | |

TABLE 1-continued

| Primer | Sequence | Timecourse |
|---|---|---|
| | GAAGAAGCGGAAGGT GTCCAATTTCATCAA C (SEQ ID NO: 40) | |
| Cas5-L | TCATCGATGCATCTC GAGTTATGCCTCTCC ATTGTTCCGCACCCA GCTC (SEQ ID NO: 41) | |
| Cas6-U | GCAAAGAATTCAGAT CTCCACCATGCCCAA GAAGAAGCGGAAAGT GTACCTGAGCAAAGT G (SEQ ID NO: 42) | |
| Cas6-L | TCATCGATGCATCTC GAGTTACAGAGGTGC CAGTGACAGCAGCCC AC (SEQ ID NO: 43) | |
| Cas7-U | GCAAAGAATTCAGAT CTCCACCATGCCCAA GAAGAAGCGGAAGGT GCGCTCCTACCTGAT C (SEQ ID NO: 44) | 98° C. (10 Sec) → 68° C. (1 Min 40 Sec) 35 Cycles |
| Cas7-L | TCATCGATGCATCTC GAGTTACTGGCTCAC GTCCATTCCTCCCTT GATC (SEQ ID NO: 45) | |

Polynucleotides having the following complementary sequences were obtained as polynucleotides having nucleic acid sequences for expressing crRNA.

1. polynucleotides for expressing crRNA corresponding to the sequence derived from the human CCR5 gene (SEQ ID NOs: 25 and 26, obtained from Hokkaido System Science Co., Ltd.)
2. polynucleotides for expressing crRNA corresponding to the spacer sequence of *E. coli* CRISPR (SEQ ID NOs: 27 and 28, obtained from Hokkaido System Science Co., Ltd.)
3. polynucleotides for expressing crRNA corresponding to the sequence derived from the human EMX1 gene (SEQ ID NOs: 29 and 30, obtained from Pharmac).

Ligation and Transformation

As a substrate plasmid, pPB-CAG-EBNXN (supplied from Sanger Center) was used. In NEB buffer, 1.6 μg of the substrate plasmid, 1 μl of restriction enzyme BglII (New England Biolabs), and 0.5 μl of XhoI (New England Biolabs) were mixed and reacted at 37° C. for 2 hours. The cleaved substrate plasmids were purified with Gel extraction kit (Qiagen).

The substrate plasmids thus prepared and the above inserts were ligated with a Gibson Assembly system. Ligation was carried out in accordance with the protocol of the Gibson Assembly system with the ratio of the substrate plasmids to the inserts being 1:1 (at 50° C. for 25 minutes, total volume of the reaction solution: 8 μL).

Subsequently, 6 μL of a solution of the plasmids obtained above (ligation reaction solution) and competent cells (prepared by Takeda Laboratory) were used to perform transformation in accordance with the usual method.

Thereafter, plasmid vectors were purified from the transformed *E. coli* by the alkaline prep method. Briefly, the plasmid vectors were recovered using QIAprep Spin Miniprep Kit (Qiagen), and the recovered plasmid vectors were purified by the ethanol precipitation method and then adjusted to have a concentration of 1 μg/μL in a TE buffer solution.

The structure of each plasmid vector is shown in FIGS. 4(*a*) to 4(*c*). In addition, the nucleic acid sequences of pre-crRNA expression vectors are shown at SEQ ID NO: 33 (expression vector for expressing crRNA corresponding to the sequence derived from the human CCR5 gene), SEQ ID NO: 34 (expression vector for expressing crRNA corresponding to the spacer sequence of *E. coli* CRISPR), and SEQ ID NO: 35(expression vector for expressing crRNA corresponding to the sequence derived from the human EMX1 gene).

[3] Preparation of Cas3 Expression Vector

A polynucleotide having a modified nucleic acid sequence encoding Cas3 (SEQ ID NO: 1) was obtained from Genscript. Specifically, pUC57 vector incorporating the polynucleotide described above was obtained from Genscript.

The above vector was cleaved with restriction enzyme NotI. Next, 2 U of Klenow Fragment (Takara Bio Inc.) and 1 μL of 2.5 mM dNTP Mixture (Takara Bio Inc.) were used to smooth the edge of the fragment. Thereafter, the above fragment was purified using Gel extraction (Qiagen). The purified fragment was further cleaved with restriction enzyme XhoI and purified using Gel extraction (Qiagen).

The purified fragment was ligated using a substrate plasmid (pTL2-CAG-IRES-NEO vector, prepared by Takeda Laboratory) and a ligation kit (Mighty Mix, Takara Bio Inc.). After that, transformation and purification were carried out by the same operations as in [2]. The recovered plasmid vector was prepared to have a concentration of 1 μg/μL in a TE buffer solution.

[4] Preparation of Plasmid Vector Containing BPNLS

Figure 7:
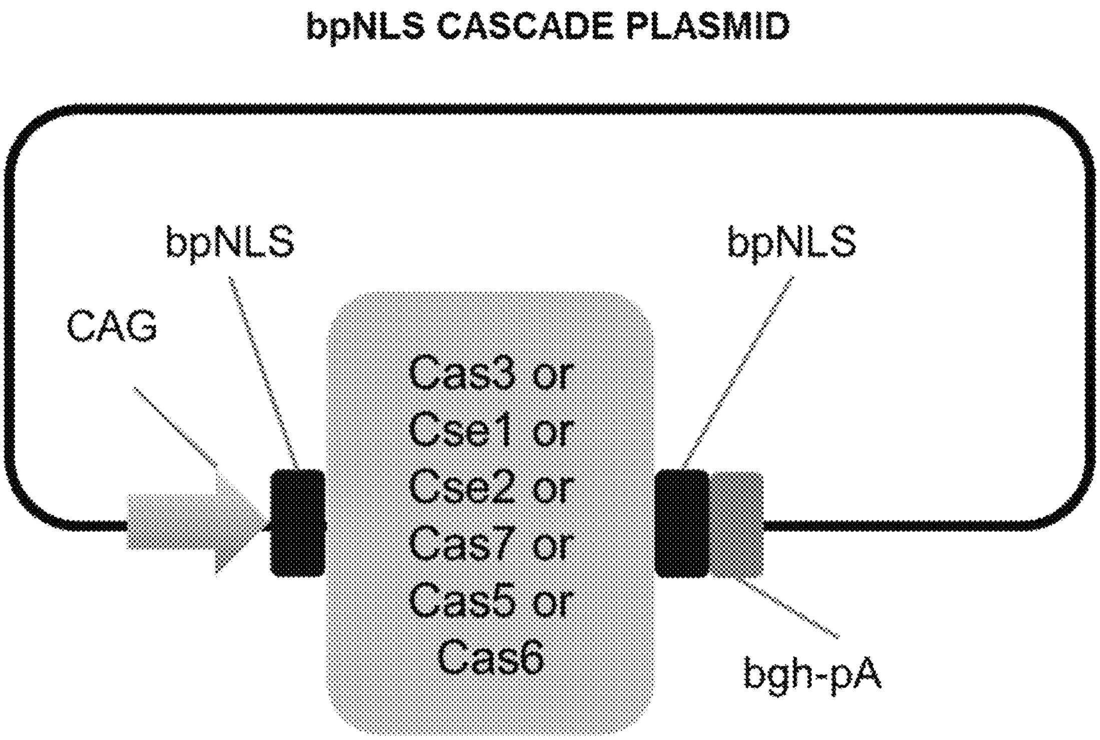
FIG. 7 is a schematic diagram showing the structure of a Cas3/Cascade plasmid added with bpNLSs.

Prepared were Cas3, Cse1 (Cas8), Cse2 (Cas11), Cas5, Cas6, and Cas7 expression vectors in which BPNLSs were connected to the 5'-end and the 3'-end (see FIG. 7).

The production of an insert for each Cas protein group containing BPNLSs at both ends was ordered to Thermo Fisher Scientific. The specific sequence of the above insert is (AGATCTTAATACGACTCACTATAGG-GAGAGCCGCCACCATGGCC: SEQ ID NO: 56)-(any one of SEQ ID NOs: 7 to 12)-(TAATATCCTCGAG: SEQ ID NO: 57). SEQ ID NO: 56 is a sequence provided with a cleavage site by BglII. SEQ ID NO: 57 is a sequence provided with a cleavage site by XhoI.

The pMK vector incorporating the above sequence was cleaved with restriction enzymes BglII and XhoI and purified using Gel extraction (Qiagen). The purified fragment was ligated using a substrate plasmid (pPB-CAG-EBNXN, supplied from Sanger Center) and a ligation kit (Mighty Mix, Takara Bio Inc.). After that, transformation and purification were carried out by the same operations as in [2]. The recovered plasmid vector was prepared to have a concentration of 1 μg/μL in a TE buffer solution.

[5] Preparation of Plasmid Vector Containing Cascade (2A)

Prepared was an expression vector in which the nucleic acid sequence had Cse1 (Cas8), Cse2 (Cas11), Cas7, Cas5, and Cas6 linked in this order. More specifically, prepared was an expression vector having an arrangement of (NLS-Cse1 (Cas8): SEQ ID NO: 2)-2A-(NLS-Cse2 (Cas11): SEQ ID NO: 3)-2A-(NLS-Cas7: SEQ ID NO: 6)-2A-(NLS-Cas5: SEQ ID NO: 4)-2A-(NLS-Cas6: SEQ ID NO: 5) (see FIG. 8). Note that the amino acid sequence of NLS is PKKKRKV (SEQ ID NO: 52), and the nucleic acid sequence is CCCAAGAAGAAGCGGAAGGTG (SEQ ID NO: 53). In addition, the amino acid sequence of 2A peptide is GSGATNFSLLKQAGDVEENPGP (SEQ ID NO: 58) (the corresponding nucleic acid sequences are SEQ ID NOs: 59 to 62).

A polypeptide having the above nucleic acid sequence was obtained from GenScript. The pUC57 vector incorporating the above sequence was cleaved with restriction enzyme EcoRI-HF and purified using Gel extraction (Qiagen). The purified fragment was ligated using a substrate plasmid (pTL2-CAG-IRES-Puro vector, prepared by Takeda Laboratory) and a ligation kit (Mighty Mix, Takara Bio Inc.). After that, transformation and purification were carried out by the same operations as in [2]. The recovered plasmid vector was prepared to have a concentration of 1 μg/μL in a TE buffer solution.

Example A-1

The cleavage activity of the target sequence of the exogenous DNA was evaluated as follows. A crRNA and Cas3, Cse1 (Cas8), Cse2 (Cas11), Cas5, Cas6, and Cas7 added with nuclear localization signals to have a modified nucleic acid sequence were expressed in HEK (human embryonic kidney) 293T cells.

Prior to transfection, the HEK 293T cells were cultured in a 10 cm dish. Culture of the HEK 293T cells was carried out in EF medium (GIBCO) at 37° C. in a 5% $CO_2$ atmosphere. The density of HEK 293T cells in the EF medium was adjusted to $3\times10^4$/100 μL.

In addition, 100 ng of the above reporter vector; 200 ng of each of the Cas3 plasmid, the Cse1 (Cas8) plasmid, the Cse2 (Cas11) plasmid, the Cas5 plasmid, the Cas6 plasmid, the Cas7 plasmid, and the crRNA plasmid; 60 ng of pRL-TK vector (capable of expressing Renilla luciferase, Promega); and 300 ng of pBluecscript II KS(+) vector (Agilent Technologies) were mixed in 25 μL of Opti-MEM (Thermo Fisher Scientific). The conditions using the reporter vector having the target sequence derived from CCR5 as the reporter vector correspond to 1 in FIG. 1, and the conditions using the reporter vector having the spacer sequence of *E. coli* CRISPR correspond to 10 in FIG. 1.

Next, 1.5 μL of Lipofectamine 2000 (Thermo Fisher Scientific) and 25 μL of OptiMEM (Thermo Fisher Scientific) were mixed and incubated at room temperature for 5 minutes. Thereafter, the above plasmid+OptiMEM mixture and Lipofectamine 2000+OptiMEM mixture were mixed and incubated at room temperature for 20 minutes. The resulting mixture was mixed with 1 mL of the above EF medium containing HEK 293T cells and seeded in a 96-well plate (seeded in a total of 12 wells, 1 well per combination of vectors).

After culturing at 37° C. in a 5% $CO_2$ atmosphere for 24 hours, a dual-Luciferase assay was carried out in accordance with the protocol of the Dual-Glo Luciferase assay system (Promega). For measurement of luciferase and Renilla luciferase, Centro $XS^3$ LB 960 (BERTHOLD TECHNOLOGIES) was used.

The same experiment was conducted under the following conditions as a control experiment.

1. Instead of any one of the Cas3 plasmid, the Cse1 (Cas8) plasmid, the Cse2 (Cas11) plasmid, the Cas5 plasmid, the Cas6 plasmid, and the Cas7 plasmid, the same amount of pBluecscript II KS(+) vector (Agilent Technologies) was mixed for expression (2 to 7 in FIG. 1).
2. Instead of the crRNA plasmid used in the above procedure, plasmids for expressing a crRNA not complementary to the target sequence were mixed. Specifically, for the purpose of expression, plasmids for expressing the crRNA corresponding to the spacer sequence of *E. coli* CRISPR were mixed for the target sequence derived from the CCR5 gene (8 in FIG. 1), and plasmids for expressing the crRNA corresponding to the sequence derived from the CCR5 gene were mixed when targeting the spacer sequence of *E. coli* CRISPR (11 in FIG. 1).
3. As negative controls, only a reporter vector having the target sequence derived from CCR5 (9 in FIG. 1) and only a reporter vector having the spacer sequence of *E. coli* CRISPR (12 in FIG. 1) were expressed.

Results

Figure 1:
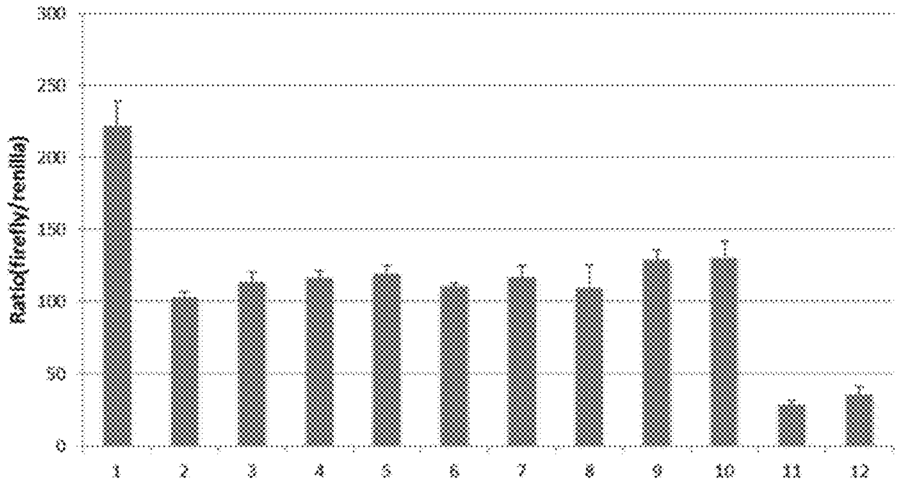
FIG. 1 is the results of SSA assay measuring cleavage activity against exogenous DNA.

The results of the dual-Luciferase assay are shown in the graph of FIG. 1, and the experimental conditions are shown in the lower table of FIG. 1. In FIG. 1, "CCR5-target" and "spacer-target" represent the target sequence derived from CCR5 and the spacer sequence of *E. coli* CRISPR, respectively. In addition, "CCR5-crRNA" and "spacer-crRNA" represent the sequence complementary to CCR5-target and the sequence complementary to spacer-target, respectively.

In FIG. 1, the system into which the crRNA plasmid complementary to the target sequence and all of the Cas3 plasmid, the Cse1 (Cas8) plasmid, the Cse2 (Cas11) plasmid, the Cas5 plasmid, the Cas6 plasmid, and the Cas7 plasmid were introduced exhibited cleavage activity higher than that of other systems (compare between 1 and 2 to 8, and between 10 and 11). Therefore, it was found that it is possible to express Cas3, Cse1 (Cas8), Cse2 (Cas11), Cas5, Cas6, and Cas7 in human cells by using the expression vectors according to an embodiment of the present invention.

In addition, it was suggested that introducing of the above expression vectors into human cells forms Cas3, Cascade, and crRNA complexes in human cells and cleaves the target sequence.

Furthermore, in FIG. 1, comparison between 8 and 9 and between 11 and 12 reveals that cleavage activity was equivalent to that of the negative controls in a system expressing a crRNA not complementary to the target sequence. In other words, it was suggested that the CRISPR-Cas3 system of the present invention can specifically cleave sequences complementary to crRNA in mammalian cells.

Example A-2

An experiment was conducted to evaluate whether or not it is possible to cleave endogenous DNA of human cells by type I CRI SPR-Cas systems using the same method as in Example A-1.

Specifically, the nucleic acid sequence in human cells was modified to express pre-crRNA and Cas3, Cse1 (Cas8), Cse2 (Cas11), Cas5, Cas6, and Cas7 added with nuclear localization signals, and evaluation was conducted on whether or not the sequence of the endogenous CCR5 gene of the cells would be cleaved.

The same HEK 239T cells as in Example A-1 were seeded in a 24-well plate at a density of $1\times10^5$ cells/well and cultured for 24 hours.

Mixed with 50 μL of Opti-MEM (Thermo Fisher Scientific) were 1 μg of the Cas3 plasmid, 1.3 μg of the Cse1 (Cas8) plasmid, 1.3 μg of the Cse2 (Cas11) plasmid, 1.1 μg of the Cas5 plasmid, 0.8 μg of the Cas6 plasmid, 0.3 μg of the Cas7 plasmid, and 1 μg of the crRNA plasmid. Subsequently, a mixture of 5 μL of Lipofectamine (registered trademark) 2000 (Thermo Fisher Scientific), 50 μL of Opti-MEM (Thermo Fisher Scientific), and 1 mL of EF medium was added to the above DNA mixture. Thereafter, 1 mL of the resulting mixture was added to the above 24-well plate.

After culturing at 37° C. in a 5% $CO_2$ atmosphere for 24 hours, the medium was replaced with 1 mL of EF medium. Past 48 hours following transfection (24 hours after medium replacement), the cells were harvested and adjusted to a concentration of $1\times10^4$ cells/5 μL in PBS.

The above cells were heated at 95° C. for 10 minutes. Next, 10 mg of proteinase K was added, followed by incubation at 55° C. for 70 minutes. Furthermore, the product heat-treated at 95° C. for 10 minutes was used as a template for PCR.

By performing 35 cycles of 2-step PCR, 10 μL of the above template was amplified. Here, primers having the sequences of SEQ ID NOs: 47 and 48 were used as primers for PCR. In addition, KOD FX (Toyobo Co., Ltd.) was used as a DNA polymerase, and the 2-step PCR procedure was in accordance with the protocol attached to KOD FX. The product amplified by PCR was purified using QIAquick PCR Purification Kit (QIAGEN). The specific procedure was in accordance with the protocol attached to the above kit.

The dA was added to the 3'-end of the purified DNA obtained using rTaq DNA polymerase (Toyobo Co., Ltd.). The purified DNA was subjected to electrophoresis in a 2% agarose gel, and a band of about 500 to 700 bp was cut out. Then, DNA was extracted from the cut gel and purified using a Gel extraction kit (QIAGEN). Next, TA cloning was carried out using pGEM-T easy vector Systems (Promega), and the above DNA was cloned. Finally, DNA cloned by alkaline prep method was extracted and analyzed by Sanger sequence. For the analysis, BigDye (registered trademark) Terminator v 3.1 Cycle Sequencing Kit (Thermo Fisher Scientific) and Applied Biosystems 3730 DNA Analyzer (Thermo Fisher Scientific) were used.

Figure 2:
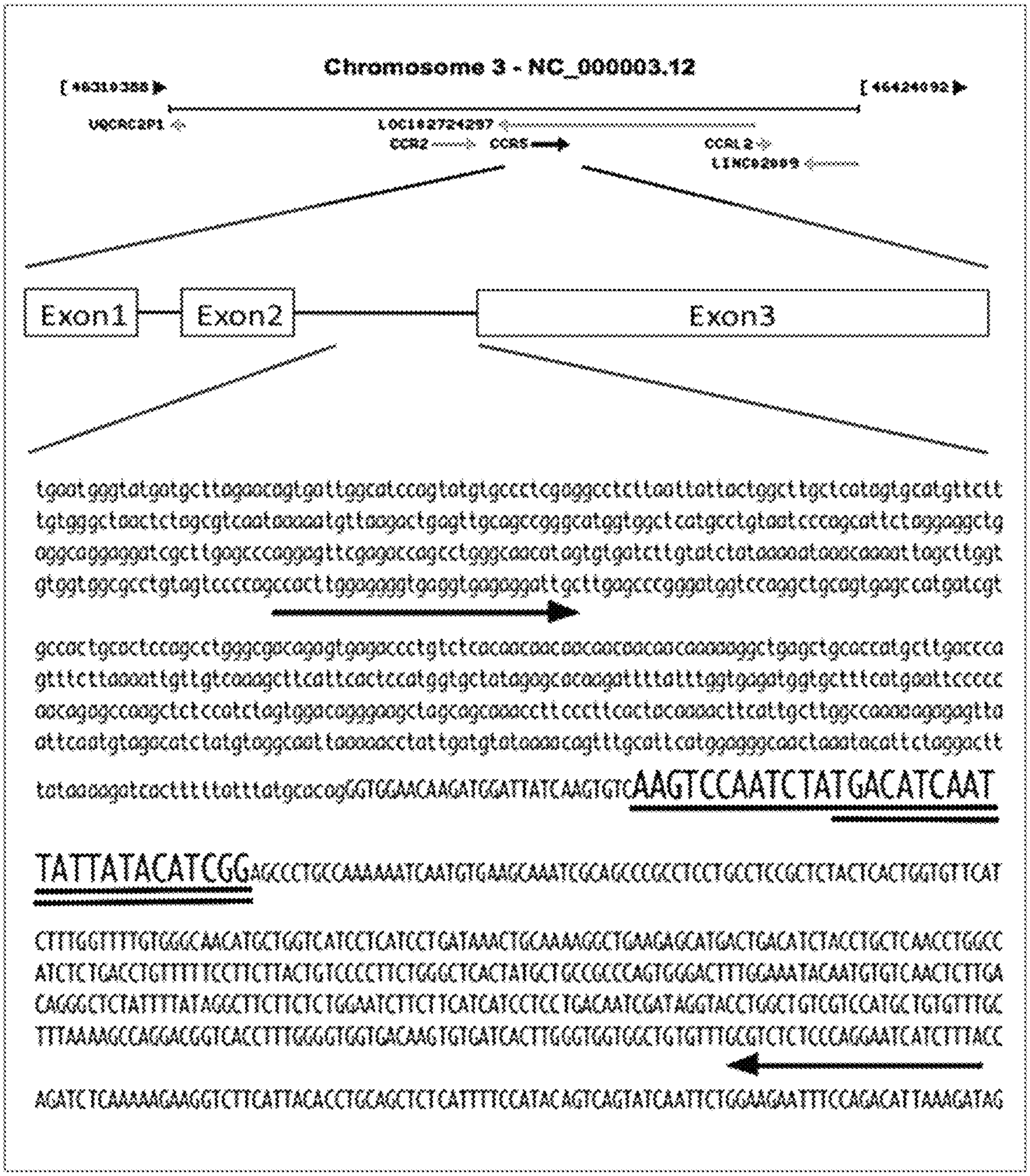
FIG. 2 is a schematic diagram showing the position of the target sequence in the CCR5 gene (SEQ ID NO: 63).

The outline of the endogenous CCR5 gene sequence, the target of the CRISPR-Cas system in this example, is described based on FIG. 2. Note that in FIG. 2, the exons are in capital letters, and the introns are in lowercase letters.

In this example, the target was the sequence within the CCR5 gene located in third chromosome short arm (P) region 21 (FIG. 2; the entire length of the nucleic acid sequence of CCR5 is shown at SEQ ID NO: 46). Specifically, the sequence within Exon 3 of the CCR5 gene was used as the target sequence. As a control, the target sequence of Cas9 was also arranged at approximately the same position. More precisely, the entire underlined sequence is the target sequence of type I CRISPR-Cas system (AAG and the following 32 bases), and the double underlined sequence is the target sequence of Cas9 (CGG and the preceding 20 bases). The sequence of crRNA was designed to allow guidance to the target sequence of the type I CRISPR-Cas system (AAG and the following 32 bases).

Results

The results of the above experiment were such that clone 1 having 401 bp deleted, clone 2 having 341 bp deleted, clone 3 having 268 bp deleted, and clone 4 having 344 bp deleted were obtained as compared with the original nucleic acid sequences (FIGS. 3A to 3D). This showed that it is possible to delete the endogenous DNA of human cells by the CRISPR-Cas3 system of the present invention. Specifically, it was suggested that the above CRISPR-Cas system enables editing of DNA of human cells.

This example observed clones having base pairs deleted. This fact supports that DNA cleavage takes place at multiple sites, according to the CRISPR-Cas3 system of the present invention.

DNA of several hundred base pairs (268 to 401 bp) was deleted by the CRISPR-Cas3 system of the present invention. This was more extensive than the deletion obtained by the CRISPR-Cas system using Cas9 (usually cleaved at only one site on the DNA).

Example A-3

An experiment was conducted to evaluate whether or not it is possible to cleave the endogenous DNA of human cells by the CRISPR-Cas3 system using the same method as in Example A-1.

Specifically, the nucleic acid sequence in human cells was modified to express pre-crRNA and Cas3, Cse1 (Cas8), Cse2 (Cas11), Cas5, Cas6, and Cas7 added with nuclear localization signals, and evaluation was conducted on whether or not the sequence of the endogenous EMX1 gene of the cells would be cleaved.

The same HEK 293T cells as in Example A-1 were seeded in a 24-well plate at a density of $1\times10^5$ cells/well and cultured for 24 hours.

Mixed with 50 μL of Opti-MEM (Thermo Fisher Scientific) were 500 ng of the Cas3 plasmid, 500 ng of the Cse1 (Cas8) plasmid, 1 μg of the Cse2 (Cas11) plasmid, 1 μg of the Cas5 plasmid, 1 μg of the Cas6 plasmid, 3 μg of the Cas7 plasmid, and 500 μg of the crRNA plasmid. Further added and mixed in the above mixture were 4 μL of Lipofectamine (registered trademark) 2000 (Thermo Fisher Scientific) and 50 μL of Opti-MEM (Thermo Fisher Scientific). The resulting mixture was incubated at room temperature for 20 min and then added to the HEK 293T cells.

Here, the structure of the expression vector of the Cas protein group used in Example A-3 is shown in FIG. 7. As shown in FIG. 7, the above expression vector is obtained by sandwiching the sequence encoding the Cas protein group with BPNLSs (bipartite NLSs) (see [Suzuki K et al. (2016) In vivo genome editing via CRISPR/Cas9 mediated homology-independent targeted integration, Nature, Vol. 540 (Issue 7631), pp. 144-149]). The amino acid sequence of BPNLS is KRTADGSEFESPKKKRKVE (SEQ ID NO: 54), and the nucleic acid sequence is AAGCGGACTGCTGATGGCAGTGAATTTGAGTCCCCAAAGAAGAAGAGAAAGGTGGAA (SEQ ID NO: 55).

After the above HEK 293T cells were cultured at 37° C. in a 5% $CO_2$ atmosphere for 24 hours, the medium was replaced with 1 mL of EF medium (1 mL per 1 well). Past 48 hours following transfection (24 hours after medium replacement), the cells were harvested and adjusted to a concentration of $1\times10^4$ cells/5 μL in PBS.

The above cells were heated at 95° C. for 10 minutes. Next, 10 mg of proteinase K was added, followed by incubation at 55° C. for 70 minutes. Furthermore, the product heat-treated at 95° C. for 10 minutes was used as a template for PCR.

By performing 40 cycles of 3-step PCR, 10 μL of the above template was amplified. Here, primers having the sequences of SEQ ID NOs: 50 and 51 were used as primers for PCR. In addition, Hotstartaq (QIAGEN) was used as a DNA polymerase, and the 3-step PCR procedure was in accordance with the protocol attached to Hotstartaq. The product amplified by PCR was subjected to electrophoresis in a 2% agarose gel, and a band of about 900 to 1100 bp was cut out. Then, DNA was extracted from the cut gel and purified using a Gel extraction kit (QIAGEN). The specific procedure was in accordance with the protocol attached to the above kit.

Next, TA cloning was carried out using pGEM-T easy vector Systems (Promega), and the above DNA was cloned. Finally, DNA cloned by alkaline prep method was extracted and analyzed by Sanger sequence. For the analysis, BigDye (registered trademark) Terminator v3.1 Cycle Sequencing Kit (Thermo Fisher Scientific) and Applied Biosystems 3730 DNA Analyzer (Thermo Fisher Scientific) were used.

Figure 5:
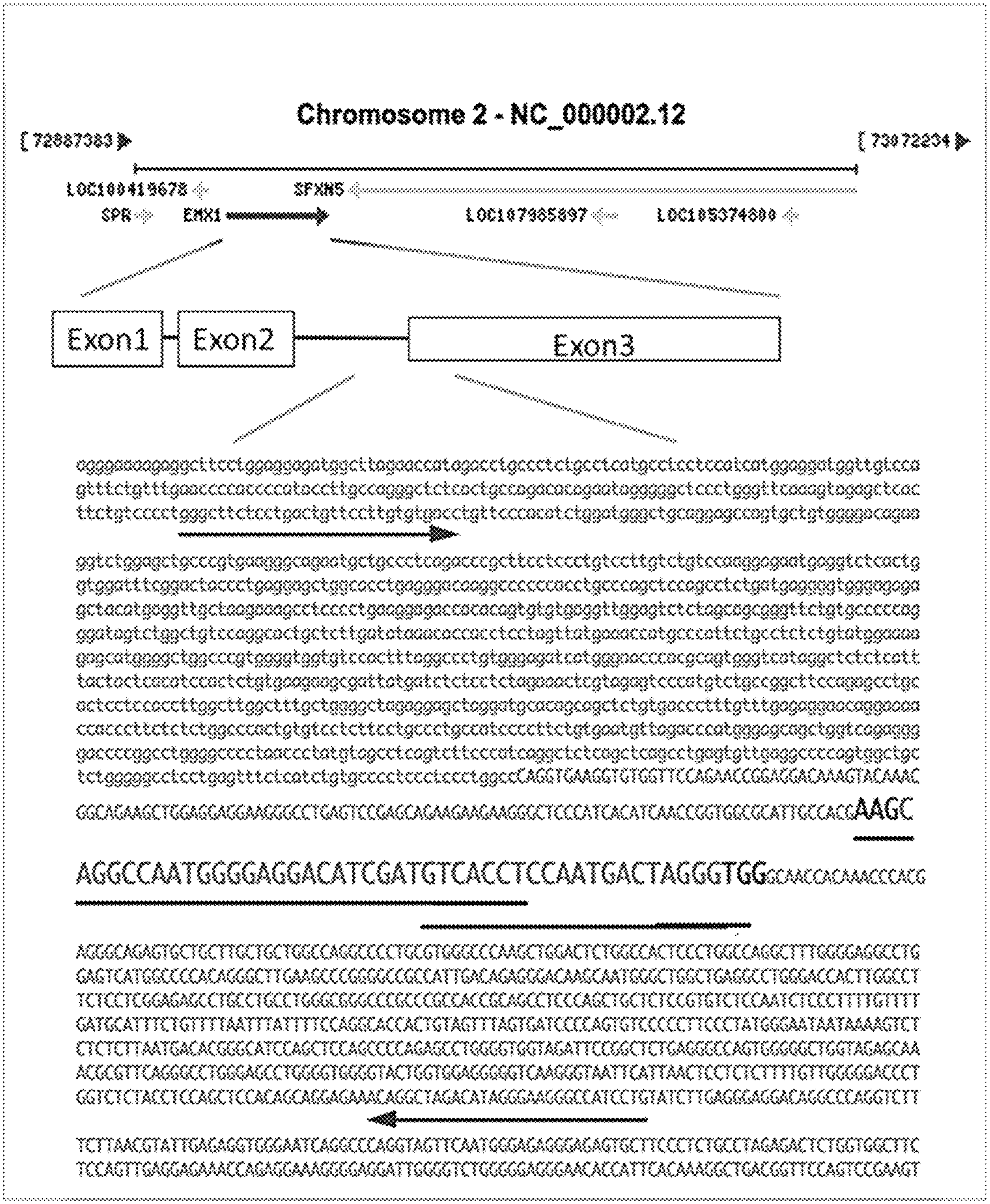
FIG. 5 is a schematic diagram showing the position of the target sequence in the EMX1 gene (SEQ ID NO: 68).

The outline of the endogenous EMX1 gene sequence, the target of the CRISPR-Cas3 system in Example A-3, is described based on FIG. 5. Note that in FIG. 5, the exons are in capital letters, and the introns are in lowercase letters.

In Example A-3, the target was the sequence within the EMX1 gene located in second chromosome short arm (P) region 13 (FIG. 5; the entire length of the nucleic acid sequence of EMX1 is shown at SEQ ID NO: 49). Specifically, the sequence within Exon 3 of the EMX1 gene was used as the target sequence. As a control, the target sequence of Cas9 was also arranged at approximately the same position. More precisely, the underlined sequence located upstream is the target sequence of type I CRISPR-Cas system (AAG and the following 32 bases), and the underlined sequence located downstream is the target sequence of Cas9 (TGG and the preceding 20 bases). The sequence of crRNA used in Example A-3 was designed to allow guidance to the target sequence of the CRISPR-Cas3 system (AAG and the following 32 bases).

Results

The results of the above experiment were such that clone 1 having two deleted sites of 513 bp and 363 bp and clone 2 having 694 bp deleted were obtained as compared with the original nucleic acid sequences (FIGS. 6A and 6B). These experimental results also showed that it is possible to delete the endogenous DNA of human cells by the CRISPR-Cas3 system of the present invention. Specifically, it was suggested that the above CRISPR-Cas3 system enables editing of DNA of human cells.

In addition, it was similar to Example A-2 that cleavage took place at two or more sites of the double-stranded DNA, and DNA of several hundred base pairs was deleted. Therefore, the results of Example A-3 more strongly support the suggestions obtained from Example A-2.

Example A-4

The cleavage activity of the target sequence of the exogenous DNA was evaluated as follows. HEK 293T cells were caused to express the CRISPR-Cas3 system in which the nucleic acid sequences were modified and the nucleic acid sequences encoding Cascade proteins were linked.

In Example A-4, 100 ng of the reporter vector; 200 ng of each of the Cas3 plasmid, the Cascade (2A) plasmid, and the crRNA plasmid; 60 ng of pRL-TK vector (capable of expressing Renilla luciferase, Promega); and 300 ng of pBluecscript II KS(+) vector (Agilent Technologies) were mixed in 25 μL of Opti-MEM (Thermo Fisher Scientific). The conditions using the reporter vector having the target sequence derived from CCR5 as the reporter vector correspond to 1 in (b) of FIG. 9, and the conditions using the reporter vector having the spacer sequence of *E. coli* CRISPR correspond to 6 in (b) of FIG. 9.

Here, as the above reporter vectors, the two kinds of reporter vectors prepared in [1] of [Preparation Example] (that is, vectors having the structure shown in FIG. 4(*d*)) were used. In addition, as the above Cascade (2A) plasmid, the expression vectors prepared in [4] of [Preparation Example] (that is, the vector having the structure shown in FIG. 8) were used.

A dual-Luciferase assay was carried out in the same method as Example A-1 except that the above expression vectors were used.

Moreover, the same experiment was conducted under the following conditions as a control experiment.

1. Instead of either one of the Cas3 plasmid and the Cascade (2A) plasmid, the same amount of pBluecscript II KS (+) vector (Agilent Technologies) was mixed for expression (2 and 3 in FIG. 9).

2. Instead of the crRNA plasmid used in the above procedure, plasmids for expressing a crRNA not complementary to the target sequence were mixed. Specifically, for the purpose of expression, plasmids for expressing the crRNA corresponding to the spacer sequence of *E. coli* CRISPR were mixed for the target sequence derived from the CCR5 gene (4 in FIG. 9), and plasmids for expressing the gRNA corresponding to the sequence derived from the CCR5 gene were mixed when targeting the spacer sequence of *E. coli* CRISPR (7 in FIG. 9).

3. As negative controls, only a reporter vector having the target sequence derived from CCR5 (5 in FIG. 9) and only a reporter vector having the spacer sequence of *E. coli* CRISPR (8 in FIG. 9) were expressed.

Results

Figure 9:
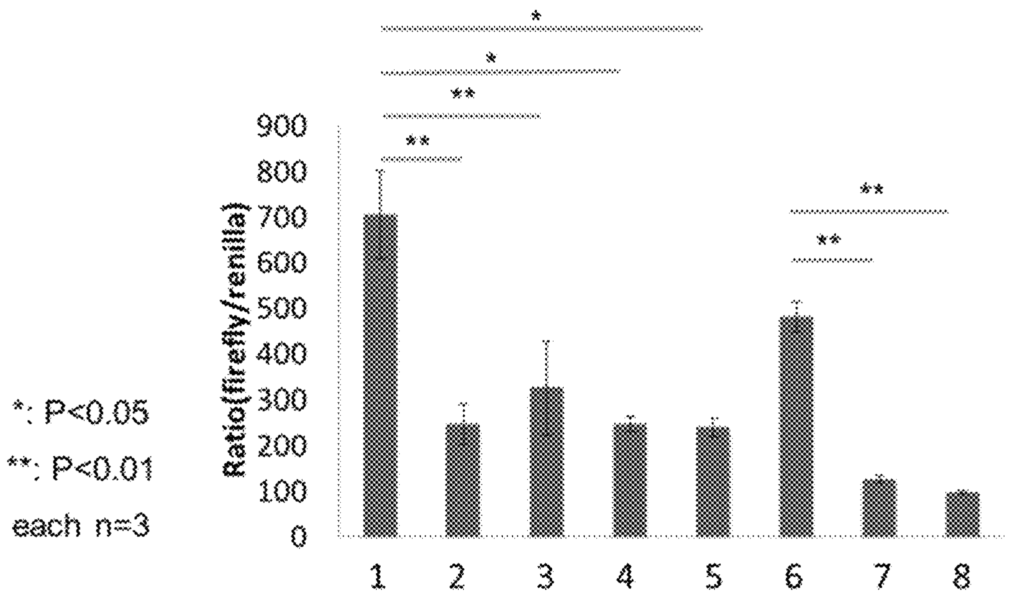
FIG. 9 is the results of SSA assay measuring cleavage activity against exogenous DNA

The results of the dual-Luciferase assay are shown in the graph of FIG. 9, and the experimental conditions are shown in the lower table of FIG. 9. In FIG. 9, "CCR5-target" and "spacer-target" represent the target sequence derived from CCR5 and the spacer sequence of *E. coli* CRISPR, respectively. In addition, "CCR5-crRNA" and "spacer-crRNA" represent the sequence complementary to CCR5-target and the sequence complementary to spacer-target, respectively.

As shown in FIG. 9, the system into which the crRNA plasmid complementary to the target sequence and both of the Cas3 plasmid and the Cascade (2A) plasmid were introduced exhibited cleavage activity significantly higher than that of other systems (compare between 1 and 2 to 5, and between 6, 7, and 8). Thus, it was suggested that, even in a system in which nucleic acid sequences encoding Cascade proteins are linked for expression, it is possible to specifically cleave sequences complementary to crRNA in mammalian cells by using the CRISPR-Cas system according to an embodiment of the present invention.

B. Examination of Factors and the Like Affecting Genome Editing by CRISPR-Cas3 System in Eukaryotic Cell

Material and Method

[1] Configuration of Cas Gene and crRNA

Constituent genes of Cas3 and Cascade (Cse1, Cse2, Cas5, Cas6, and Cas7) derived from *E. coli* K-12 strain, to which bpNLSs were added to the 5' side and the 3' side, were designed and cloned by codon optimization for mammalian cells followed by gene synthesis. These genes were subcloned downstream of the CAG promoter of the pPB-CAG. EBNXN plasmid donated by Sanger Institute. Mutants of Cas3 such as H74A (dead nickase; dn), K320N (dead helicase; dh), and double mutants of S483A and T485A (dead helicase ver. 2; dh2) were prepared by self-ligation of PCR products of PrimeSTAR MAX. Regarding the crRNA expression plasmid, a sequence of crRNA having two BbsI restriction enzyme sites at the position of the spacer under the U6 promoter was synthesized. All crRNA expression plasmids were prepared by inserting 32-base-pair double-stranded oligos of the target sequence into the BbsI restriction enzyme sites.

The Cas9-sgRNA expression plasmid pX330-U6-Chimeric_BB-CBh-hSpCas9 was obtained from Addgene. Designing of gRNA employed CRISPR web tool, CRISPR design tool, and/or CRISPRdirect to predict unique target sites in the human genome. The target sequence was cloned into the sgRNA scaffold of pX330 in accordance with the protocol of the Feng Zhang laboratory.

The SSA reporter plasmid containing two BsaI restriction enzyme sites was donated by Professor YAMAMOTO Takashi at Hiroshima University. The target sequence of the genomic region was inserted into the BsaI sites. As a Renilla luciferase vector, pRL-TK (Promega) was obtained. All plasmids were prepared by midiprep or maxiprep method using PureLink HiPure Plasmid Purification Kit (Thermo Fisher).

[2] Evaluation of DNA Cleavage Activity with HEK 293T Cells

An SSA assay was carried out as in Example A in order to detect DNA cleavage activity in mammalian cells. HEK 293T cells were cultured at 37° C. in 5% $CO_2$ with high-Glucose Dulbecco's modified Eagle's medium supplemented with 10% fetal bovine serum (Thermo fisher). In the wells of a 96-well plate, $0.5\times10^4$ cells were seeded. After 24 hours, Cas3, Cse1, Cse2, Cas7, Cas5, Cas6, and crRNA expression plasmids (each 100 ng), SSA reporter vectors (100 ng), and Renilla luciferase vectors (60 ng) were transfected into HEK 293T cells by using lipofectamine 2000 and OptiMEM (Life Technologies) in accordance with a slightly modified protocol. Twenty four hours after the transfection, a dual luciferase assay was carried out by using the Dual-Glo luciferase assay system (Promega) in accordance with the protocol.

[3] Detection of Indels in HEK 293T Cells

In the wells of a 24-well plate, $2.5\times10^4$ cells were seeded. After 24 hours, Cas3, Cse1, Cse2, Cas7, Cas5, Cas6, and crRNA expression plasmids (each 250 ng) were transfected into HEK 293T cells by using lipofectamine 2000 and OptiMEM (Life Technologies) in accordance with a slightly modified protocol. Two days after the transfection, total DNA was extracted from the harvested cells by using Tissue XS kit (Takara-bio Inc.) in accordance with the protocol. The target locus was amplified by using Gflex (Takara bio Inc.) or Quick Taq HS DyeMix (TOYOBO Co., Ltd.), followed by electrophoresis in an agarose gel. For the purpose of detecting small insertion/deletion mutations in PCR products, SURVEYOR Mutation Detection Kit (Integrated DNA Technologies) was used in accordance with the protocol. For TA cloning, the pCR4Blunt-TOPO plasmid vector (Life Technologies) was used in accordance with the protocol. For sequence analysis, BigDye Terminator Cycle Sequencing Kit and ABI PRISM 3130 Genetic Analyzer (Life Technologies) were used.

For the purpose of detecting various unusual mutations, a DNA library of PCR amplification products was prepared using TruSeq Nano DNA Library Prep Kit (Illumina), and amplicon sequencing was carried out with MiSeq (2×150 bp) in accordance with the standard procedure by Macrogen. The raw reads of the samples were mapped to human genome hg38 by BWA-MEM. The coverage data was visualized with Integrative Genomics Viewer (IGV), and the histogram at the target region was extracted.

Reporter HEK 293T cells having mCherry-P2A-EGFP c321C>G for detecting SNP-KI (snip knock-in) in mammalian cells were donated by Professor NAKADA Shin-ichiro. The reporter cells were cultured with 1 μg/ml of puromycin. Single-stranded DNA or 500 ng of donor plasmid was co-introduced together with CRISPR-Cas3 by the method described above. All cells were harvested 5 days after the transfection, and FACS analysis was carried out using AriaIIIu (BD). GFP positive cells were sorted and total DNA was extracted by the method described above. SNP exchange in the genome was detected by PCR amplification using HiDi DNA polymerase (myPOLS Biotec).

[4] Detection of Off-Target Site Candidates

Off-target candidates of type I-E CRISPR were detected in human genome hg38 using GGGenome by two different procedures. As PAM candidate sequences, AAG, ATG, AGG, GAG, TAG, and AAC were selected in accordance with existing reports (Leenay, R. T, et al. Mol. Cell 62, 137-147 (2016), Jung, et al. Mol. Cell. 2017 Jung et al., Cell 170, 35-47(2017)). Positions with fewer mismatches were selected in the first approach for 32 base pairs of the target sequence excluding positions of multiples of 6 because it had been reported that such positions are not recognized as target sites. In the following approach, regions completely matching the 5'-end of the PAM side of the target sequence were detected and listed in descending order.

[5] Deep Sequencing of Off-Target Analysis

In whole genome sequencing, genomic DNA was extracted from the transfected HEK 293T cells and cleaved using the Covaris sonicator. A DNA library was prepared using TruSeq DNA PCR-Free LT Library Prep Kit (Illumina), and genomic sequencing was carried out using HiSeq X (2×150 bp) in accordance with the standard procedure by Takara Bio Inc. The raw reads of the samples were mapped to human genome hg38 by BWA-MEM and cleaned by the Trimmomatic program. Discordant read pairs and split reads were excluded by samtools and Lumpy-sv, respectively. For the purpose of detecting only large deletions in the same chromosome, the read pairs mapped to different chromosomes were removed using BadMateFilter of the Genome Analysis Toolkit program. The total number of the discordant read pairs or split reads in the 100 kb region was counted by Bedtools to calculate the error rate with the negative control. SureSelectXT custom DNA probes were designed with SureDesign under moderately stringent conditions and prepared by Agilent technologies to enrich the off-target candidates before the sequencing. The target regions were selected as follows. The probes near the target regions covered 800 kb upstream and 200 kb downstream of PAM. In the vicinity of off-target regions of CRISPR-Cas3, 9 kb upstream and 1 kb downstream of PAM candidates were covered. In the vicinity of the off-target regions of CRISPR-Cas9, 1 kb of upstream and 1 kb of downstream of PAM were covered. After preparation of the DNA library with SureSelectXT reagent kit and custom probe kit, genome sequencing was carried out with Hiseq 2500 (2×150 bp) in accordance with the standard procedure by Takara Bio Inc. Discordant lead pairs and split leads on the same chromosome were excluded by the method described above. The total number of the discordant read pairs or split reads in the 10 kb region was counted by Bedtools to calculate the error rate with the negative control.

Example B-1

Figure 10B:
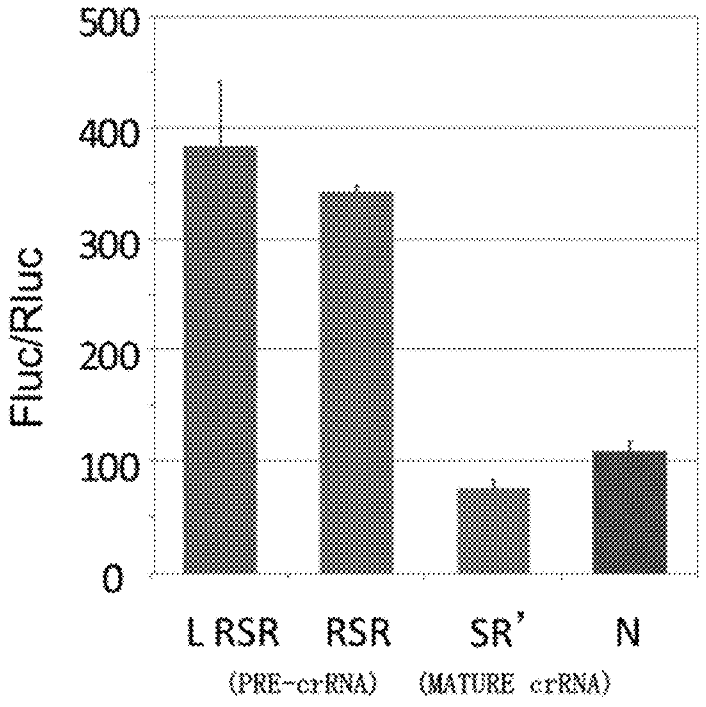
FIG. 10B is a diagram showing the results of SSA assay using the pre-crRNAs (LRSR and RSR) and the mature crRNA.

Influence of Types of crRNA and Nuclear Localization Signal on DNA Cleavage Activity In Example A, genomic editing in eukaryotic cells succeeded by chance by using a CRISPR-Cas3 system containing a pre-crRNA (LRSR; leader sequence-repeated sequence-spacer sequence-repeated sequence) as a crRNA. Here, the present inventors assumed that the reason why genome editing in eukaryotic cells using the CRISPR-Cas3 system had not been successful for many years was due to the fact that mature crRNA had been used as crRNA. In light of the above, in addition to the pre-crRNA (LRSR), a pre-crRNA (RSR; repeated sequence-spacer sequence-repeated sequence) and a mature crRNA (5'-handle sequence-spacer sequence-3'-handle sequence) were prepared as crRNAs, and the genome editing efficiency was examined with the reporter system of Example A (FIGS. 10A and 10B). Note that the nucleic acid sequences of the pre-crRNA (LRSR), the pre-crRNA (RSR), and the mature crRNA are shown at SEQ ID NOs: 63, 64, and 65, respectively.

Consequently, no cleavage activity of the target DNA was observed in the CRISPR-Cas3 system using the mature crRNA. On the other hand, it was surprising that, in the case of using the pre-crRNAs (LRSR and RSR), very high cleavage activity of the target DNA was observed. These results in the CRISPR-Cas3 system are in contrast with those of the CRISPR-Cas9 system, which exhibits high DNA cleavage activity by using a mature crRNA. In addition, this fact suggests that use of a mature crRNA is one of the reasons why genomic editing in eukaryotic cells has not succeeded in the CRISPR-Cas3 system.

Figure 11:
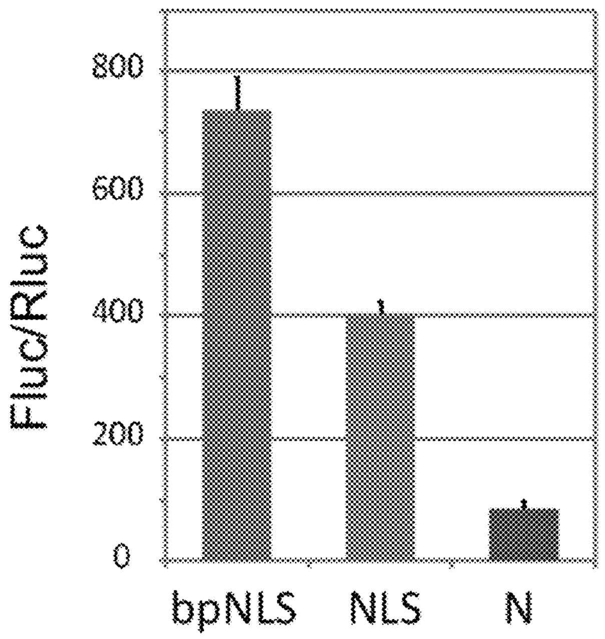
FIG. 11 shows the results of SSA assay using a single NLS or two NLSs (bpNLS) in a plasmid for the expression of the Cas3/Cascade gene.

In addition, examination was also carried out using the SV40 nuclear localization signal and bipartite nuclear translocation signal as nuclear localization signals added to Cas3 (FIG. 11). As a result, higher cleavage activity of target DNA was observed when the bipartite nuclear translocation signal was used.

Therefore, in the following experiments, the pre-crRNA (LRSR) was used as a crRNA and the bipartite nuclear translocation signal was used as a nuclear localization signal.

Example B-2

Influence of PAM Sequence on DNA Cleavage Activity

For the purpose of confirming the target specificity of the CRISPR-Cas3 system, the effects of various PAM sequences on DNA cleavage activity were examined (FIG. 12). In an SSA assay, the DNA cleavage activity showed various results for different PAM sequences. The highest activity was observed for 5'-AAG PAM, and AGG, GAG, TAC, ATG, and TAG also showed noticeable activity.

Example B-3

Influence of Mismatch of crRNA and Spacer Sequence on DNA Cleavage Activity

Figure 13:
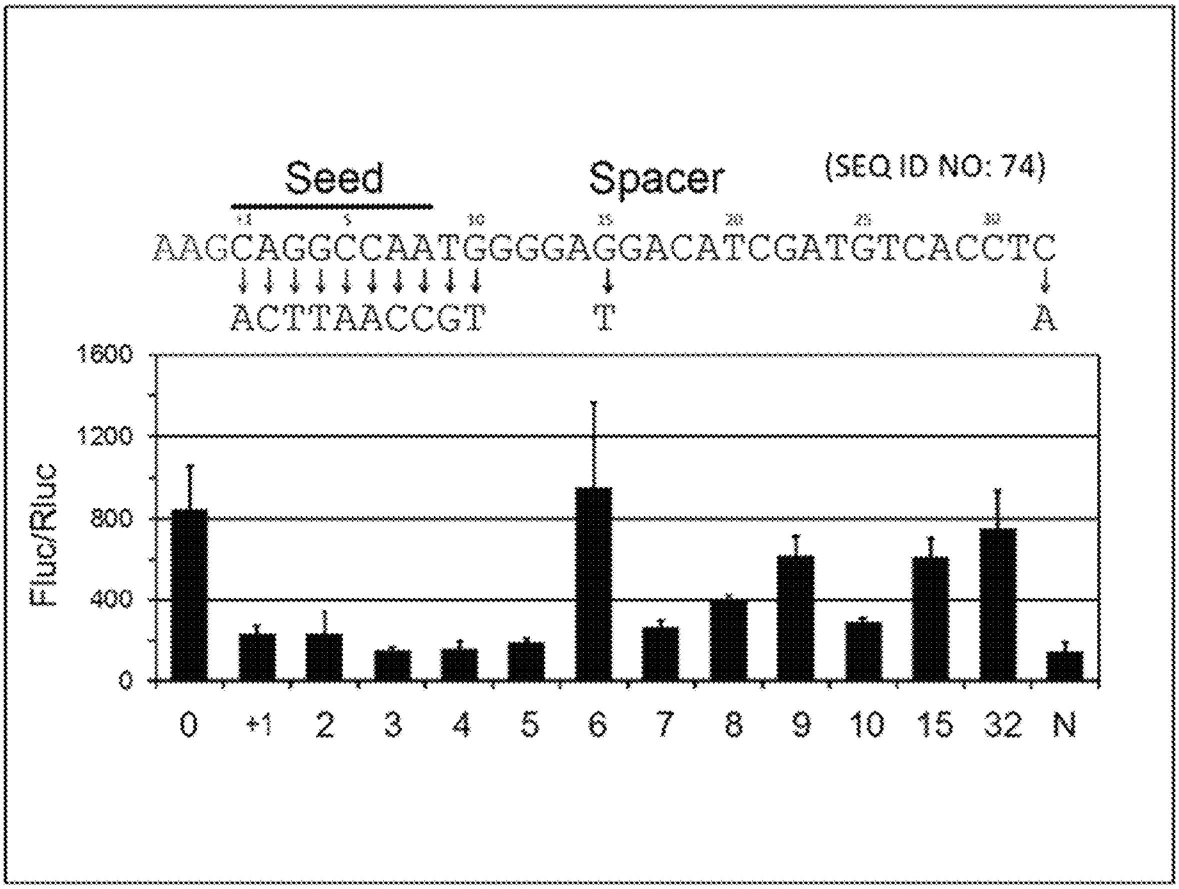
FIG. 13 is a diagram showing the effects of a single mismatch of the spacer on the DNA cleavage activity of the CRISPR-Cas3 system.

Studies in the past of the crystal structure of *E. coli* Cascade have shown that a heteroduplex of 5 base partitions is formed between crRNA and spacer DNA. This is due to the failure of base pairing at every sixth position by the SAM element of Cas7 effector (FIG. 13). The influence of mismatch of crRNA and spacer sequence on DNA cleavage activity was evaluated. Cleavage activity dropped dramatically at any single mismatch in the seed region (positions 1-8), except for bases not recognized as a target (position 6).

Example B-4

Examination of Necessity of Domains of Cas3 in DNA Cleavage Activity

Figure 14:
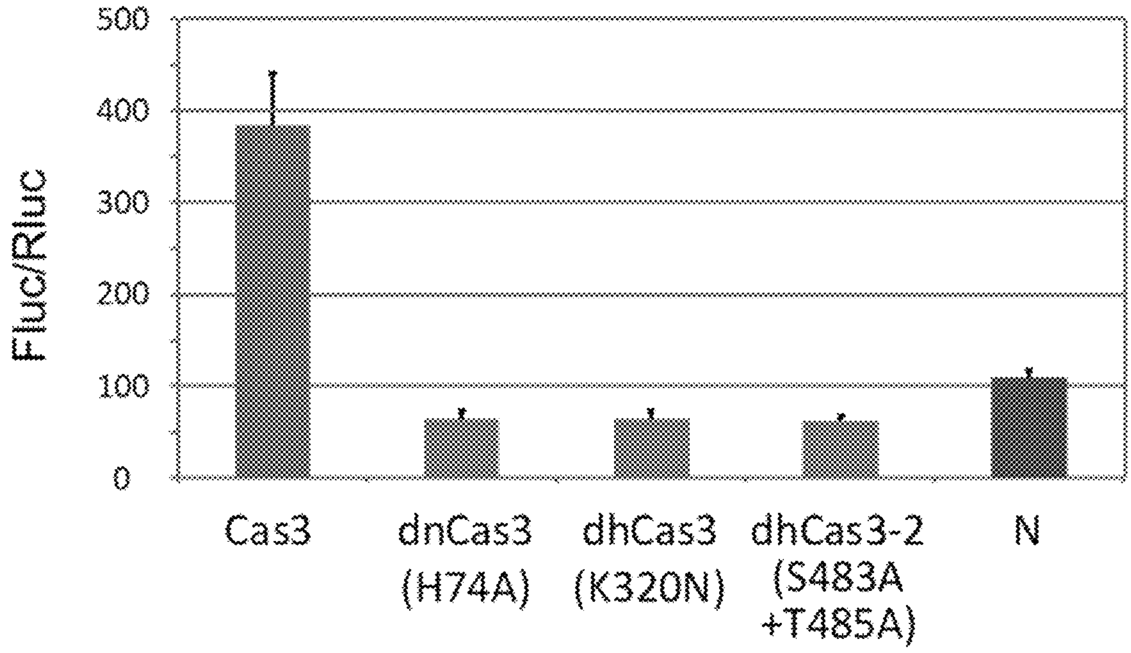
FIG. 14 is a diagram showing the effects of Cas3 mutation in HD nuclease domain (H74A), SF2 helicase domain motif 1 (K320A), and motif 3 (5483/T485A).

In vitro characterization of the catalytic characteristics of the Cas3 protein revealed that the N-terminus HD nuclease domain cleaves the single-stranded region of the DNA substrate, and subsequently the SF2 helicase domain at the C-terminus unwinds the target DNA in an ATP-dependent manner while proceeding in the 3'- to 5'-direction. Three Cas3 mutants, namely a mutant of HD domain H74A (dnCas3), a mutant of K320N of SF2 domain motif 1 (dhCas3), and a double mutant of S483A/T485A of SF2 domain motif 3 (dh2Cas3) were prepared to examine whether or not the Cas3 domain was necessary for DNA cleavage (FIG. 14). As a result, the DNA cleavage activity completely disappeared in all three mutants of Cas3 protein, revealing that Cas3 can cleave the target DNA through the HD nuclease domain and the SF2 helicase domain.

Example B-5

Examination of DNA Cleavage Activity in Various Types of CRISPR-Cas3 Systems The type 1 CRISPR-Cas3 systems have been highly diversified (A to G of type 1, seven types in total). The above examples examined the DNA cleavage activity in eukaryotic cells in the type I-E CRISPR-Cas3 system. On the other hand, this example examined the DNA cleavage activity in other type 1 CRISPR-Cas3 systems (type I-F and type I-G). Specifically, Cas3 and Cas5-7 of Shewanella putrefaciens of type I-F and Cas5-8 of Pyrococcus furiosus of type I-G were codon optimized and cloned (FIG. 15). As a result, DNA cleavage activity was also found in these type 1 CRISPR-Cas3 systems in the SSA assay using 293T cells although there was a difference in the strength of DNA cleavage activity.

Example B-6

Examination of Mutations Introduced into Endogenous Genes by CRISPR-Cas3 System The mutations introduced into endogenous genes by the CRISPR-Cas3 system were examined using the type I-E system. The EMX1 gene and the CCR5 gene were selected as target genes to prepare pre-crRNA (LRSR) plasmids. The 293T cells were lipofected with plasmids encoding pre-crRNA and six Cas (3, 5-8, and 11) effectors. As a result, the CRISPR-Cas3 revealed that deletion of several hundred to several thousand base pairs took place primarily in the upstream direction of the 5' PAM of the spacer sequence of the target region (FIG. 16). A microhomology of 5 to 10 base pairs at the repaired junction was confirmed, which may have been caused by annealing of the complementary strands by an annealing dependent repair pathway. Note that in the mature crRNA plasmids, no genome editing was found in the EMX1 and CCR5 regions.

Figure 17:
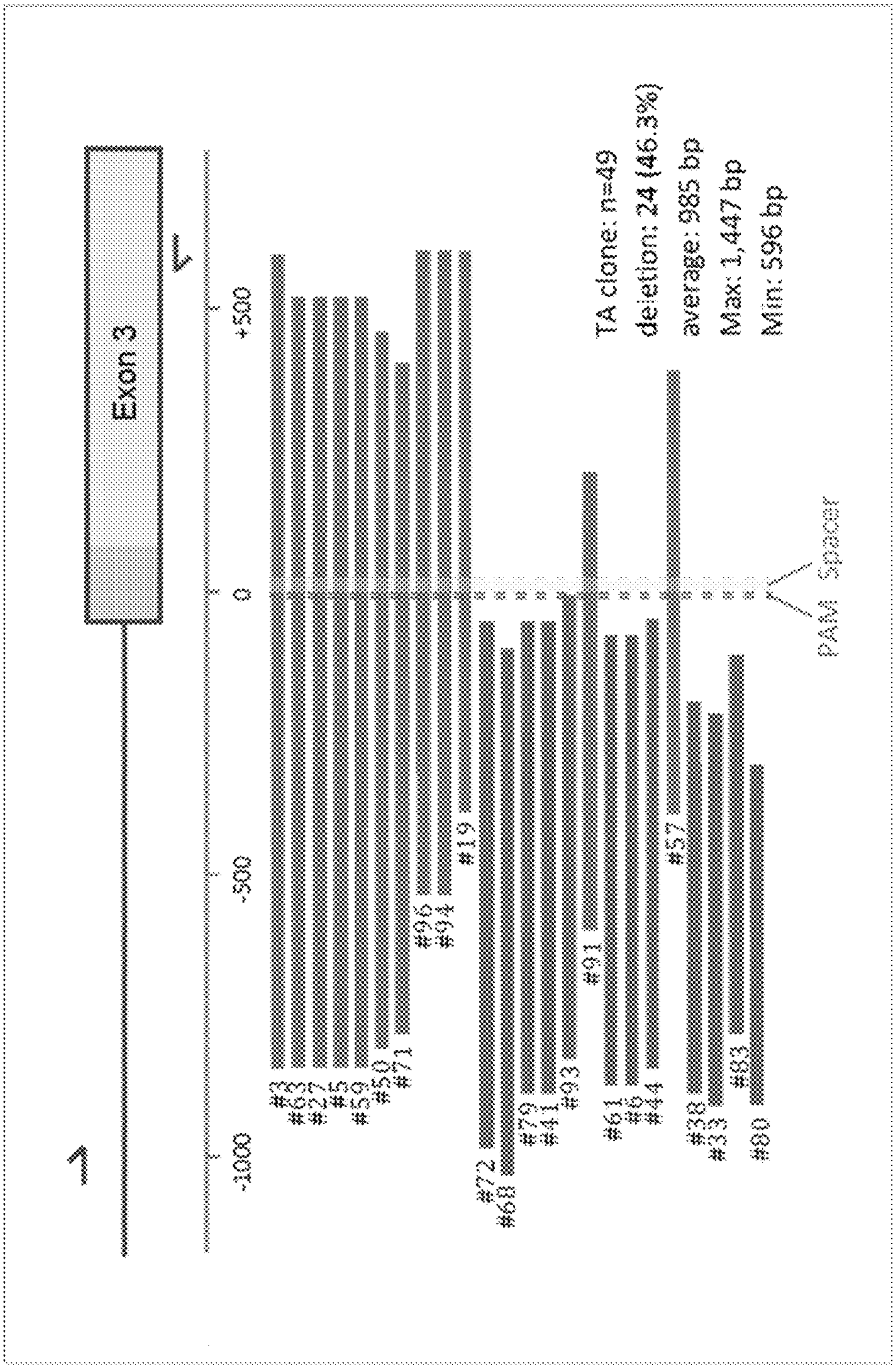
FIG. 17 is a diagram showing the position of deletion by the CRISPR-Cas3 system detected by a mass-processing sequencing of a TA clone (n=49).

Ninety six TA clones were picked up and compared with sequences of wild type EMX1 by sequencing for the purpose of further characterizing the genome editing by Cas3 by Sanger sequencing and TA cloning of PCR products (FIG. 17). Deletion of a minimum of 596 base pairs, a maximum of 1447 base pairs, and an average of 985 base pairs was observed in 24 clones out of 49 clones which could confirm sequence insertion (efficiency of 46.3%). Half of the clones (n=12) had large deletions including PAM and spacer sequences, and the other half were deleted upstream of PAM.

Further characterization of Cas3 was carried out by next generation sequencing by PCR amplification products with a primer set in broader regions such as 3.8 kb of the EMX1 gene and 9.7 kb of CCR5. Multiple PAM sites (AAG, ATG, and TTT) for targeting with type I-E CRISPR were also examined. In the amplicon sequencing, AAG was 38.2% and ATG was 56.4%. As compared with 86.4% of TTT and 86.4% of Cas9 targeting EMX1, the coverage rate in the broad genomic region upstream of the PAM site was greatly reduced. The decrease in coverage was similar when targeting the CCR 5 region. In contrast, Cas9 induced small insertions and small deletions (indels) at the target sites, while Cas3 had no small indel mutations at PAM or target site. These results suggested that the CRISPR-Cas3 system causes deletions in a wide range upstream of the target site in human cells.

Figure 18A:
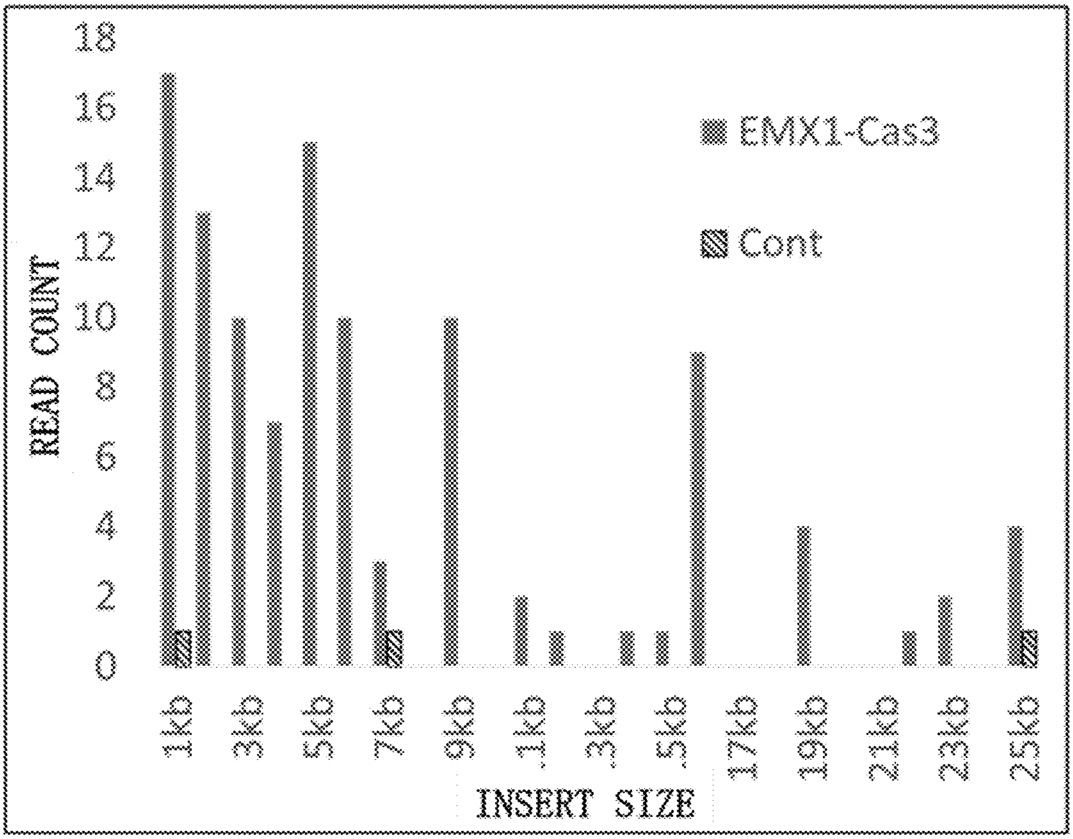
FIG. 18A is a diagram showing the number for each deletion size detected by the CRISPR-Cas3 system using a microarray-based capture sequence of 1000 kb or more around the targeted EMX1 locus.
Figure 18B:
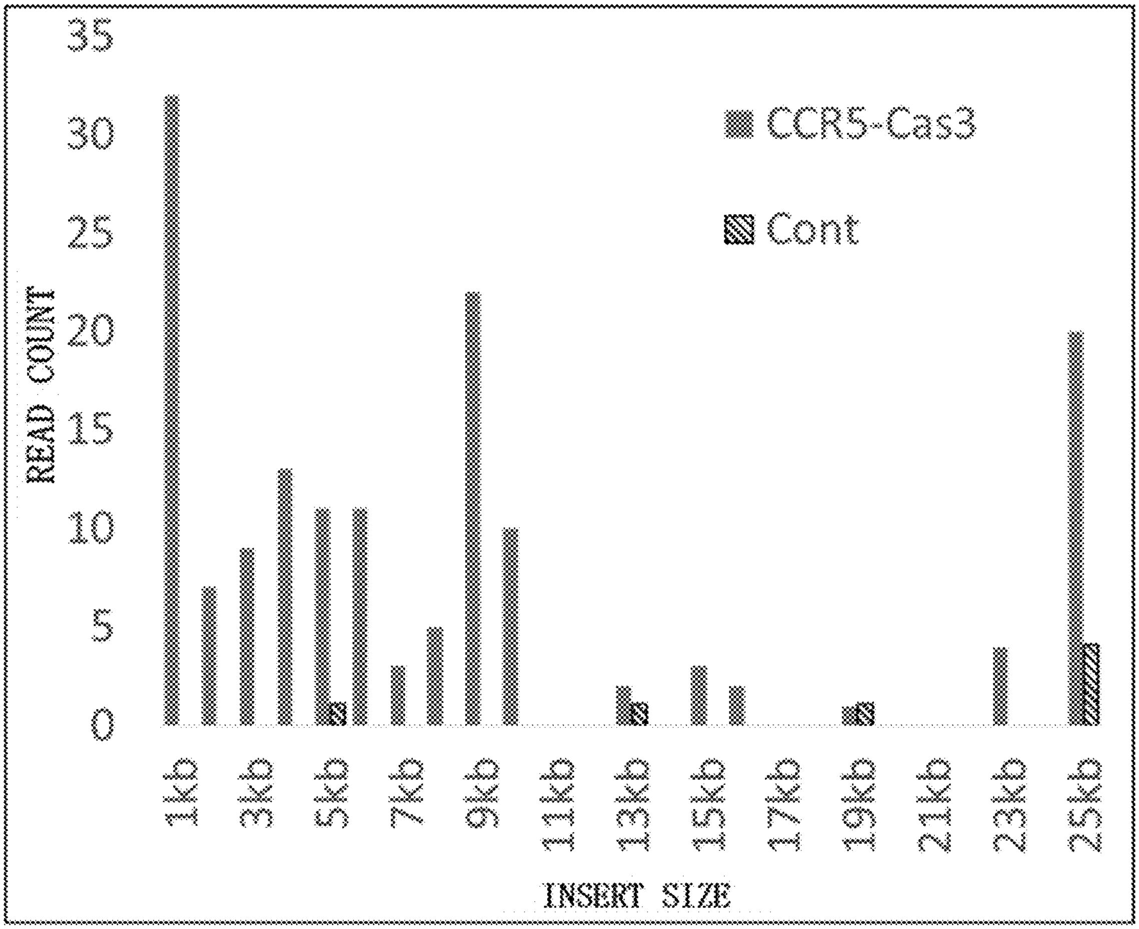
FIG. 18B is a diagram showing the number for each deletion size detected by the CRISPR-Cas3 system using a microarray-based capture sequence of 1000 kb or more around the targeted CCR5 locus.

Considering the limitations of PCR analysis such as amplification of less than 10 kb and strong bias favoring shorter PCR fragments, a microarray-based capture sequence of 1000 kb or more around the targeted EMX1 and CCR5 loci was used (FIGS. 18A and 18B). Deletion of up to 24 kb for the EMX1 locus and up to 43 kb for the CCR5 locus was observed. However, 90% of mutations at EMX1 and 95% of mutations at CCR5 were less than 10 kb. These results suggested that the CRISPR-Cas3 system may have potent nuclease and helicase activities in the eukaryotic genome.

It should be noted that whether or not undesirable off-target mutations can be induced in non-target genomic regions is a major concern particularly for clinical applications, as demonstrated in the CRISPR-Cas9 system. However, in the CRISPR-Cas3 system, no significant off-target effects were observed.

INDUSTRIAL APPLICABILITY

The CRISPR-Cas3 system of the present invention can edit DNA of eukaryotic cells, and therefore can be widely applied to fields requiring genome editing such as medicine, agriculture, forestry, and fisheries, industry, life science, biotechnology, and gene therapy.

Sequence Listing

The invention claimed is:

1. A method for cleaving endogenous DNA in a eukaryotic cell, comprising:

introducing a CRISPR-Cas3 system that can cleave endogenous DNA in a eukaryotic cell, wherein the CRISPR-Cas3 system is a Type I-E or Type I-G CRISPR-Cas3 system, and wherein the CRISPR-Cas3 system includes the following (A) to (C):

(A) a Cas3 protein, a polynucleotide encoding the protein, or an expression vector containing the polynucleotide, (B) all the Cascade proteins that constitute a Cascade complex, a polynucleotide encoding the Cascade proteins, or an expression vector containing the polynucleotide, and (C) a pre-crRNA which targets the endogenous DNA, a polynucleotide encoding the pre-crRNA, or an expression vector containing the polynucleotide.

2. The method according to claim 1, further comprising cleaving the pre-crRNA which targets the endogenous DNA with a protein constituting the Cascade protein after introducing the CRISPR-Cas3 system into the eukaryotic cell.

3. The method according to claim 1, wherein a nuclear localization signal is added to the Cas3 protein and/or one or more of the Cascade proteins.

4. The method according to claim 3, wherein the nuclear localization signal is a bipartite nuclear localization signal.

5. A method for cleaving endogenous DNA in a nonhuman animal or plant, comprising:

introducing a CRISPR-Cas3 system that can cleave endogenous DNA in a nonhuman animal or plant, wherein the CRISPR-Cas3 system is a Type I-E or Type I-G CRISPR-Cas3 system, and wherein the CRISPR-Cas3 system includes the following (A) to (C):

(A) a Cas3 protein, a polynucleotide encoding the protein, or an expression vector containing the polynucleotide, (B) all the Cascade proteins that constitute a Cascade complex, a polynucleotide encoding the Cascade proteins, or an expression vector containing the polynucleotide, and (C) a pre-crRNA which targets the endogenous DNA, a polynucleotide encoding the pre-crRNA, or an expression vector containing the polynucleotide.

* * * * *

```
                          SEQUENCE LISTING

<160> NUMBER OF SEQ ID NOS: 83

<210> SEQ ID NO 1
<211> LENGTH: 2685
<212> TYPE: DNA
<213> ORGANISM: Artificial Sequence
<220> FEATURE:
<223> OTHER INFORMATION: Synthetic sequence, modified Cas3 with NLS

<400> SEQUENCE: 1

atgcccaaga agaagcggaa ggtggaacct tttaaatata tatgccatta ctggggaaaa      60

tcctcaaaaa gcttgacgaa aggaaatgat attcatctgt taatttatca ttgccttgat     120

gttgctgctg ttgcagattg ctggtgggat caatcagtcg tactgcaaaa tactttttgc     180

cgaaatgaaa tgctatcaaa acagagggtg aaggcctggc tgttattttt cattgctctt     240

catgatattg gaaagtttga tatacgattc caatataaat cagcagaaag ttggctgaaa     300

ttaaatcctg caacgccatc acttaatggt ccatcaacac aaatgtgccg taaatttaat     360

catggtgcag ccggtctgta ttggtttaac caggattcac tttcagagca atctctcggg     420

gatttttca gtttttttga tgccgctcct catccttatg agtcctggtt tccatgggta      480

gaggccgtta caggacatca tggttttata ttacattccc aggatcaaga taagtcgcgt     540

tgggaaatgc cagcttctct ggcatcttat gctgcgcaag ataaacaggc tcgtgaggag     600

tggatatctg tactggaagc attattttta acgccagcgg ggttatctat aaacgatata     660

ccacctgatt gttcatcact gttagcaggt ttttgctcgc ttgctgactg gttaggctcc     720

tggactacaa cgaatacctt tctgtttaat gaggatgcgc cttccgacat aaatgctctg     780
```

-continued agaacgtatt tccaggaccg acagcaggat gcgagccggg tattggagtt gagtggactt 840
gtatcaaata agcgatgtta tgaaggtgtt catgcactac tggacaatgg ctatcaaccc 900
agacaattac aggtgttagt tgatgctctt ccagtagctc ccgggctgac ggtaatagag 960
gcacctacag gctccggtaa aacggaaaca gcgctggcct atgcttggaa acttattgat 1020
caacaaattg cggatagtgt tatttttgcc ctcccaacac aagctaccgc gaatgctatg 1080
cttacgagaa tggaagcgag cgcgagccac ttattttcat ccccaaatct tattcttgct 1140
catggcaatt cacggtttaa ccacctcttt caatcaataa aatcacgcgc gattactgaa 1200
caggggcaag aagaagcgtg ggttcagtgt tgtcagtggt tgtcacaaag caataagaaa 1260
gtgtttcttg ggcaaatcgg cgtttgcacg attgatcagg tgttgatatc ggtattgcca 1320
gttaaacacc gctttatccg tggtttggga attggtcgaa gtgttttaat tgttgatgaa 1380
gttcatgctt acgacaccta tatgaacggc ttgctggagg cagtgctcaa ggctcaggct 1440
gatgtgggag ggagtgttat tcttctttcc gcaaccctac caatgaaaca aaaacagaaa 1500
cttctggata cttatggtct gcatacagat ccagtggaaa ataactccgc atatccactc 1560
attaactggc gaggtgtgaa tggtgcgcaa cgttttgatc tgctagctca tccagaacaa 1620
ctcccgcccc gcttttcgat tcagccagaa cctatttgtt tagctgacat gttacctgac 1680
cttacgatgt tagagcgaat gatcgcagcg gcaaacgcgg gtgcacaggt ctgtcttatt 1740
tgcaatttgg ttgacgttgc acaagtatgc taccaacggc taaaggagct aaataacacg 1800
caagtagata tagatttgtt tcatgcgcgc tttacgctga acgatcgtcg tgaaaaagag 1860
aatcgagtta ttagcaattt cggcaaaaat gggaagcgaa atgttggacg gatacttgtc 1920
gcaacccagg tcgtggaaca atcactcgac gttgattttg attggttaat tactcagcat 1980
tgtcctgcag atttgctttt ccaacgattg ggccgtttac atcgccatca tcgcaaatat 2040
cgtcccgctg gttttgagat tcctgttgcc accattttgc tgcctgatgg cgagggttac 2100
ggacgacatg agcatattta tagcaacgtt agagtcatgt ggcggacgca gcaacatatt 2160
gaggagctta atggagcatc cttatttttc cctgatgctt accggcaatg gctggatagc 2220
atttacgatg atgcggaaat ggatgagcca gaatgggtcg gcaatggcat ggataaattt 2280
gaaagcgccg agtgtgaaaa aaggttcaag gctcgcaagg tcctgcagtg ggctgaagaa 2340
tatagcttgc aggataacga tgaaaccatt cttgcggtaa cgagggatgg ggaaatgagc 2400
ctgccattat tgccttatgt acaaacgtct tcaggtaaac aactgctcga tggccaggtc 2460
tacgaggacc taagtcatga acagcagtat gaggcgcttg cacttaatcg cgtcaatgta 2520
cccttcacct ggaaacgtag tttttctgaa gtagtagatg aagatgggtt actttggctg 2580
gaagggaaac agaatctgga tggatgggtc tggcagggta acagtattgt tattacctat 2640
acaggggatg aagggatgac cagagtcatc cctgcaaatc ccaaa 2685

<210> SEQ ID NO 2
<211> LENGTH: 1527
<212> TYPE: DNA
<213> ORGANISM: Artificial Sequence
<220> FEATURE:
<223> OTHER INFORMATION: Synthetic sequence, modified Cse1 with NLS

<400> SEQUENCE: 2
atgcccaaga agaagcggaa ggtgaacctg ctgattgaca actggatccc tgtgcgccca 60
cggaacggag gaaaagtcca gattattaat ctgcagagcc tgtactgctc ccgggatcag 120
tggagactga gcctgcccag agacgatatg gagctggccg ccctggccct gctggtgtgc 180
atcggccaga tcatcgcccc tgccaaggac gatgtggagt tcaggcaccg catcatgaac 240
cctctgaccg aggatgagtt tcagcagctg atcgccccat ggatcgacat gttctatctg 300
aatcacgccg agcacccctt catgcagaca aagggcgtga aggccaacga cgtgaccccc 360
atggagaagc tgctggcagg cgtgtccgga gcaacaaatt gcgccttcgt gaaccagcca 420
ggacagggag aggccctgtg cggaggctgt accgccatcg ccctgtttaa tcaggcaaac 480
caggcacctg gattcggagg aggctttaag tctggactga ggggaggaac cccagtgacc 540
acattcgtga gaggcatcga tctgaggagc acagtgctgc tgaatgtgct gaccctgcca 600
cggctgcaga agcagtttcc caatgagagc cacacagaga accagcccac ctggatcaag 660
cctatcaagt ctaacgagag catccctgcc agctccatcg gcttcgtgag aggcctgttt 720
tggcagccag cccacatcga gctgtgcgac cccatcggca tcggcaagtg ttcttgctgt 780
ggccaggaaa gcaatctgag gtacaccggc ttcctgaagg agaagttcac ctttacagtg 840
aacggcctgt ggccccaccc tcactctcca tgtctggtga cagtgaagaa gggcgaggtg 900
gaggagaagt tcctggcctt taccacatcc gccccctctt ggacccagat cagcagagtg 960
gtggtggaca agatcatcca gaacgagaat ggcaacagag tggccgccgt ggtgaatcag 1020
ttcaggaaca tcgccccaca gtctcccctg gagctgatca tgggcggcta caggaacaat 1080
caggccagca tcctggagcg gagacacgat gtgctgatgt ttaatcaggg ctggcagcag 1140
tatggcaatg tgatcaacga gatcgtgaca gtgggcctgg gctacaagac cgccctgaga 1200
aaggccctgt atacattcgc cgagggcttt aagaacaagg acttcaaggg agcaggcgtg 1260
agcgtgcacg agaccgccga gaggcacttt taccgccagt ccgagctgct gatccccgat 1320
gtgctggcca atgtgaactt ctcccaggcc gacgaagtga tcgccgatct gagggacaag 1380
ctgcaccagc tgtgcgagat gctgtttaac cagtctgtgg ccccatacgc ccaccacccc 1440
aagctgatca gcacactggc cctggcaagg gccaccctgt ataagcacct gagggagctg 1500
aagccacagg aggaccttc taatgga 1527

<210> SEQ ID NO 3
<211> LENGTH: 501
<212> TYPE: DNA
<213> ORGANISM: Artificial Sequence
<220> FEATURE:
<223> OTHER INFORMATION: Synthetic sequence, modified Cse2 with NLS

<400> SEQUENCE: 3
atgcccaaga agaagcggaa ggtggccgat gagatcgacg caatggcact gtacagggca 60
tggcagcagc tggacaacgg atcttgcgca cagatcaggc gcgtgagcga gcctgatgag 120
ctgagggaca tcccagcctt ctatcggctg gtgcagccct ttggctggga gaatcctaga 180
caccagcagg ccctgctgag gatggtgttt tgtctgagcg ccggcaagaa cgtgatccgg 240
caccaggaca agaagagcga gcagaccaca ggaatctccc tgggacgcgc cctggccaat 300
tccggccgga tcaacgagcg gagaatcttc cagctgatca gggccgatcg cacagccgac 360
atggtgcagc tgaggcgcct gctgacccac gcagagcctg tgctggattg gccactgatg 420
gcccgcatgc tgacatggtg gggcaagcgg gagagacagc agctgctgga ggacttcgtg 480
ctgaccacaa ataagaacgc c 501

<210> SEQ ID NO 4
<211> LENGTH: 693
<212> TYPE: DNA

<213> ORGANISM: Artificial Sequence
<220> FEATURE:
<223> OTHER INFORMATION: Synthetic sequence, modified Cas5 with NLS

<400> SEQUENCE: 4
atgcccaaga agaagcggaa ggtgcgctcc tacctgatcc tgagactggc aggaccaatg 60
caggcatggg gacagcctac attcgaggga accaggccaa caggccgctt tcctacccgg 120
tctggactgc tgggactgct gggagcctgc ctgggcatcc agagggacga tacctctagc 180
ctgcaggccc tgagcgagtc cgtgcagttc gccgtgcgct gtgatgagct gatcctggac 240
gataggcgcg tgtccgtgac aggcctgcgg gattaccaca ccgtgctggg cgccagagag 300
gactataggg gcctgaagtc ccacgagacc atccagacat ggcgcgagta cctgtgcgac 360
gcctctttta cagtggccct gtggctgacc ccacacgcaa caatggtcat cagcgagctg 420
gagaaggccg tgctgaagcc acggtacacc ccctatctgg gccggagaag ctgccctctg 480
acacacccac tgttcctggg cacctgtcag gcctccgatc cccagaaggc cctgctgaac 540
tacgagcctg tgggcggcga catctattct gaggagagcg tgacaggcca ccacctgaag 600
ttcaccgcca gggatgagcc aatgatcaca ctgccaaggc agtttgcatc cagggagtgg 660
tatgtgatca agggaggaat ggacgtgagc cag 693

<210> SEQ ID NO 5
<211> LENGTH: 618
<212> TYPE: DNA
<213> ORGANISM: Artificial Sequence
<220> FEATURE:
<223> OTHER INFORMATION: Synthetic sequence, modified Cas6 with NLS

<400> SEQUENCE: 5
atgcccaaga agaagcggaa ggtgtacctg agcaaagtga tcatcgcaag ggcatggtcc 60
agggacctgt atcagctgca ccagggcctg tggcacctgt tccctaatag accagatgcc 120
gccagggact tcctgtttca cgtggagaag aggaacacac ccgagggctg tcacgtgctg 180
ctgcagtccg cccagatgcc cgtgagcacc gcagtggcca cagtgatcaa gaccaagcag 240
gtggagttcc agctgcaagt gggcgtgcca ctgtacttta ggctgcgcgc caatcccatc 300
aagaccatcc tggataacca gaagcgcctg gactctaagg gcaatatcaa gcggtgcaga 360
gtgcctctga tcaaggaggc cgagcagatc gcctggctgc agagaaagct gggcaacgcc 420
gccagggtgg aggatgtgca ccctatcagc gagcggccac agtatttcag cggcgacggc 480
aagtccggca agatccagac cgtgtgcttt gagggcgtgc tgaccatcaa cgatgcccca 540
gccctgatcg acctggtgca gcagggaatc ggacctgcta agtcaatggg atgtgggctg 600
ctgtcactgg cacctctg 618

<210> SEQ ID NO 6
<211> LENGTH: 1110
<212> TYPE: DNA
<213> ORGANISM: Artificial Sequence
<220> FEATURE:
<223> OTHER INFORMATION: Synthetic sequence, modified Cas7 with NLS

<400> SEQUENCE: 6
atgcccaaga agaagcggaa ggtgtccaat ttcatcaaca tccacgtgct gatctcccac 60
tctccaagct gcctgaatag agacgatatg aacatgcaga aggacgccat ctttggcggc 120
aagcggagag tgaggatctc tagccagtcc ctgaagcggg ccatgagaaa gtctggctac 180
tatgcccaga atatcggcga gtcctctctg aggaccatcc acctggcaca gctgagggac 240

-continued gtgctgagac agaagctggg cgagcggttt gatcagaaga tcatcgacaa gacactggcc 300
ctgctgagcg gcaagtccgt ggatgaggcc gagaagatca gcgccgacgc agtgacccca 360
tgggtggtgg gagagatcgc atggttctgt gagcaggtgg ccaaggccga ggccgataat 420
ctggacgata agaagctgct gaaggtgctg aaggaggata tcgccgccat cagagtgaac 480
ctgcagcagg gagtggacat cgccctgagc ggcaggatgg ccacatccgg catgatgacc 540
gagctgggca aggtggacgg agcaatgtcc atcgcacacg ccatcaccac acaccaggtg 600
gactctgata tcgactggtt cacagccgtg gacgatctgc aggagcaggg aagcgcccac 660
ctgggaaccc aggagttcag ctccggcgtg ttttacagat atgccaatat caacctggca 720
cagctgcagg agaacctggg aggagcatcc agggagcagg ccctggagat cgccacacac 780
gtggtgcaca tgctggcaac cgaggtgcca ggagcaaagc agcgcaccta cgccgccttc 840
aatcctgccg atatggtcat ggtgaacttt tccgacatgc cactgtctat ggccaatgcc 900
ttcgagaagg ccgtgaaggc caaggatggc ttcctgcagc cttccatcca ggcctttaac 960
cagtactggg accgcgtggc caatggatat ggcctgaacg gagctgccgc ccagttttcc 1020
ctgtctgatg tggaccctat cacagcccag gtgaagcaga tgccaaccct ggagcagctg 1080
aagagctggg tgcggaacaa tggagaggca 1110

<210> SEQ ID NO 7
<211> LENGTH: 2775
<212> TYPE: DNA
<213> ORGANISM: Artificial Sequence
<220> FEATURE:
<223> OTHER INFORMATION: Synthetic sequence, modified Cas3 with BPNLS

<400> SEQUENCE: 7
aagcggactg ctgatggcag tgaatttgag tccccaaaga agaagagaaa ggtggaagaa 60
ccttttaaat atatatgcca ttactgggga aaatcctcaa aaagcttgac gaaaggaaat 120
gatattcatc tgttaattta tcattgcctt gatgttgctg ctgttgcaga ttgctggtgg 180
gatcaatcag tcgtactgca aaatactttt tgccgaaatg aaatgctatc aaaacagagg 240
gtgaaggcct ggctgttatt tttcattgct cttcatgata ttggaaagtt tgatatacga 300
ttccaatata aatcagcaga aagttggctg aaattaaatc ctgcaacgcc atcacttaat 360
ggtccatcaa cacaaatgtg ccgtaaattt aatcatggtg cagccggtct gtattggttt 420
aaccaggatt cactttcaga gcaatctctc ggggattttt tcagtttttt tgatgccgct 480
cctcatcctt atgagtcctg gtttccatgg gtagaggccg ttacaggaca tcatggtttt 540
atattacatt cccaggatca agataagtcg cgttgggaaa tgccagcttc tctggcatct 600
tatgctgcgc aagataaaca ggctcgtgag gagtggatat ctgtactgga agcattattt 660
ttaacgccag cggggttatc tataaacgat ataccacctg attgttcatc actgttagca 720
ggtttttgct cgcttgctga ctggttaggc tcctggacta caacgaatac ctttctgttt 780
aatgaggatg cgccttccga cataaatgct ctgagaacgt atttccagga ccgacagcag 840
gatgcgagcc gggtattgga gttgagtgga cttgtatcaa ataagcgatg ttatgaaggt 900
gttcatgcac tactggacaa tggctatcaa cccagacaat tacaggtgtt agttgatgct 960
cttccagtag ctcccgggct gacggtaata gaggcaccta caggctccgg taaaacggaa 1020
acagcgctgg cctatgcttg gaaacttatt gatcaacaaa ttgcggatag tgttattttt 1080
gccctcccaa cacaagctac cgcgaatgct atgcttacga gaatggaagc gagcgcgagc 1140

-continued cacttatttt catccccaaa tcttattctt gctcatggca attcacggtt taaccacctc 1200
tttcaatcaa taaaatcacg cgcgattact gaacaggggc aagaagaagc gtgggttcag 1260
tgttgtcagt ggttgtcaca aagcaataag aaagtgtttc ttgggcaaat cggcgtttgc 1320
acgattgatc aggtgttgat atcggtattg ccagttaaac accgctttat ccgtggtttg 1380
ggaattggtc gaagtgtttt aattgttgat gaagttcatg cttacgacac ctatatgaac 1440
ggcttgctgg aggcagtgct caaggctcag gctgatgtgg gagggagtgt tattcttctt 1500
tccgcaaccc taccaatgaa acaaaaacag aaacttctgg atacttatgg tctgcataca 1560
gatccagtgg aaaataactc cgcatatcca ctcattaact ggcgaggtgt gaatggtgcg 1620
caacgttttg atctgctagc tcatccagaa caactcccgc cccgcttttc gattcagcca 1680
gaacctattt gtttagctga catgttacct gaccttacga tgttagagcg aatgatcgca 1740
gcggcaaacg cgggtgcaca ggtctgtctt atttgcaatt tggttgacgt tgcacaagta 1800
tgctaccaac ggctaaagga gctaaataac acgcaagtag atatagattt gtttcatgcg 1860
cgctttacgc tgaacgatcg tcgtgaaaaa gagaatcgag ttattagcaa tttcggcaaa 1920
aatgggaagc gaaatgttgg acggatactt gtcgcaaccc aggtcgtgga acaatcactc 1980
gacgttgatt ttgattggtt aattactcag cattgtcctg cagatttgct tttccaacga 2040
ttgggccgtt tacatcgcca tcatcgcaaa tatcgtcccg ctggttttga gattcctgtt 2100
gccaccattt tgctgcctga tggcgagggt tacggacgac atgagcatat ttatagcaac 2160
gttagagtca tgtggcggac gcagcaacat attgaggagc ttaatggagc atccttattt 2220
ttccctgatg cttaccggca atggctggat agcatttacg atgatgcgga aatggatgag 2280
ccagaatggg tcggcaatgg catggataaa tttgaaagcg ccgagtgtga aaaaaggttc 2340
aaggctcgca aggtcctgca gtgggctgaa gaatatagct tgcaggataa cgatgaaacc 2400
attcttgcgg taacgaggga tggggaaatg agcctgccat tattgcctta tgtacaaacg 2460
tcttcaggta aacaactgct cgatggccag gtctacgagg acctaagtca tgaacagcag 2520
tatgaggcgc ttgcacttaa tcgcgtcaat gtacccttca cctggaaacg tagtttttct 2580
gaagtagtag atgaagatgg gttactttgg ctggaaggga aacagaatct ggatggatgg 2640
gtctggcagg gtaacagtat tgttattacc tatacagggg atgaagggat gaccagagtc 2700
atccctgcaa atcccaaaaa gcggactgct gatggcagtg aatttgagtc cccaaagaag 2760
aagagaaagg tggaa 2775

<210> SEQ ID NO 8
<211> LENGTH: 1617
<212> TYPE: DNA
<213> ORGANISM: Artificial Sequence
<220> FEATURE:
<223> OTHER INFORMATION: Synthetic sequence, modified Cse1 with BPNLS

<400> SEQUENCE: 8
aagcggactg ctgatggcag tgaatttgag tccccaaaga agaagagaaa ggtggaaaac 60
ctgctgattg acaactggat ccctgtgcgc ccacggaacg gaggaaaagt ccagattatt 120
aatctgcaga gcctgtactg ctcccgggat cagtggagac tgagcctgcc cagagacgat 180
atggagctgg ccgccctggc cctgctggtg tgcatcggcc agatcatcgc ccctgccaag 240
gacgatgtgg agttcaggca ccgcatcatg aaccctctga ccgaggatga gtttcagcag 300
ctgatcgccc catggatcga catgttctat ctgaatcacg ccgagcaccc cttcatgcag 360
acaaagggcg tgaaggccaa cgacgtgacc cccatggaga agctgctggc aggcgtgtcc 420

-continued ggagcaacaa attgcgcctt cgtgaaccag ccaggacagg gagaggccct gtgcggaggc 480
tgtaccgcca tcgccctgtt taatcaggca aaccaggcac ctggattcgg aggaggcttt 540
aagtctggac tgaggggagg aaccccagtg accacattcg tgagaggcat cgatctgagg 600
agcacagtgc tgctgaatgt gctgaccctg ccacggctgc agaagcagtt tcccaatgag 660
agccacacag agaaccagcc cacctggatc aagcctatca agtctaacga gagcatccct 720
gccagctcca tcggcttcgt gagaggcctg ttttggcagc cagcccacat cgagctgtgc 780
gaccccatcg gcatcggcaa gtgttcttgc tgtggccagg aaagcaatct gaggtacacc 840
ggcttcctga aggagaagtt cacctttaca gtgaacggcc tgtggcccca ccctcactct 900
ccatgtctgg tgacagtgaa gaagggcgag gtggaggaga agttcctggc ctttaccaca 960
tccgccccct cttggaccca gatcagcaga gtggtggtgg acaagatcat ccagaacgag 1020
aatggcaaca gagtggccgc cgtggtgaat cagttcagga acatcgcccc acagtctccc 1080
ctggagctga tcatgggcgg ctacaggaac aatcaggcca gcatcctgga gcggagacac 1140
gatgtgctga tgtttaatca gggctggcag cagtatggca atgtgatcaa cgagatcgtg 1200
acagtgggcc tgggctacaa gaccgccctg agaaaggccc tgtatacatt cgccgagggc 1260
tttaagaaca aggacttcaa gggagcaggc gtgagcgtgc acgagaccgc cgagaggcac 1320
ttttaccgcc agtccgagct gctgatcccc gatgtgctgg ccaatgtgaa cttctcccag 1380
gccgacgaag tgatcgccga tctgagggac aagctgcacc agctgtgcga gatgctgttt 1440
aaccagtctg tggccccata cgcccaccac cccaagctga tcagcacact ggccctggca 1500
agggccaccc tgtataagca cctgagggag ctgaagccac agggaggacc ttctaatgga 1560
aagcggactg ctgatggcag tgaatttgag tccccaaaga agaagagaaa ggtggaa 1617

<210> SEQ ID NO 9
<211> LENGTH: 591
<212> TYPE: DNA
<213> ORGANISM: Artificial Sequence
<220> FEATURE:
<223> OTHER INFORMATION: Synthetic sequence, modified Cse2 with BPNLS

<400> SEQUENCE: 9
aagcggactg ctgatggcag tgaatttgag tccccaaaga agaagagaaa ggtggaagcc 60
gatgagatcg acgcaatggc actgtacagg gcatggcagc agctggacaa cggatcttgc 120
gcacagatca ggcgcgtgag cgagcctgat gagctgaggg acatcccagc cttctatcgg 180
ctggtgcagc cctttggctg ggagaatcct agacaccagc aggccctgct gaggatggtg 240
ttttgtctga gcgccggcaa gaacgtgatc cggcaccagg acaagaagag cgagcagacc 300
acaggaatct ccctgggacg cgccctggcc aattccggcc ggatcaacga gcggagaatc 360
ttccagctga tcagggccga tcgcacagcc gacatggtgc agctgaggcg cctgctgacc 420
cacgcagagc ctgtgctgga ttggccactg atggcccgca tgctgacatg gtggggcaag 480
cgggagagac agcagctgct ggaggacttc gtgctgacca caaataagaa cgccaagcgg 540
actgctgatg gcagtgaatt tgagtcccca aagaagaaga gaaaggtgga a 591

<210> SEQ ID NO 10
<211> LENGTH: 783
<212> TYPE: DNA
<213> ORGANISM: Artificial Sequence
<220> FEATURE:
<223> OTHER INFORMATION: Synthetic sequence, modified Cas5 with BPNLS

<400> SEQUENCE: 10
aagcggactg ctgatggcag tgaatttgag tccccaaaga agaagagaaa ggtggaacgc 60
tcctacctga tcctgagact ggcaggacca atgcaggcat ggggacagcc tacattcgag 120
ggaaccaggc caacaggccg ctttcctacc cggtctggac tgctgggact gctgggagcc 180
tgcctgggca tccagaggga cgatacctct agcctgcagg ccctgagcga gtccgtgcag 240
ttcgccgtgc gctgtgatga gctgatcctg gacgataggc gcgtgtccgt gacaggcctg 300
cgggattacc acaccgtgct gggcgccaga gaggactata ggggcctgaa gtcccacgag 360
accatccaga catggcgcga gtacctgtgc gacgcctctt ttacagtggc cctgtggctg 420
accccacacg caacaatggt catcagcgag ctggagaagg ccgtgctgaa gccacggtac 480
accccctatc tgggccggag aagctgccct ctgacacacc cactgttcct gggcacctgt 540
caggcctccg atccccagaa ggccctgctg aactacgagc ctgtgggcgg cgacatctat 600
tctgaggaga gcgtgacagg ccaccacctg aagttcaccg ccagggatga gccaatgatc 660
acactgccaa ggcagtttgc atccagggag tggtatgtga tcaagggagg aatggacgtg 720
agccagaagc ggactgctga tggcagtgaa tttgagtccc caaagaagaa gagaaaggtg 780
gaa 783

<210> SEQ ID NO 11
<211> LENGTH: 708
<212> TYPE: DNA
<213> ORGANISM: Artificial Sequence
<220> FEATURE:
<223> OTHER INFORMATION: Synthetic sequence, modified Cas6 with BPNLS

<400> SEQUENCE: 11
aagcggactg ctgatggcag tgaatttgag tccccaaaga agaagagaaa ggtggaatac 60
ctgagcaaag tgatcatcgc aagggcatgg tccagggacc tgtatcagct gcaccagggc 120
ctgtggcacc tgttccctaa tagaccagat gccgccaggg acttcctgtt tcacgtggag 180
aagaggaaca cacccgaggg ctgtcacgtg ctgctgcagt ccgcccagat gcccgtgagc 240
accgcagtgg ccacagtgat caagaccaag caggtggagt tccagctgca agtgggcgtg 300
ccactgtact ttaggctgcg cgccaatccc atcaagacca tcctggataa ccagaagcgc 360
ctggactcta agggcaatat caagcggtgc agagtgcctc tgatcaagga ggccgagcag 420
atcgcctggc tgcagagaaa gctgggcaac gccgccaggg tggaggatgt gcaccctatc 480
agcgagcggc cacagtattt cagcggcgac ggcaagtccg gcaagatcca gaccgtgtgc 540
tttgagggcg tgctgaccat caacgatgcc ccagccctga tcgacctggt gcagcaggga 600
atcggacctg ctaagtcaat gggatgtggg ctgctgtcac tggcacctct gaagcggact 660
gctgatggca gtgaatttga gtccccaaag aagaagagaa aggtggaa 708

<210> SEQ ID NO 12
<211> LENGTH: 1200
<212> TYPE: DNA
<213> ORGANISM: Artificial Sequence
<220> FEATURE:
<223> OTHER INFORMATION: Synthetic sequence, modified Cas7 with BPNLS

<400> SEQUENCE: 12
aagcggactg ctgatggcag tgaatttgag tccccaaaga agaagagaaa ggtggaatcc 60
aatttcatca acatccacgt gctgatctcc cactctccaa gctgcctgaa tagagacgat 120
atgaacatgc agaaggacgc catctttggc ggcaagcgga gagtgaggat ctctagccag 180

```
tccctgaagc gggccatgag aaagtctggc tactatgccc agaatatcgg cgagtcctct    240

ctgaggacca tccacctggc acagctgagg gacgtgctga gacagaagct gggcgagcgg    300

tttgatcaga agatcatcga caagacactg gccctgctga gcggcaagtc cgtggatgag    360

gccgagaaga tcagcgccga cgcagtgacc ccatgggtgg tgggagagat cgcatggttc    420

tgtgagcagg tggccaaggc cgaggccgat aatctggacg ataagaagct gctgaaggtg    480

ctgaaggagg atatcgccgc catcagagtg aacctgcagc agggagtgga catcgccctg    540

agcggcagga tggccacatc cggcatgatg accgagctgg gcaaggtgga cggagcaatg    600

tccatcgcac acgccatcac cacacaccag gtggactctg atatcgactg gttcacagcc    660

gtggacgatc tgcaggagca gggaagcgcc cacctgggaa cccaggagtt cagctccggc    720

gtgttttaca gatatgccaa tatcaacctg gcacagctgc aggagaacct gggaggagca    780

tccagggagc aggccctgga gatcgccaca cacgtggtgc acatgctggc aaccgaggtg    840

ccaggagcaa agcagcgcac ctacgccgcc ttcaatcctg ccgatatggt catggtgaac    900

ttttccgaca tgccactgtc tatggccaat gccttcgaga aggccgtgaa ggccaaggat    960

ggcttcctgc agccttccat ccaggccttt aaccagtact gggaccgcgt ggccaatgga   1020

tatggcctga acggagctgc cgcccagttt tccctgtctg atgtggaccc tatcacagcc   1080

caggtgaagc agatgccaac cctggagcag ctgaagagct gggtgcggaa caatggagag   1140

gcaaagcgga ctgctgatgg cagtgaattt gagtccccaa agaagaagag aaaggtggaa   1200
```

<210> SEQ ID NO 13
<211> LENGTH: 2664
<212> TYPE: DNA
<213> ORGANISM: Escherichia coli

<400> SEQUENCE: 13

```
atggagccat tcaaatacat ctgccactac tgggggaaat catctaaaag cctgacaaag     60

gggaacgata tccacctgct gatctaccac tgcctggacg tggcagcagt ggcagattgt    120

tggtgggacc agagcgtggt gctgcagaat accttctgcc ggaacgagat gctgtccaag    180

cagagagtga aggcctggct gctgttcttt atcgccctgc acgatatcgg caagttcgac    240

atcaggtttc agtataagtc tgccgagagc tggctgaagc tgaatccagc cacaccctcc    300

ctgaacggcc cttctaccca gatgtgcagg aagttcaatc acggagcagc aggactgtac    360

tggtttaacc aggacagcct gtccgagcag tctctgggcg atttctttag cttctttgac    420

gccgcccctc acccatatga gagctggttc ccatgggtgg aggcagtgac aggacaccac    480

ggctttatcc tgcactccca ggaccaggat aagtctagat gggagatgcc agcatccctg    540

gcatcttacg cagcacagga taagcaggca agggaggagt ggatctctgt gctggaggcc    600

ctgttcctga ccccagcagg cctgagcatc aatgatatcc cacctgactg cagctccctg    660

ctggcaggct tttgtagcct ggcagactgg ctgggatcct ggaccacaac caatacattc    720

ctgtttaacg aggatgcccc ttctgacatc aacgccctgc gcacctactt ccaggatcgg    780

cagcaggacg ccagcagagt gctggagctg tctggcctgg tgagcaataa gcggtgctac    840

gagggagtgc acgcactgct ggataacggc tatcagccta gacagctgca ggtgctggtg    900

gacgcactgc ctgtggcacc aggactgaca gtgatcgagg caccaaccgg ctctggcaag    960

acagagaccg ccctggccta tgcctggaag ctgatcgatc agcagatcgc cgacagcgtg   1020

atcttcgcac tgccaacaca ggcaaccgca aatgccatgc tgaccaggat ggaggcctct   1080
```

-continued

```
gccagccacc tgttttctag ccctaacctg atcctggccc acggcaacag ccggttcaat   1140

cacctgtttc agagcatcaa gtccagagcc atcacagagc agggacagga ggaggcatgg   1200

gtgcagtgct gtcagtggct gtcccagtct aacaagaagg tgttcctggg ccagatcggc   1260

gtgtgcacca tcgatcaggt gctgatctcc gtgctgccag tgaagcacag gtttatcagg   1320

ggactgggaa tcggccgctc tgtgctgatc gtggatgagg tgcacgccta cgacacatat   1380

atgaacggcc tgctggaggc cgtgctgaag gcacaggcag acgtgggagg aagcgtgatc   1440

ctgctgtccg ccaccctgcc catgaagcag aagcagaagc tgctggatac atacggcctg   1500

cacaccgacc ctgtggagaa caatagcgcc tatccactga tcaattggag gggagtgaac   1560

ggagcacagc ggttcgacct gctggcacac ccagagcagc tgccaccacg gttttccatc   1620

cagcccgagc ctatctgcct ggccgatatg ctgcccgacc tgaccatgct ggagagaatg   1680

atcgctgccg ccaatgcagg agcacaggtg tgcctgatct gtaacctggt ggatgtggcc   1740

caggtgtgct accagcggct gaaggagctg aacaatacac aggtggacat cgatctgttc   1800

cacgccaggt ttaccctgaa tgaccggaga gagaaggaga accgcgtgat ctccaacttc   1860

ggcaagaatg gcaagagaaa cgtgggcagg atcctggtgg ccacacaggt ggtggagcag   1920

tctctggacg tggatttcga ctggctgatc acccagcact gccctgccga tctgctgttt   1980

cagcggctgg gcagactgca cagacaccac aggaagtaca ggccagcagg atttgagatc   2040

ccagtggcca caatcctgct gccagacgga gagggatacg gccggcacga gcacatctat   2100

agcaatgtgc gcgtgatgtg gcggacccag cagcacatcg aggagctgaa cggcgcctcc   2160

ctgttctttc ccgatgccta cagacagtgg ctggactcta tctatgacga tgccgagatg   2220

gatgagcctg agtgggtggg caatggcatg gacaagttcg agtccgccga gtgtgagaag   2280

cggttcaagg ccaggaaggt gctgcagtgg gccgaggagt acagcctgca ggataacgac   2340

gagacaatcc tggccgtgac cagggatggc gagatgtccc tgcccctgct gccttatgtg   2400

cagacatcct ctggcaagca gctgctggat ggccaggtgt acgaggacct gagccacgag   2460

cagcagtatg aggccctggc cctgaacagg gtgaatgtgc ccttcacctg gaagcgcagc   2520

ttttccgaag tggtggatga ggacggcctg ctgtggctgg agggcaagca gaatctggac   2580

ggctgggtgt ggcagggcaa ctccatcgtg attacctaca ccggagacga agggatgaca   2640

agagtgattc ctgctaaccc aaag                                          2664
```

<210> SEQ ID NO 14
<211> LENGTH: 1506
<212> TYPE: DNA
<213> ORGANISM: Escherichia coli

<400> SEQUENCE: 14

```
atgaatttgc ttattgataa ctggatccct gtacgcccgc gaaacggggg gaaagtccaa     60

atcataaatc tgcaatcgct atactgcagt agagatcagt ggcgattaag tttgccccgt    120

gacgatatgg aactggccgc tttagcactg ctggtttgca ttgggcaaat tatcgccccg    180

gcaaaagatg acgttgaatt tcgacatcgc ataatgaatc cgctcactga agatgagttt    240

caacaactca tcgcgccgtg gatagatatg ttctacctta atcacgcaga acatcccttt    300

atgcagacca aaggtgtcaa agcaaatgat gtgactccaa tggaaaaact gttggctggg    360

gtaagcggcg cgacgaattg tgcatttgtc aatcaaccgg ggcagggtga agcattatgt    420

ggtggatgca ctgcgattgc gttattcaac caggcgaatc aggcaccagg ttttggtggt    480

ggttttaaaa gcggtttacg tggaggaaca cctgtaacaa cgttcgtacg tgggatcgat    540
```

cttcgttcaa cggtgttact caatgtcctc acattacctc gtcttcaaaa acaatttcct 600
aatgaatcac atacggaaaa ccaacctacc tggattaaac ctatcaagtc caatgagtct 660
atacctgctt cgtcaattgg gtttgtccgt ggtctattct ggcaaccagc gcatattgaa 720
ttatgcgatc ccattgggat tggtaaatgt tcttgctgtg gacaggaaag caatttgcgt 780
tataccggtt ttcttaagga aaaatttacc tttacagtta atgggctatg gccccatccg 840
cattcccctt gtctggtaac agtcaagaaa ggggaggttg aggaaaaatt tcttgctttc 900
accacctccg caccatcatg gacacaaatc agccgagttg tggtagataa gattattcaa 960
aatgaaaatg gaaatcgcgt ggcggcggtt gtgaatcaat tcagaaatat tgcgccgcaa 1020
agtcctcttg aattgattat ggggggatat cgtaataatc aagcatctat tcttgaacgg 1080
cgtcatgatg tgttgatgtt taatcagggg tggcaacaat acggcaatgt gataaacgaa 1140
atagtgactg ttggtttggg atataaaaca gccttacgca aggcgttata tacctttgca 1200
gaagggttta aaaataaaga cttcaaaggg gccggagtct ctgttcatga gactgcagaa 1260
aggcatttct atcgacagag tgaattatta attcccgatg tactggcgaa tgttaatttt 1320
tcccaggctg atgaggtaat agctgattta cgagacaaac ttcatcaatt gtgtgaaatg 1380
ctatttaatc aatctgtagc tccctatgca catcatccta aattaataag cacattagcg 1440
cttgcccgcg ccacgctata caaacattta cgggagttaa aaccgcaagg agggccatca 1500
aatggc 1506

<210> SEQ ID NO 15
<211> LENGTH: 480
<212> TYPE: DNA
<213> ORGANISM: Escherichia coli

<400> SEQUENCE: 15
atggctgatg aaattgatgc aatggcttta tatcgagcct ggcaacaact ggataatgga 60
tcatgtgcgc aaattagacg tgtttcagaa cctgatgaat tacgcgatat ccctgcgttt 120
tataggctgg tgcaaccttt tggttgggaa aacccacgtc accagcaggc tcttttgcgc 180
atggtgtttt gcctgagcgc aggaaagaat gtcatccgac atcaggacaa aaaatcggag 240
caaacaacag gtatctcgtt gggaagagct ttagccaata gtggaagaat taacgagcgc 300
cgtatctttc aattaattcg ggctgacaga acagccgata tggtccagtt acgtcgatta 360
cttactcacg ccgaacccgt acttgactgg ccattaatgg ccaggatgtt gacctggtgg 420
ggaaagcgcg aacgccagca acttctggaa gattttgtat tgaccacaaa caaaaatgcg 480

<210> SEQ ID NO 16
<211> LENGTH: 672
<212> TYPE: DNA
<213> ORGANISM: Escherichia coli

<400> SEQUENCE: 16
atgagatctt atttgatctt gcggcttgct gggccaatgc aagcctgggg gcagccgacc 60
tttgaaggaa cgcgacctac cggaagattt ccgacccgaa gcgggttatt agggctactc 120
ggggcttgtc ttgggatcca acgtgatgat acttcttcat tacaggcgtt atcagagagt 180
gtgcaatttg cagtgcgctg cgatgaactc attcttgacg atcgtcgtgt gtctgtaacg 240
gggttgcgtg attaccatac agtccttgga gcgcgagaag attaccgtgg tttgaaaagt 300
catgaaacga ttcaaacatg gcgcgaatat ttatgtgatg cctcctttac cgtcgctctc 360

-continued

```
tggttaacac cccatgcaac gatggttatc tcagaacttg aaaaagcagt attaaagcct    420

cggtatacac cttacctggg gcggagaagt tgcccactaa cacacccgct tttttgggg    480

acatgtcagg catcggatcc tcagaaggcg ctattaaatt atgagcccgt tggcggcgat    540

atatatagtg aggaatcagt tacagggcat catttaaaat ttacggcgcg cgacgaaccg    600

atgatcacct tgcctcgaca atttgcttcc cgagaatggt atgtgattaa aggaggtatg    660

gatgtatctc ag                                                         672
```

<210> SEQ ID NO 17
<211> LENGTH: 597
<212> TYPE: DNA
<213> ORGANISM: Escherichia coli

<400> SEQUENCE: 17

```
atgtatctca gtaaagtcat cattgccagg gcctggagca gggatcttta ccaacttcac     60

cagggattat ggcatttatt tccaaacaga ccggatgctg ctcgtgattt tctttttcat    120

gttgagaagc gaaacacacc agaaggctgt catgttttat tgcagtcagc gcaaatgcct    180

gtttcaactg ccgttgcgac agtcattaaa actaaacagg ttgaatttca acttcaggtt    240

ggtgttccac tctattttcg gcttcgggca aatccgatca aaactattct cgacaatcaa    300

aagcgcctgg acagtaaagg gaatattaaa cgctgtcggg ttccgttaat aaaagaagca    360

gaacaaatcg cgtggttgca acgtaaattg ggcaatgcgg cgcgcgttga agatgtgcat    420

cccatatcgg aacggccaca gtatttttct ggtgatggta aaagtggaaa gatccaaacg    480

gtttgctttg aaggtgtgct caccatcaac gacgcgccag cgttaataga tcttgtacag    540

caaggtattg ggccagctaa atcgatggga tgtggcttgc tatctttggc tccactg       597
```

<210> SEQ ID NO 18
<211> LENGTH: 1086
<212> TYPE: DNA
<213> ORGANISM: Escherichia coli

<400> SEQUENCE: 18

```
tctaacttta tcaatattca tgttctgatc tctcacagcc cttcatgtct gaaccgcgac     60

gatatgaaca tgcagaaaga cgctattttc ggcggcaaaa gacgagtaag aatttcaagt    120

caaagcctta aacgtgcgat gcgtaaaagt ggttattacg cacaaaatat tggtgaatcc    180

agtctcagaa ccattcatct tgcacaatta cgtgatgttc ttcggcaaaa acttggtgaa    240

cgttttgacc aaaaaatcat cgataagaca ttagcgctgc tctccggtaa atcagttgat    300

gaagccgaaa agatttctgc cgatgcggtt actccctggg ttgtgggaga aatagcctgg    360

ttctgtgagc aggttgcaaa agcagaggct gataatctgg atgataaaaa gctgctcaaa    420

gttcttaagg aagatattgc cgccatacgt gtgaatttac agcagggtgt tgatattgcg    480

cttagtggaa gaatggcaac cagcggcatg atgactgagt tgggaaaagt tgatggtgca    540

atgtccattg cgcatgcgat cactactcat caggttgatt ctgatattga ctggttcacc    600

gctgtagatg atttacagga acaaggttct gcacatctgg gaactcagga attttcatcg    660

ggtgtttttt atcgttatgc caacattaac ctcgctcaac ttcaggaaaa tttaggtggt    720

gcctccaggg agcaggctct ggaaattgca acccatgttg ttcatatgct ggcaacagag    780

gtccctggag caaaacagcg tacttatgcc gcttttaacc ctgcggatat ggtaatggtt    840

aatttctccg atatgccact ttctatggca aatgcttttg aaaaagcggt taaagcgaaa    900

gatggctttt tgcaaccgtc tatacaggcg tttaatcaat attgggatcg cgttgccaat    960
```

ggatatggtc tgaacggagc tgctgcgcaa ttcagcttat ctgatgtaga cccaattact 1020
gctcaagtta aacaaatgcc tactttagaa cagttaaaat cctgggttcg taataatggc 1080
gaggcg 1086

<210> SEQ ID NO 19
<211> LENGTH: 39
<212> TYPE: DNA
<213> ORGANISM: Artificial Sequence
<220> FEATURE:
<223> OTHER INFORMATION: Synthetic sequence, target (CCR5)

<400> SEQUENCE: 19
tcaagtccaa tctatgacat caattattat acatcggag 39

<210> SEQ ID NO 20
<211> LENGTH: 50
<212> TYPE: DNA
<213> ORGANISM: Artificial Sequence
<220> FEATURE:
<223> OTHER INFORMATION: Synthetic sequence, reporter vector insert1
(CCR5)

<400> SEQUENCE: 20
gtcggattca agtccaatct atgacatcaa ttattataca tcggagaggt 50

<210> SEQ ID NO 21
<211> LENGTH: 50
<212> TYPE: DNA
<213> ORGANISM: Artificial Sequence
<220> FEATURE:
<223> OTHER INFORMATION: Synthetic sequence, reporter vector insert2
(CCR5)

<400> SEQUENCE: 21
cggtacctct ccgatgtata ataattgatg tcatagattg gacttgaatc 50

<210> SEQ ID NO 22
<211> LENGTH: 35
<212> TYPE: DNA
<213> ORGANISM: Artificial Sequence
<220> FEATURE:
<223> OTHER INFORMATION: Synthetic sequence, target (E. coli)

<400> SEQUENCE: 22
aagagcacaa atatcatcgc tcaaaccact tacgg 35

<210> SEQ ID NO 23
<211> LENGTH: 46
<212> TYPE: DNA
<213> ORGANISM: Artificial Sequence
<220> FEATURE:
<223> OTHER INFORMATION: Synthetic sequence, reporter vector insert1
(E. coli)

<400> SEQUENCE: 23
gtcggataag agcacaaata tcatcgctca aaccacttac ggaggt 46

<210> SEQ ID NO 24
<211> LENGTH: 46
<212> TYPE: DNA
<213> ORGANISM: Artificial Sequence
<220> FEATURE:
<223> OTHER INFORMATION: Synthetic sequence, reporter vector insert2
(E. coli)

<400> SEQUENCE: 24
cggtacctcc gtaagtggtt tgagcgatga tatttgtgct cttatc 46

<210> SEQ ID NO 25
<211> LENGTH: 36
<212> TYPE: DNA
<213> ORGANISM: Artificial Sequence
<220> FEATURE:
<223> OTHER INFORMATION: Synthetic sequence, crRNA insert1 (CCR5)

<400> SEQUENCE: 25
accgtccaat ctatgacatc aattattata catcgg 36

<210> SEQ ID NO 26
<211> LENGTH: 36
<212> TYPE: DNA
<213> ORGANISM: Artificial Sequence
<220> FEATURE:
<223> OTHER INFORMATION: Synthetic sequence, crRNA insert 2(CCR5)

<400> SEQUENCE: 26
acacccgatg tataataatt gatgtcatag attgga 36

<210> SEQ ID NO 27
<211> LENGTH: 36
<212> TYPE: DNA
<213> ORGANISM: Artificial Sequence
<220> FEATURE:
<223> OTHER INFORMATION: Synthetic sequence, crRNA insert1 (E.coli)

<400> SEQUENCE: 27
accgagcaca aatatcatcg ctcaaaccac ttacgg 36

<210> SEQ ID NO 28
<211> LENGTH: 36
<212> TYPE: DNA
<213> ORGANISM: Artificial Sequence
<220> FEATURE:
<223> OTHER INFORMATION: Synthetic sequence, crRNA insert 2(E.coli)

<400> SEQUENCE: 28
acacccgtaa gtggtttgag cgatgatatt tgtgct 36

<210> SEQ ID NO 29
<211> LENGTH: 36
<212> TYPE: DNA
<213> ORGANISM: Artificial Sequence
<220> FEATURE:
<223> OTHER INFORMATION: Synthetic sequence, crRNA insert 1(EMX1)

<400> SEQUENCE: 29
accgcaggcc aatggggagg acatcgatgt cacctc 36

<210> SEQ ID NO 30
<211> LENGTH: 36
<212> TYPE: DNA
<213> ORGANISM: Artificial Sequence
<220> FEATURE:
<223> OTHER INFORMATION: Synthetic sequence, crRNA insert 2(EMX1)

<400> SEQUENCE: 30
acacgaggtg acatcgatgt cctccccatt ggcctg 36

<210> SEQ ID NO 31
<211> LENGTH: 5701

<212> TYPE: DNA
<213> ORGANISM: Artificial Sequence
<220> FEATURE:
<223> OTHER INFORMATION: Synthetic sequence, reporter vector (CCR5)

<400> SEQUENCE: 31
ggcctaactg gccggtacct agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctggt ttagtgaacc 600
gtcagatccg ctagcgctac cggactcaga tctcgagctc aagcttggca atccggtact 660
gttggtaaag ccaccatgga agatgccaaa aacattaaga agggcccagc gccattctac 720
ccactcgaag acgggaccgc cggcgagcag ctgcacaaag ccatgaagcg ctacgccctg 780
gtgcccggca ccatcgcctt taccgacgca catatcgagg tggacattac ctacgccgag 840
tacttcgaga tgagcgttcg gctggcagaa gctatgaagc gctatgggct gaatacaaac 900
catcggatcg tggtgtgcag cgagaatagc ttgcagttct tcatgcccgt gttgggtgcc 960
ctgttcatcg gtgtggctgt ggccccagct aacgacatct acaacgagcg cgagctgctg 1020
aacagcatgg gcatcagcca gcccaccgtc gtattcgtga gcaagaaagg gctgcaaaag 1080
atcctcaacg tgcaaaagaa gctaccgatc atacaaaaga tcatcatcat ggatagcaag 1140
accgactacc agggcttcca aagcatgtac accttcgtga cttcccattt gccacccggc 1200
ttcaacgagt acgacttcgt gcccgagagc ttcgaccggg acaaaaccat cgccctgatc 1260
atgaacagta gtggcagtac cggattgccc aagggcgtag ccctaccgca ccgcaccgct 1320
tgtgtccgat tcagtcatgc ccgcgacccc atcttcggca accagatcat ccccgacacc 1380
gctatcctca gcgtggtgcc atttcaccac ggcttcggca tgttcaccac gctgggctac 1440
ttgatctgcg gctttcgggt cgtgctcatg taccgcttcg aggaggagct attcttgcgc 1500
agcttgcaag actataagat tcaatctgcc ctgctggtgc ccacactatt tagcttcttc 1560
gctaagagca ctctcatcga caagtacgac ctaagcaact tgcacgagat cgccagcggc 1620
ggggcgccgc tcagcaagga ggtaggtgag gccgtggcca aacgcttcca cctaccaggc 1680
atccgccagg gctacggcct gacagaaaca accagcgcca ttctgatcac cccccgaaggg 1740 gacgacaagc ctggcgcagt aggcaaggtg gtgcccttct tcgaggctaa ggtggtggac 1800
ttggactagg gtctctgtcg gattcaagtc caatctatga catcaattat tatacatcgg 1860
agaggtaccg tgagacctag gagcgcgagc tgctgaacag catgggcatc agccagccca 1920
ccgtcgtatt cgtgagcaag aaagggctgc aaaagatcct caacgtgcaa aagaagctac 1980
cgatcataca aaagatcatc atcatggata gcaagaccga ctaccagggc ttccaaagca 2040
tgtacacctt cgtgacttcc catttgccac ccggcttcaa cgagtacgac ttcgtgcccg 2100
agagcttcga ccgggacaaa accatcgccc tgatcatgaa cagtagtggc agtaccggat 2160

-continued

```
tgcccaaggg cgtagcccta ccgcaccgca ccgcttgtgt ccgattcagt catgcccgcg   2220
accccatctt cggcaaccag atcatccccg acaccgctat cctcagcgtg gtgccatttc   2280
accacggctt cggcatgttc accacgctgg gctacttgat ctgcggcttt cgggtcgtgc   2340
tcatgtaccg cttcgaggag gagctattct tgcgcagctt gcaagactat aagattcaat   2400
ctgccctgct ggtgcccaca ctatttagct tcttcgctaa gagcactctc atcgacaagt   2460
acgacctaag caacttgcac gagatcgcca gcggcggggc gccgctcagc aaggaggtag   2520
gtgaggccgt ggccaaacgc ttccacctac caggcatccg ccagggctac ggcctgacag   2580
aaacaaccag cgccattctg atcacccccg aaggggacga caagcctggc gcagtaggca   2640
aggtggtgcc cttcttcgag gctaaggtgg tggacttgga caccggtaag acactgggtg   2700
tgaaccagcg cggcgagctg tgcgtccgtg gccccatgat catgagcggc tacgttaaca   2760
accccgaggc tacaaacgct ctcatcgaca aggacggctg gctgcacagc ggcgacatcg   2820
cctactggga cgaggacgag cacttcttca tcgtggaccg gctgaagagc ctgatcaaat   2880
acaagggcta ccaggtagcc ccagccgaac tggagagcat cctgctgcaa caccccaaca   2940
tcttcgacgc cggggtcgcc ggcctgcccg acgacgatgc cggcgagctg cccgccgcag   3000
tcgtcgtgct ggaacacggt aaaaccatga ccgagaagga gatcgtggac tatgtggcca   3060
gccaggttac aaccgccaag aagctgcgcg gtggtgttgt gttcgtggac gaggtgccta   3120
aaggactgac cggcaagttg gacgcccgca agatccgcga gattctcatt aaggccaaga   3180
agggcggcaa gatcgccgtg aattcttaac tgcagtctag agtcggggcg gccggccgct   3240
tcgagcagac atgataagat acattgatga gtttggacaa accacaacta gaatgcagtg   3300
aaaaaaatgc tttatttgtg aaatttgtga tgctattgct ttatttgtaa ccattataag   3360
ctgcaataaa caagttaaca acaacaattg cattcatttt atgtttcagg ttcaggggga   3420
ggtgtgggag gtttttttaaa gcaagtaaaa cctctacaaa tgtggtaaaa tcgataagga   3480
tccgtcgacc gatgcccttg agagccttca acccagtcag ctccttccgg tgggcgcggg   3540
gcatgactat cgtcgccgca cttatgactg tcttctttat catgcaactc gtaggacagg   3600
tgccggcagc gctcttccgc ttcctcgctc actgactcgc tgcgctcggt cgttcggctg   3660
cggcgagcgg tatcagctca ctcaaaggcg gtaatacggt tatccacaga atcaggggat   3720
aacgcaggaa agaacatgtg agcaaaaggc cagcaaaagg ccaggaaccg taaaaaggcc   3780
gcgttgctgg cgtttttcca taggctccgc ccccctgacg agcatcacaa aaatcgacgc   3840
tcaagtcaga ggtggcgaaa cccgacagga ctataaagat accaggcgtt tccccctgga   3900
agctccctcg tgcgctctcc tgttccgacc ctgccgctta ccggatacct gtccgccttt   3960
ctcccttcgg gaagcgtggc gctttctcat agctcacgct gtaggtatct cagttcggtg   4020
taggtcgttc gctccaagct gggctgtgtg cacgaacccc ccgttcagcc cgaccgctgc   4080
gccttatccg gtaactatcg tcttgagtcc aacccggtaa gacacgactt atcgccactg   4140
gcagcagcca ctggtaacag gattagcaga gcgaggtatg taggcggtgc tacagagttc   4200
ttgaagtggt ggcctaacta cggctacact agaagaacag tatttggtat ctgcgctctg   4260
ctgaagccag ttaccttcgg aaaaagagtt ggtagctctt gatccggcaa acaaaccacc   4320
gctggtagcg gtggtttttt tgtttgcaag cagcagatta cgcgcagaaa aaaaggatct   4380
caagaagatc ctttgatctt ttctacgggg tctgacgctc agtggaacga aaactcacgt   4440
taagggattt tggtcatgag attatcaaaa aggatcttca cctagatcct tttaaattaa   4500
aaatgaagtt ttaaatcaat ctaaagtata tatgagtaaa cttggtctga cagcggccgc   4560
```

aaatgctaaa ccactgcagt ggttaccagt gcttgatcag tgaggcaccg atctcagcga 4620
tctgcctatt tcgttcgtcc atagtggcct gactccccgt cgtgtagatc actacgattc 4680
gtgagggctt accatcaggc cccagcgcag caatgatgcc gcgagagccg cgttcaccgg 4740
cccccgattt gtcagcaatg aaccagccag cagggagggc cgagcgaaga agtggtcctg 4800
ctactttgtc cgcctccatc cagtctatga gctgctgtcg tgatgctaga gtaagaagtt 4860
cgccagtgag tagtttccga agagttgtgg ccattgctac tggcatcgtg gtatcacgct 4920
cgtcgttcgg tatggcttcg ttcaactctg gttcccagcg gtcaagccgg gtcacatgat 4980
cacccatatt atgaagaaat gcagtcagct ccttagggcc tccgatcgtt gtcagaagta 5040
agttggccgc ggtgttgtcg ctcatggtaa tggcagcact acacaattct cttaccgtca 5100
tgccatccgt aagatgcttt tccgtgaccg gcgagtactc aaccaagtcg ttttgtgagt 5160
agtgtatacg gcgaccaagc tgctcttgcc cggcgtctat acgggacaac accgcgccac 5220
atagcagtac tttgaaagtg ctcatcatcg ggaatcgttc ttcggggcgg aaagactcaa 5280
ggatcttgcc gctattgaga tccagttcga tatagcccac tcttgcaccc agttgatctt 5340
cagcatcttt tactttcacc agcgtttcgg ggtgtgcaaa aacaggcaag caaaatgccg 5400
caaagaaggg aatgagtgcg acacgaaaat gttggatgct catactcgtc ctttttcaat 5460
attattgaag catttatcag ggttactagt acgtctctca aggataagta agtaatatta 5520
aggtacggga ggtattggac aggccgcaat aaaatatctt tattttcatt acatctgtgt 5580
gttggttttt tgtgtgaatc gatagtacta acatacgctc tccatcaaaa caaaacgaaa 5640
caaaacaaac tagcaaaata ggctgtcccc agtgcaagtg caggtgccag aacatttctc 5700
t 5701

<210> SEQ ID NO 32
<211> LENGTH: 5697
<212> TYPE: DNA
<213> ORGANISM: Artificial Sequence
<220> FEATURE:
<223> OTHER INFORMATION: Synthetic sequence, reporter vector (E. coli)

<400> SEQUENCE: 32
ggcctaactg gccggtacct agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctggt ttagtgaacc 600
gtcagatccg ctagcgctac cggactcaga tctcgagctc aagcttggca atccggtact 660
gttggtaaag ccaccatgga agatgccaaa aacattaaga agggcccagc gccattctac 720
ccactcgaag acgggaccgc cggcgagcag ctgcacaaag ccatgaagcg ctacgccctg 780
gtgcccggca ccatcgcctt taccgacgca catatcgagg tggacattac ctacgccgag 840

-continued

```
tacttcgaga tgagcgttcg gctggcagaa gctatgaagc gctatgggct gaatacaaac    900
catcggatcg tggtgtgcag cgagaatagc ttgcagttct tcatgcccgt gttgggtgcc    960
ctgttcatcg gtgtggctgt ggccccagct aacgacatct acaacgagcg cgagctgctg   1020
aacagcatgg gcatcagcca gcccaccgtc gtattcgtga gcaagaaagg gctgcaaaag   1080
atcctcaacg tgcaaaagaa gctaccgatc atacaaaaga tcatcatcat ggatagcaag   1140
accgactacc agggcttcca aagcatgtac accttcgtga cttcccattt gccacccggc   1200
ttcaacgagt acgacttcgt gcccgagagc ttcgaccggg acaaaaccat cgccctgatc   1260
atgaacagta gtggcagtac cggattgccc aagggcgtag ccctaccgca ccgcaccgct   1320
tgtgtccgat tcagtcatgc ccgcgacccc atcttcggca accagatcat ccccgacacc   1380
gctatcctca gcgtggtgcc atttcaccac ggcttcggca tgttcaccac gctgggctac   1440
ttgatctgcg gctttcgggt cgtgctcatg taccgcttcg aggaggagct attcttgcgc   1500
agcttgcaag actataagat tcaatctgcc ctgctggtgc ccacactatt tagcttcttc   1560
gctaagagca ctctcatcga caagtacgac ctaagcaact tgcacgagat cgccagcggc   1620
ggggcgccgc tcagcaagga ggtaggtgag gccgtggcca aacgcttcca cctaccaggc   1680
atccgccagg gctacggcct gacagaaaca accagcgcca ttctgatcac ccccgaaggg   1740
gacgacaagc ctggcgcagt aggcaaggtg gtgcccttct tcgaggctaa ggtggtggac   1800
ttggactagg gtctctgtcg gataagagca caaatatcat cgctcaaacc acttacggag   1860
gtaccgtgag acctaggagc gcgagctgct gaacagcatg ggcatcagcc agcccaccgt   1920
cgtattcgtg agcaagaaag ggctgcaaaa gatcctcaac gtgcaaaaga agctaccgat   1980
catacaaaag atcatcatca tggatagcaa gaccgactac cagggcttcc aaagcatgta   2040
caccttcgtg acttcccatt tgccacccgg cttcaacgag tacgacttcg tgcccgagag   2100
cttcgaccgg gacaaaacca tcgccctgat catgaacagt agtggcagta ccggattgcc   2160
caagggcgta gccctaccgc accgcaccgc ttgtgtccga ttcagtcatg cccgcgaccc   2220
catcttcggc aaccagatca tccccgacac cgctatcctc agcgtggtgc catttcacca   2280
cggcttcggc atgttcacca cgctgggcta cttgatctgc ggctttcggg tcgtgctcat   2340
gtaccgcttc gaggaggagc tattcttgcg cagcttgcaa gactataaga ttcaatctgc   2400
cctgctggtg cccacactat ttagcttctt cgctaagagc actctcatcg acaagtacga   2460
cctaagcaac ttgcacgaga tcgccagcgg cggggcgccg ctcagcaagg aggtaggtga   2520
ggccgtggcc aaacgcttcc acctaccagg catccgccag ggctacggcc tgacagaaac   2580
aaccagcgcc attctgatca cccccgaagg ggacgacaag cctggcgcag taggcaaggt   2640
ggtgcccttc ttcgaggcta aggtggtgga cttggacacc ggtaagacac tgggtgtgaa   2700
ccagcgcggc gagctgtgcg tccgtggccc catgatcatg agcggctacg ttaacaaccc   2760
cgaggctaca aacgctctca tcgacaagga cggctggctg cacagcggcg acatcgccta   2820
ctgggacgag gacgagcact tcttcatcgt ggaccggctg aagagcctga tcaaatacaa   2880
gggctaccag gtagccccag ccgaactgga gagcatcctg ctgcaacacc ccaacatctt   2940
cgacgccggg gtcgccggcc tgcccgacga cgatgccggc gagctgcccg ccgcagtcgt   3000
cgtgctggaa cacggtaaaa ccatgaccga gaaggagatc gtggactatg tggccagcca   3060
ggttacaacc gccaagaagc tgcgcggtgg tgttgtgttc gtggacgagg tgcctaaagg   3120
actgaccggc aagttggacg cccgcaagat ccgcgagatt ctcattaagg ccaagaaggg   3180
cggcaagatc gccgtgaatt cttaactgca gtctagagtc ggggcggccg gccgcttcga   3240
```

```
gcagacatga taagatacat tgatgagttt ggacaaacca caactagaat gcagtgaaaa   3300
aaatgcttta tttgtgaaat ttgtgatgct attgctttat ttgtaaccat tataagctgc   3360
aataaacaag ttaacaacaa caattgcatt cattttatgt ttcaggttca gggggaggtg   3420
tgggaggttt tttaaagcaa gtaaaacctc tacaaatgtg gtaaaatcga taaggatccg   3480
tcgaccgatg cccttgagag ccttcaaccc agtcagctcc ttccggtggg cgcggggcat   3540
gactatcgtc gccgcactta tgactgtctt ctttatcatg caactcgtag gacaggtgcc   3600
ggcagcgctc ttccgcttcc tcgctcactg actcgctgcg ctcggtcgtt cggctgcggc   3660
gagcggtatc agctcactca aaggcggtaa tacggttatc cacagaatca ggggataacg   3720
caggaaagaa catgtgagca aaaggccagc aaaaggccag gaaccgtaaa aaggccgcgt   3780
tgctggcgtt tttccatagg ctccgccccc ctgacgagca tcacaaaaat cgacgctcaa   3840
gtcagaggtg gcgaaacccg acaggactat aaagatacca ggcgtttccc cctggaagct   3900
ccctcgtgcg ctctcctgtt ccgaccctgc cgcttaccgg atacctgtcc gcctttctcc   3960
cttcgggaag cgtggcgctt tctcatagct cacgctgtag gtatctcagt tcggtgtagg   4020
tcgttcgctc caagctgggc tgtgtgcacg aaccccccgt tcagcccgac cgctgcgcct   4080
tatccggtaa ctatcgtctt gagtccaacc cggtaagaca cgacttatcg ccactggcag   4140
cagccactgg taacaggatt agcagagcga ggtatgtagg cggtgctaca gagttcttga   4200
agtggtggcc taactacggc tacactagaa gaacagtatt tggtatctgc gctctgctga   4260
agccagttac cttcggaaaa agagttggta gctcttgatc cggcaaacaa accaccgctg   4320
gtagcggtgg tttttttgtt tgcaagcagc agattacgcg cagaaaaaaa ggatctcaag   4380
aagatccttt gatcttttct acggggtctg acgctcagtg gaacgaaaac tcacgttaag   4440
ggattttggt catgagatta tcaaaaagga tcttcaccta gatcctttta aattaaaaat   4500
gaagttttaa atcaatctaa agtatatatg agtaaacttg gtctgacagc ggccgcaaat   4560
gctaaaccac tgcagtggtt accagtgctt gatcagtgag gcaccgatct cagcgatctg   4620
cctatttcgt tcgtccatag tggcctgact ccccgtcgtg tagatcacta cgattcgtga   4680
gggcttacca tcaggcccca gcgcagcaat gatgccgcga gagccgcgtt caccggcccc   4740
cgatttgtca gcaatgaacc agccagcagg gagggccgag cgaagaagtg gtcctgctac   4800
tttgtccgcc tccatccagt ctatgagctg ctgtcgtgat gctagagtaa gaagttcgcc   4860
agtgagtagt ttccgaagag ttgtggccat tgctactggc atcgtggtat cacgctcgtc   4920
gttcggtatg gcttcgttca actctggttc ccagcggtca agccgggtca catgatcacc   4980
catattatga agaaatgcag tcagctcctt agggcctccg atcgttgtca gaagtaagtt   5040
ggccgcggtg ttgtcgctca tggtaatggc agcactacac aattctctta ccgtcatgcc   5100
atccgtaaga tgcttttccg tgaccggcga gtactcaacc aagtcgtttt gtgagtagtg   5160
tatacggcga ccaagctgct cttgcccggc gtctatacgg gacaacaccg cgccacatag   5220
cagtactttg aaagtgctca tcatcgggaa tcgttcttcg gggcggaaag actcaaggat   5280
cttgccgcta ttgagatcca gttcgatata gcccactctt gcacccagtt gatcttcagc   5340
atcttttact ttcaccagcg tttcggggtg tgcaaaaaca ggcaagcaaa atgccgcaaa   5400
gaagggaatg agtgcgacac gaaaatgttg gatgctcata ctcgtccttt ttcaatatta   5460
ttgaagcatt tatcagggtt actagtacgt ctctcaagga taagtaagta atattaaggt   5520
acgggaggta ttggacaggc cgcaataaaa tatctttatt ttcattacat ctgtgtgttg   5580
```

gttttttgtg tgaatcgata gtactaacat acgctctcca tcaaaacaaa acgaaacaaa 5640
acaaactagc aaaataggct gtccccagtg caagtgcagg tgccagaaca tttctct 5697

<210> SEQ ID NO 33
<211> LENGTH: 3391
<212> TYPE: DNA
<213> ORGANISM: Artificial Sequence
<220> FEATURE:
<223> OTHER INFORMATION: Synthetic sequence, crRNA vector (CCR5)

<400> SEQUENCE: 33
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgtcctt ctagtgtagc 1320
cgtagttagg ccaccacttc aagaactctg tagcaccgcc tacatacctc gctctgctaa 1380
tcctgttacc agtggctgct gccagtggcg ataagtcgtg tcttaccggg ttggactcaa 1440
gacgatagtt accggataag gcgcagcggt cgggctgaac ggggggttcg tgcacacagc 1500
ccagcttgga gcgaacgacc tacaccgaac tgagatacct acagcgtgag ctatgagaaa 1560
gcgccacgct tcccgaaggg agaaaggcgg acaggtatcc ggtaagcggc agggtcggaa 1620
caggagagcg cacgagggag cttccagggg gaaacgcctg gtatctttat agtcctgtcg 1680
ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtt ctttcctgcg ttatcccctg attctgtgga taaccgtatt accgcctttg 1860
agtgagctga taccgctcgc cgcagccgaa cgaccgagcg cagcgagtca gtgagcgagg 1920
aagcggaaga gcgcccaata cgcaaaccgc ctctccccgc gcgttggccg attcattaat 1980

```
gcagctggca cgacaggttt cccgactgga aagcgggcag tgagcgcaac gcaattaatg   2040

tgagttagct cactcattag gcaccccagg ctttacactt tatgcttccg gctcgtatgt   2100

tgtgtggaat tgtgagcgga taacaatttc acacaggaaa cagctatgac catgattacg   2160

ccaagcgcgc aattaaccct cactaaaggg aacaaaagct gggtaccggg ccccccctcg   2220

aggtcgacgg tatcgataag cttgatatcg aattgacgtg aattcttccc atgattcctt   2280

catatttgca tatacgatac aaggctgtta gagagataat tggaattaat ttgactgtaa   2340

acacaaagat attagtacaa aatacgtgac gtagaaagta ataatttctt gggtagtttg   2400

cagttttaaa attatgtttt aaaatggact atcatatgct taccgtaact tgaaagtatt   2460

tcgatttctt ggctttatat atcttgtgga aaggacgtgg atgtgttgtt tgtgtgatac   2520

tataaagttg gtagattgtg actggcttaa aaaatcatta attaataata ggttatgttt   2580

agagtgttcc ccgcgccagc ggggataaac cgtccaatct atgacatcaa ttattataca   2640

tcgggtgttc cccgcgccag cggggataaa ccgtttttttg aattcctgca gcccgggggga   2700

tccactagtt ctagagcggc cgccaccgcg gtggagctcc aattcgccct atagtgagtc   2760

gtattacgcg cgctcactgg ccgtcgtttt acaacgtcgt gactgggaaa accctggcgt   2820

tacccaactt aatcgccttg cagcacatcc ccctttcgcc agctggcgta atagcgaaga   2880

ggcccgcacc gatcgccctt cccaacagtt gcgcagcctg aatggcgaat gggacgcgcc   2940

ctgtagcggc gcattaagcg cggcgggtgt ggtggttacg cgcagcgtga ccgctacact   3000

tgccagcgcc ctagcgcccg ctcctttcgc tttcttccct tcctttctcg ccacgttcgc   3060

cggctttccc cgtcaagctc taaatcgggg gctcccttta gggttccgat ttagtgcttt   3120

acggcacctc gaccccaaaa aacttgatta gggtgatggt tcacgtagtg ggccatcgcc   3180

ctgatagacg gtttttcgcc ctttgacgtt ggagtccacg ttctttaata gtggactctt   3240

gttccaaact ggaacaacac tcaaccctat ctcggtctat tcttttgatt tataagggat   3300

tttgccgatt tcggcctatt ggttaaaaaa tgagctgatt taacaaaaat ttaacgcgaa   3360

ttttaacaaa atattaacgc ttacaattta g                                  3391


<210> SEQ ID NO 34
<211> LENGTH: 3391
<212> TYPE: DNA
<213> ORGANISM: Artificial Sequence
<220> FEATURE:
<223> OTHER INFORMATION: Synthetic sequence,   crRNA vector (E. coli)

<400> SEQUENCE: 34

gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg cttttttgca caacatgggg gatcatgtaa    600
```

-continued

```
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccggg ccccccctcg   2220
aggtcgacgg tatcgataag cttgatatcg aattgacgtg aattcttccc atgattcctt   2280
catatttgca tatacgatac aaggctgtta gagagataat tggaattaat ttgactgtaa   2340
acacaaagat attagtacaa aatacgtgac gtagaaagta ataatttctt gggtagtttg   2400
cagttttaaa attatgtttt aaaatggact atcatatgct taccgtaact tgaaagtatt   2460
tcgatttctt ggctttatat atcttgtgga aaggacgtgg atgtgttgtt tgtgtgatac   2520
tataaagttg gtagattgtg actggcttaa aaaatcatta attaataata ggttatgttt   2580
agagtgttcc ccgcgccagc ggggataaac cgagcacaaa tatcatcgct caaaccactt   2640
acgggtgttc cccgcgccag cggggataaa ccgttttttg aattcctgca gcccggggga   2700
tccactagtt ctagagcggc cgccaccgcg gtggagctcc aattcgccct atagtgagtc   2760
gtattacgcg cgctcactgg ccgtcgtttt acaacgtcgt gactgggaaa accctggcgt   2820
tacccaactt aatcgccttg cagcacatcc ccctttcgcc agctggcgta atagcgaaga   2880
ggcccgcacc gatcgccctt cccaacagtt gcgcagcctg aatggcgaat gggacgcgcc   2940
ctgtagcggc gcattaagcg cggcgggtgt ggtggttacg cgcagcgtga ccgctacact   3000
```

tgccagcgcc ctagcgcccg ctcctttcgc tttcttccct tcctttctcg ccacgttcgc 3060
cggctttccc cgtcaagctc taaatcgggg gctcccttta gggttccgat ttagtgcttt 3120
acggcacctc gaccccaaaa aacttgatta gggtgatggt tcacgtagtg ggccatcgcc 3180
ctgatagacg gtttttcgcc ctttgacgtt ggagtccacg ttctttaata gtggactctt 3240
gttccaaact ggaacaacac tcaaccctat ctcggtctat tcttttgatt tataagggat 3300
tttgccgatt tcggcctatt ggttaaaaaa tgagctgatt taacaaaaat ttaacgcgaa 3360
ttttaacaaa atattaacgc ttacaattta g 3391

<210> SEQ ID NO 35
<211> LENGTH: 3391
<212> TYPE: DNA
<213> ORGANISM: Artificial Sequence
<220> FEATURE:
<223> OTHER INFORMATION: Synthetic sequence, crRNA vector (EMX1)

<400> SEQUENCE: 35
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgtcctt ctagtgtagc 1320
cgtagttagg ccaccacttc aagaactctg tagcaccgcc tacatacctc gctctgctaa 1380
tcctgttacc agtggctgct gccagtggcg ataagtcgtg tcttaccggg ttggactcaa 1440
gacgatagtt accggataag gcgcagcggt cgggctgaac ggggggttcg tgcacacagc 1500
ccagcttgga gcgaacgacc tacaccgaac tgagatacct acagcgtgag ctatgagaaa 1560
gcgccacgct tcccgaaggg agaaaggcgg acaggtatcc ggtaagcggc agggtcggaa 1620
caggagagcg cacgagggag cttccagggg gaaacgcctg gtatctttat agtcctgtcg 1680
ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtt ctttcctgcg ttatcccctg attctgtgga taaccgtatt accgcctttg 1860
agtgagctga taccgctcgc cgcagccgaa cgaccgagcg cagcgagtca gtgagcgagg 1920
aagcggaaga gcgcccaata cgcaaaccgc ctctccccgc gcgttggccg attcattaat 1980
gcagctggca cgacaggttt cccgactgga aagcgggcag tgagcgcaac gcaattaatg 2040
tgagttagct cactcattag gcaccccagg ctttacactt tatgcttccg gctcgtatgt 2100
tgtgtggaat tgtgagcgga taacaatttc acacaggaaa cagctatgac catgattacg 2160
ccaagcgcgc aattaaccct cactaaaggg aacaaaagct gggtaccggg ccccccctcg 2220
aggtcgacgg tatcgataag cttgatatcg aattgacgtg aattcttccc atgattcctt 2280
catatttgca tatacgatac aaggctgtta gagagataat tggaattaat ttgactgtaa 2340
acacaaagat attagtacaa aatacgtgac gtagaaagta ataatttctt gggtagtttg 2400
cagttttaaa attatgtttt aaaatggact atcatatgct taccgtaact tgaaagtatt 2460
tcgatttctt ggctttatat atcttgtgga aaggacgtgg atgtgttgtt tgtgtgatac 2520
tataaagttg gtagattgtg actggcttaa aaaatcatta attaataata ggttatgttt 2580
agagtgttcc ccgcgccagc ggggataaac cgcaggccaa tggggaggac atcgatgtca 2640
cctcgtgttc cccgcgccag cggggataaa ccgttttttg aattcctgca gcccggggga 2700
tccactagtt ctagagcggc cgccaccgcg gtggagctcc aattcgccct atagtgagtc 2760
gtattacgcg cgctcactgg ccgtcgtttt acaacgtcgt gactgggaaa accctggcgt 2820
tacccaactt aatcgccttg cagcacatcc ccctttcgcc agctggcgta atagcgaaga 2880
ggcccgcacc gatcgccctt cccaacagtt gcgcagcctg aatggcgaat gggacgcgcc 2940
ctgtagcggc gcattaagcg cggcgggtgt ggtggttacg cgcagcgtga ccgctacact 3000
tgccagcgcc ctagcgcccg ctcctttcgc tttcttccct tcctttctcg ccacgttcgc 3060
cggctttccc cgtcaagctc taaatcgggg gctcccttta gggttccgat ttagtgcttt 3120
acggcacctc gaccccaaaa aacttgatta gggtgatggt tcacgtagtg ggccatcgcc 3180
ctgatagacg gtttttcgcc ctttgacgtt ggagtccacg ttctttaata gtggactctt 3240
gttccaaact ggaacaacac tcaaccctat ctcggtctat tcttttgatt tataagggat 3300
tttgccgatt tcggcctatt ggttaaaaaa tgagctgatt taacaaaaat ttaacgcgaa 3360
ttttaacaaa atattaacgc ttacaattta g 3391

<210> SEQ ID NO 36
<211> LENGTH: 61
<212> TYPE: DNA
<213> ORGANISM: Artificial Sequence
<220> FEATURE:
<223> OTHER INFORMATION: Synthetic sequence, primer1 (Cse1)

<400> SEQUENCE: 36
gcaaagaatt cagatctcca ccatgcctaa gaagaagaga aaagtgaacc tgctgattga 60
c 61

<210> SEQ ID NO 37
<211> LENGTH: 49
<212> TYPE: DNA
<213> ORGANISM: Artificial Sequence

```
<220> FEATURE:
<223> OTHER INFORMATION: Synthetic sequence,   primer2 (Cse1)

<400> SEQUENCE: 37

tcatcgatgc atctcgagtt atccattaga aggtcctccc tgtggcttc                49


<210> SEQ ID NO 38
<211> LENGTH: 61
<212> TYPE: DNA
<213> ORGANISM: Artificial Sequence
<220> FEATURE:
<223> OTHER INFORMATION: Synthetic sequence,   primer1 (Cse2)

<400> SEQUENCE: 38

gcaaagaatt cagatctcca ccatgcccaa gaagaagcgg aaggtggccg atgagatcga     60

c                                                                    61


<210> SEQ ID NO 39
<211> LENGTH: 49
<212> TYPE: DNA
<213> ORGANISM: Artificial Sequence
<220> FEATURE:
<223> OTHER INFORMATION: Synthetic sequence,   primer2 (Cse2)

<400> SEQUENCE: 39

tcatcgatgc atctcgagtt aggcgttctt atttgtggtc agcacgaag                49


<210> SEQ ID NO 40
<211> LENGTH: 61
<212> TYPE: DNA
<213> ORGANISM: Artificial Sequence
<220> FEATURE:
<223> OTHER INFORMATION: Synthetic sequence,   primer1 (Cas5)

<400> SEQUENCE: 40

gcaaagaatt cagatctcca ccatgcccaa gaagaagcgg aaggtgtcca atttcatcaa     60

c                                                                    61


<210> SEQ ID NO 41
<211> LENGTH: 49
<212> TYPE: DNA
<213> ORGANISM: Artificial Sequence
<220> FEATURE:
<223> OTHER INFORMATION: Synthetic sequence,   primer2 (Cas5)

<400> SEQUENCE: 41

tcatcgatgc atctcgagtt atgcctctcc attgttccgc acccagctc                49


<210> SEQ ID NO 42
<211> LENGTH: 61
<212> TYPE: DNA
<213> ORGANISM: Artificial Sequence
<220> FEATURE:
<223> OTHER INFORMATION: Synthetic sequence,   primer1 (Cas6)

<400> SEQUENCE: 42

gcaaagaatt cagatctcca ccatgcccaa gaagaagcgg aaagtgtacc tgagcaaagt     60

g                                                                    61


<210> SEQ ID NO 43
<211> LENGTH: 47
<212> TYPE: DNA
<213> ORGANISM: Artificial Sequence
<220> FEATURE:
```

<223> OTHER INFORMATION: Synthetic sequence, primer2 (Cas6)

<400> SEQUENCE: 43
tcatcgatgc atctcgagtt acagaggtgc cagtgacagc agcccac 47

<210> SEQ ID NO 44
<211> LENGTH: 61
<212> TYPE: DNA
<213> ORGANISM: Artificial Sequence
<220> FEATURE:
<223> OTHER INFORMATION: Synthetic sequence, primer1 (Cas7)

<400> SEQUENCE: 44
gcaaagaatt cagatctcca ccatgcccaa gaagaagcgg aaggtgcgct cctacctgat 60
c 61

<210> SEQ ID NO 45
<211> LENGTH: 49
<212> TYPE: DNA
<213> ORGANISM: Artificial Sequence
<220> FEATURE:
<223> OTHER INFORMATION: Synthetic sequence, primer2 (Cas7)

<400> SEQUENCE: 45
tcatcgatgc atctcgagtt actggctcac gtccattcct cccttgatc 49

<210> SEQ ID NO 46
<211> LENGTH: 6265
<212> TYPE: DNA
<213> ORGANISM: Homo sapiens

<400> SEQUENCE: 46
tcaccaaccg ccaagagagc ttgatatgac tgtatatagt atagtcataa agaacctgaa 60
cttgaccata tacttatgtc atgtggaaaa tttctcatag cttcagatag attatatctg 120
gagtgaagaa tcctgccacc tatgtatctg gcatagtgtg agtcctcata aatgcttact 180
ggtttgaagg gcaacaaaat agtgaacaga gtgaaaatcc ccactaagat cctgggtcca 240
gaaaaagatg ggaaacctgt ttagctcacc cgtgagccca tagttaaaac tctttagaca 300
acaggttgtt tccgtttaca gagaacaata atattgggtg gtgagcatct gtgtgggggt 360
tggggtggga taggggatac ggggagagtg gagaaaaagg ggacacaggg ttaatgtgaa 420
gtccaggatc cccctctaca tttaaagttg gtttaagttg gctttaatta atagcaactc 480
ttaagataat cagaattttc ttaacctttt agccttactg ttgaaaagcc ctgtgatctt 540
gtacaaatca tttgcttctt ggatagtaat ttcttttact aaaatgtggg cttttgacta 600
gatgaatgta aatgttcttc tagctctgat atcctttatt ctttatattt tctaacagat 660
tctgtgtagt gggatgagca gagaacaaaa acaaaataat ccagtgagaa aagcccgtaa 720
ataaaccttc agaccagaga tctattctct agcttatttt aagctcaact taaaaagaag 780
aactgttctc tgattctttt cgccttcaat acacttaatg atttaactcc accctccttc 840
aaaagaaaca gcatttccta cttttatact gtctatatga ttgatttgca cagctcatct 900
ggccagaaga gctgagacat ccgttcccct acaagaaact ctccccggta agtaacctct 960
cagctgcttg gcctgttagt tagcttctga gatgagtaaa agactttaca ggaaacccat 1020
agaagacatt tggcaaacac caagtgctca tacaattatc ttaaaatata atctttaaga 1080
taaggaaagg gtcacagttt ggaatgagtt tcagacggtt ataacatcaa agatacaaaa 1140
catgattgtg agtgaaagac tttaaaggga gcaatagtat tttaataact aacaatcctt 1200

-continued

```
acctctcaaa agaaagattt gcagagagat gagtcttagc tgaaatcttg aaatcttatc   1260
ttctgctaag gagaactaaa ccctctccag tgagatgcct tctgaatatg tgcccacaag   1320
aagttgtgtc taagtctggt tctctttttt ctttttcctc cagacaagag ggaagcctaa   1380
aaatggtcaa aattaatatt aaattacaaa cgccaaataa aattttcctc taatatatca   1440
gtttcatggc acagttagta tataattctt tatggttcaa aattaaaaat gagcttttct   1500
aggggcttct ctcagctgcc tagtctaagg tgcagggagt ttgagactca cagggtttaa   1560
taagagaaaa ttctcagcta gagcagctga acttaaatag actaggcaag acagctggtt   1620
ataagactaa actacccaga atgcatgaca ttcatctgtg gtggcagacg aaacattttt   1680
tattatatta tttcttgggt atgtatgaca actcttaatt gtggcaactc agaaactaca   1740
aacacaaact tcacagaaaa tgtgaggatt ttacaattgg ctgttgtcat ctatgacctt   1800
ccctgggact tgggcacccg gccatttcac tctgactaca tcatgtcacc aaacatctga   1860
tggtcttgcc ttttaattct cttttcgagg actgagaggg agggtagcat ggtagttaag   1920
agtgcaggct tcccgcattc aaaatcggtt gcttactagc tgtgtggctt tgagcaagtt   1980
actcaccctc tctgtgcttc aaggtccttg tctgcaaaat gtgaaaaata tttcctgcct   2040
cataaggttg ccctaaggat taaatgaatg aatgggtatg atgcttagaa cagtgattgg   2100
catccagtat gtgccctcga ggcctcttaa ttattactgg cttgctcata gtgcatgttc   2160
tttgtgggct aactctagcg tcaataaaaa tgttaagact gagttgcagc cgggcatggt   2220
ggctcatgcc tgtaatccca gcattctagg aggctgaggc aggaggatcg cttgagccca   2280
ggagttcgag accagcctgg gcaacatagt gtgatcttgt atctataaaa ataaacaaaa   2340
ttagcttggt gtggtggcgc ctgtagtccc cagccacttg gaggggtgag gtgagaggat   2400
tgcttgagcc cgggatggtc caggctgcag tgagccatga tcgtgccact gcactccagc   2460
ctgggcgaca gagtgagacc ctgtctcaca acaacaacaa caacaacaaa aaggctgagc   2520
tgcaccatgc ttgacccagt ttcttaaaat tgttgtcaaa gcttcattca ctccatggtg   2580
ctatagagca caagatttta tttggtgaga tggtgctttc atgaattccc ccaacagagc   2640
caagctctcc atctagtgga cagggaagct agcagcaaac cttcccttca ctacaaaact   2700
tcattgcttg gccaaaaaga gagttaattc aatgtagaca tctatgtagg caattaaaaa   2760
cctattgatg tataaaacag tttgcattca tggagggcaa ctaaatacat tctaggactt   2820
tataaaagat cactttttat ttatgcacag ggtggaacaa gatggattat caagtgtcaa   2880
gtccaatcta tgacatcaat tattatacat cggagccctg ccaaaaaatc aatgtgaagc   2940
aaatcgcagc ccgcctcctg cctccgctct actcactggt gttcatcttt ggttttgtgg   3000
gcaacatgct ggtcatcctc atcctgataa actgcaaaag gctgaagagc atgactgaca   3060
tctacctgct caacctggcc atctctgacc tgtttttcct tcttactgtc cccttctggg   3120
ctcactatgc tgccgcccag tgggactttg gaaatacaat gtgtcaactc ttgacagggc   3180
tctattttat aggcttcttc tctggaatct tcttcatcat cctcctgaca atcgataggt   3240
acctggctgt cgtccatgct gtgtttgctt taaaagccag gacggtcacc tttggggtgg   3300
tgacaagtgt gatcacttgg gtggtggctg tgtttgcgtc tctcccagga atcatcttta   3360
ccagatctca aaaagaaggt cttcattaca cctgcagctc tcattttcca tacagtcagt   3420
atcaattctg gaagaatttc cagacattaa agatagtcat cttggggctg gtcctgccgc   3480
tgcttgtcat ggtcatctgc tactcgggaa tcctaaaaac tctgcttcgg tgtcgaaatg   3540
```

-continued

```
agaagaagag gcacagggct gtgaggctta tcttcaccat catgattgtt tattttctct   3600
tctgggctcc ctacaacatt gtccttctcc tgaacacctt ccaggaattc tttggcctga   3660
ataattgcag tagctctaac aggttggacc aagctatgca ggtgacagag actcttggga   3720
tgacgcactg ctgcatcaac cccatcatct atgcctttgt cggggagaag ttcagaaact   3780
acctcttagt cttcttccaa aagcacattg ccaaacgctt ctgcaaatgc tgttctattt   3840
tccagcaaga ggctcccgag cgagcaagct cagtttacac ccgatccact ggggagcagg   3900
aaatatctgt gggcttgtga cacggactca agtgggctgg tgacccagtc agagttgtgc   3960
acatggctta gttttcatac acagcctggg ctgggggtgg ggtgggagag gtctttttta   4020
aaaggaagtt actgttatag agggtctaag attcatccat ttatttggca tctgtttaaa   4080
gtagattaga tcttttaagc ccatcaatta tagaaagcca aatcaaaata tgttgatgaa   4140
aaatagcaac ctttttatct ccccttcaca tgcatcaagt tattgacaaa ctctcccttc   4200
actccgaaag ttccttatgt atatttaaaa gaaagcctca gagaattgct gattcttgag   4260
tttagtgatc tgaacagaaa taccaaaatt atttcagaaa tgtacaactt tttacctagt   4320
acaaggcaac atataggttg taaatgtgtt taaaacaggt ctttgtcttg ctatggggag   4380
aaaagacatg aatatgatta gtaaagaaat gacacttttc atgtgtgatt tcccctccaa   4440
ggtatggtta ataagtttca ctgacttaga accaggcgag agacttgtgg cctgggagag   4500
ctggggaagc ttcttaaatg agaaggaatt tgagttggat catctattgc tggcaaagac   4560
agaagcctca ctgcaagcac tgcatgggca agcttggctg tagaaggaga cagagctggt   4620
tgggaagaca tggggaggaa ggacaaggct agatcatgaa gaaccttgac ggcattgctc   4680
cgtctaagtc atgagctgag cagggagatc ctggttggtg ttgcagaagg tttactctgt   4740
ggccaaagga gggtcaggaa ggatgagcat ttagggcaag gagaccacca acagccctca   4800
ggtcagggtg aggatggcct ctgctaagct caaggcgtga ggatgggaag gagggaggta   4860
ttcgtaagga tgggaaggag ggaggtattc gtgcagcata tgaggatgca gagtcagcag   4920
aactggggtg gatttgggtt ggaagtgagg gtcagagagg agtcagagag aatccctagt   4980
cttcaagcag attggagaaa cccttgaaaa gacatcaagc acagaaggag gaggaggagg   5040
tttaggtcaa gaagaagatg gattggtgta aaaggatggg tctggtttgc agagcttgaa   5100
cacagtctca cccagactcc aggctgtctt tcactgaatg cttctgactt catagatttc   5160
cttcccatcc cagctgaaat actgaggggt ctccaggagg agactagatt tatgaataca   5220
cgaggtatga ggtctaggaa catacttcag ctcacacatg agatctaggt gaggattgat   5280
tacctagtag tcatttcatg ggttgttggg aggattctat gaggcaacca caggcagcat   5340
ttagcacata ctacacattc aataagcatc aaactcttag ttactcattc agggatagca   5400
ctgagcaaag cattgagcaa aggggtccca tagaggtgag ggaagcctga aaaactaaga   5460
tgctgcctgc ccagtgcaca caagtgtagg tatcattttc tgcatttaac cgtcaatagg   5520
caaagggggg aagggacata ttcatttgga aataagctgc cttgagcctt aaaacccaca   5580
aaagtacaat ttaccagcct ccgtatttca gactgaatgg gggtgggggg ggcgccttag   5640
gtacttattc cagatgcctt ctccagacaa accagaagca acagaaaaaa tcgtctctcc   5700
ctccctttga aatgaatata ccccttagtg tttgggtata ttcatttcaa agggagagag   5760
agaggttttt ttctgttctg tctcatatga ttgtgcacat acttgagact gttttgaatt   5820
tgggggatgg ctaaaaccat catagtacag gtaaggtgag ggaatagtaa gtggtgagaa   5880
ctactcaggg aatgaaggtg tcagaataat aagaggtgct actgactttc tcagcctctg   5940
```

aatatgaacg gtgagcattg tggctgtcag caggaagcaa cgaagggaaa tgtctttcct 6000
tttgctctta agttgtggag agtgcaacag tagcatagga ccctaccctc tgggccaagt 6060
caaagacatt ctgacatctt agtatttgca tattcttatg tatgtgaaag ttacaaattg 6120
cttgaaagaa aatatgcatc taataaaaaa caccttctaa aataattcat tatattcttg 6180
ctctttcagt caagtgtaca tttagagaat agcacataaa actgccagag cattttataa 6240
gcagctgttt tcttccttag tgtgt 6265

<210> SEQ ID NO 47
<211> LENGTH: 29
<212> TYPE: DNA
<213> ORGANISM: Artificial Sequence
<220> FEATURE:
<223> OTHER INFORMATION: Synthetic sequence, primer1 (CCR5)

<400> SEQUENCE: 47
ccacttggag gggtgaggtg agaggattg 29

<210> SEQ ID NO 48
<211> LENGTH: 25
<212> TYPE: DNA
<213> ORGANISM: Artificial Sequence
<220> FEATURE:
<223> OTHER INFORMATION: Synthetic sequence, primer2 (CCR5)

<400> SEQUENCE: 48
taaagatgat tcctgggaga gacgc 25

<210> SEQ ID NO 49
<211> LENGTH: 25545
<212> TYPE: DNA
<213> ORGANISM: Homo sapiens

<400> SEQUENCE: 49
gcagtctttc tgccacagcc tcccaaagtg ctgagattat aggtgtgagc cattgtacct 60
ggcttggagt aatgtttttg agcaaagcaa atgtacagga catgcacaga gaggcacagg 120
gagcacagag tccctggatg aatgctctgg ctggtggcag tattgtcaca gggcaggcta 180
cccaaaggtg agcagaacac atgaggctag acaggtacaa cttgctcatg aagagcctcg 240
aatgccaagc ttaggagttt gaactttatt ggaacactga cactaatagt taatgtttac 300
tgagtgctta ctatgtgcta agagctatgc atgaatcacc tcattctaat tctcttaact 360
ctccacagca ggtcttatta tttccagatt gctgatgaaa aactgagtca cagagaggta 420
aaaaaaaaaa aacaaaaaca ccctgggtcc agagttgtgt gaaaaaattt taacaggtta 480
gagttgtgtt gtagaaatct ggtagccagc cacgtgtaag acgaattgta gaaaggagag 540
atcacaaatg gctatcataa gagaatcact gggaaaaggt aataagaacc caaattagag 600
gcaaggagaa cagaaagaaa tgaaagaatg caaagactga ctggatgtgc acagcagtga 660
ccgagagaaa ggaggtatca caggtgcctc ttagctgcta agcctgggtg tcctgcagaa 720
aggggcagct attatcagaa gagagaagcc agagagaggc acagatttgg tggggatgat 780
gttgagctcc gtttgggggt atggtgagtg tctagggggc ctgtaggaac ccctccagaa 840
aaattctcac aagcatttga aaatcagtga cttgatctgg agaaaaatat agggctggca 900
ttacaaacct gccggggtct gcattacagt attggttgaa agtgtggaaa ttgataatga 960
tagatggttg gtagatacat agatagatag atagatagat agatagatag atagatagat 1020
agatagatag atagaataaa tagcatgata catggaatga gggaagggct aaggataaag 1080
atgccttcat ggatgcccac agttaggaga agaaagtaga gcccatgaag gaacaactcc 1140
cagagtttgc agatccaggc aagtatcttg ttcagaaaat aaagggaagg gagtttccaa 1200
aagaaaaggg ggttgaaggt actcagatgc tgaggagcct ataaacaatt gtgactaaaa 1260
aagactcaaa tttggaaata aggtgtccta atgaacattt cagaggatgg agagagattc 1320
ttaaagtcag cctttggaag aataactata tagaacactt ccagaggcca aactagtgac 1380
aatggatcaa aagaattaaa atattgcata tctggaaatt acacagctag aaatatgtag 1440
aaaagaaaca caaacatgcg gtaagataca gctatggagc tgtttgtcga aattttgtta 1500
aaacagtgaa aatctgtaaa ctgtattaat gtccaacaat aaaaaatatt taatgagagg 1560
caaagatgct ttgattggtt ataaagataa agaagttaca atactatgta cagtatgatc 1620
ctttttttaa agggaggcac atatagaaag aactggaagg atatactgta agaatttcac 1680
gatgtttgtt tctgggtagt aggatttgac aattataaga tctctgtttt cccttcactc 1740
ccccctttg gattatctgt attttttata actctgtcca atagacatat aatgtgagac 1800
acataatttt aaatgttcta gtggccacat ttaaaaagta gaaagaaata gataaaataa 1860
tcttcttaag atatttcatt ttactcaata tatccattac tatgtgtaat cgatataaaa 1920
atattaatat tttaaatgtt ttagcactaa gcctgtttaa cactaaatgc agtggatatt 1980
cacatttaca gaacatctct gtttgggcca tccacttctc aagcaccaca ttaccgcatt 2040
tggctcctag cacggctcta tgaaataata gcagttaata tttatcaaaa gcctactatg 2100
ttccaggcac tgctccaagt tcatcaggtg gagattataa ctcattaggt ctcaataact 2160
ccatgaggtt gaacttattg tgctctccac aagcacgtgt tgcttgccct tgtcctcata 2220
ccataatgaa atgtttggag cttttgcaaa agccattttc ctaatatgat gggcatccaa 2280
gtctggttgc aaaggcttgg atagagggca agtgagagaa ttggagagag actaaaaatc 2340
attcaagaaa ttttgtggtg aaaaagacaa gtcaaaagac tgagagaaac atgaggacag 2400
aaaactcttt gtaaggcaag gagacataaa gatgaagtca ggctgaatag gaaagaagga 2460
ggtgaaaggt gaaagagaga tggctggggg tgtggctggt ccaaattctc acaagatctc 2520
tgttggagaa acattgcctg gcttgtgctg gtggcgagat gtacatagca gcttcccagc 2580
tagagggagc agggagtcat ggccttgtga gggagacaga tggagacaca cacaaccccc 2640
atcgcaggtg aatgctatga aagaatgggg tggagggctt cccagggaga tgaactgagt 2700
tttaagaacg aagttagcca gcaaagaagc aaaaggaaga ggatatagac ttgaggatta 2760
catcactgga tgactgagcc actgattgga tgtggaggat gagagagtga tgctttgagg 2820
tgattcccaa gttctccgca tggacaaagg cagagacaat aacttgtact gagtgctctt 2880
tggagtctga cattgatcca gtgcaccaca tatgttatct catttactcc tcacagaggt 2940
cccgtataac gcttgcaatt tcacagatac gcaagctgag gcaaaataat tggcccaggg 3000
ctcaccacta ataaatagga gagtctggat ttggggccag gttattccag aaatagagag 3060
agggagggaa aacgttaatg tggggccaga gccagaacag gtaggctagg ctgtatcagc 3120
ctgggaggca tcgggctatt ctccaaaaag tgaggctccg ggttgcagga gatgggacct 3180
ccaggaaact ggtgggaggc tggacagggg caaagtgaaa ggtaagcagc ctgaagatgg 3240
gtgggatgta gtggactcca gcgtgaagag cctccagtct ctggcagagc tcagcagctt 3300
gggtgggagg aaacgaaggg cagggagcag aaggtggtgg ggggaacggg ttttggttaa 3360
gatgggcagc tgtccagtgg tgaagagggg aagtatttgt gtatacgatc agttgtgggg 3420

-continued gatggtggta gagggagcag tatgagagtc tgggaggaac agggcagggg agatggcaca 3480
ggagaagatt ggggtggggg tgggggcact gatactgaat ccagtacaca gaggcaggct 3540
tagagacccc ctgagggtga caaattcttc tcttaacttg ctgcagagga aacgacaaga 3600
gaataggtcc taagaggagt gaaaatagag gaaactggcc aagggataaa gataagcaga 3660
gctatggaag aaaaggaaga aaattaggga attactggag aggaagctga cagaaagggg 3720
cgctgggaga ggaaaaggtg agggaggacg aaaacggaac tcctatcacc cagcgcattc 3780
cagcaccccc tccccctccc ccgggaagtc tgcgactgca tcctcacagg gatggaatgg 3840
gagtggaagc taggccaggc tgggaccccg gggctgtccc agcccaacca agacggtgac 3900
cagactcaag ttactgatcc tccgctgttt cttcatctgt aaagtggagt taatgacaga 3960
cagctggatg tcaacgtttt ttgttgtttg ttttagagat gggatctccc tgtatcgccc 4020
aggctggagt gcagcggtat gatcacggct cactgcagcc tcgacctcct gggctcgaga 4080
gatcttcctg tctcagcctc ccgagtagaa atgtcagcat ttgaatgcct cacaagggaa 4140
ggtggtgtaa taaaaggtct attgatttag atatgaacaa gtatacccag agccacacga 4200
atgaaaggag gtggccagtg tagatgcaag tctaggacgg tcggtagatt ccaagcttct 4260
ctacctgccc agttaaacaa gttcgtggcc cctggccagc ctctcggtgg gggtctgcga 4320
cagaacgggt gggattcatt accaggctag gagcgcaagg ccctcgggcc gggttcagct 4380
tgctgggctc ctgtcttgtc tcagccccca gcacttgctc tgtcaccgca gagcacaggc 4440
ccaggcaacg tttacccaac tgaacccgca tccctgtggg aaccttgttc caacaaaatc 4500
ccgtcgttgt ctccttccat atggaacgaa aatctccttc tgtacctctg cccagctccg 4560
cacccccgcc cccttagaga tacggcctgg tcgggtcctg gtcccccccct cggcggcgct 4620 tccactttc ccagactgag ggtggggaaa aggaggaggg ggaagaaatc agaggaggaa 4680
aagtcgggag gtaggggagc cgggagacag gagagggggga aaataaagag cctgagacac 4740
aaacgagagg aaaagaccat cacagaaagc tggaaatctc cggagaggcc agcgagaacc 4800
cgcgctcccc acggattcca tcattccttc cgaaggcgcc tctgcggtgt ctcagccgtg 4860
ccaggccccg gggttcccag gacgcggagg agtgctgggt gcggccgcct cgcctcccca 4920
cccctggccg cccctcccca cctcgcccaa gggggccgga acggcgtcgg cgcgcggggg 4980
cttttcggag cagtcgagtg gaaaatagac tttaacccgc tttgtggcgg ccggggcgcc 5040
ctgagcgctc tccaaaccac ggctcccggc gctcaggcgg gccgctgcca agacccggcc 5100
tggagtcccc gcagagttgc gcggcgcacg gaccccgtgg ccttggggcg tcaggaggcc 5160
caacccagat ctgcgcgccc aggcagcgct caggccgcta gaatggaccc cggcagcggc 5220
gaggaagcgg aactctctgc ggctccctct ccgcagtgcg ccggcaaggt ccaggtccca 5280
gcctccccac cgccgcccgc gccctcctag gcctcggagc ggcgcctttc tgcggcctcg 5340
aaggtggggt gggaaagttt ggggagtccc ggctctcaca gcctgtcgtg agaactgccc 5400
ccggggaatt cgtccgccgt acggaaaaac tggccggagc agagtcgtcc gcggttccgc 5460
ggtcgcgggt ggaaggtgaa ggtcgaggga ggtcaggctg cttctgcgtg tcctgacggc 5520
tggcgtgttc tcttgagatg ggctcgggct acttggccag cttcaattta agccacagtg 5580
tctccgaggc cctgacctgg tccggcccgc cgacacttga gcccccagag cctcagagaa 5640
ggcgaggggg tggatctccc agtgccgagg cccgccgtcc tggtccaagc cggtcgcggc 5700
accgtgtctg ggcactggag ctgcttccag ccccgcgaac agctggaggg tggcagtggg 5760

-continued

```
accgctccgg cggcttctcc cgcgcagtgc cccgcctggc cccttgtgaa gggagtgagc   5820

gtcccctttc cagagctgtc ccccgtgaca tccagaaaac gcgaaacctc aggaacaagg   5880

tcgcagcttc agaccgcggc ccaggaggcc gatggtgggt gagtgggaga gtcccggaga   5940

gcagggggc agagagctgg ttttcgggaa aaccaatgtg ttggacccca aacatccacc   6000

ctccgctcgg atccaagttc tctgagaact gaaacgacat cccgggacga atgggagagt   6060

taggctgagc tacacaccgg ggaggggagg gttggagttt agccccaagc ccttcggacg   6120

ccttcttcgg ctcccgcgtg ggttgagacg gcggcacggc caccagactc agctaaaggg   6180

cggagtcgcg aggagaagcc agtggcgagg ggaggaggag gcctggatct ccccgcgaag   6240

gctccagtcc ggcttttgcc tccgactgcg ggctccctcc ccacccgccg tccctcgccc   6300

cgccccgccc cgcccccac cttggggcag gtgagcggcg gccaatgggc gagcgcgggg   6360

caggtgcccg ctaactcgcg cctcgcagcg ctgggcggcc ggggctgggc agggcagtgc   6420

ggggacaccg gggctgggg tcggtcccag cgggactccg aaaggaggga gacgagctca   6480

accctcgggc cttactggca gctcgcagcc tagcacggag cccgcgcctg tgcgggcgcc   6540

tggagctgcc cgctccgccg cagcagccgc cgcgcctggc cgtacgctgt ggccggaccc   6600

cgcggtcgct cgctcacaca cccctcgccg ctccgcgcct ggctcgcccg cgggggccga   6660

gcgcgagcgg gcgggcgggg gaggtgaggg gtgcgggcgg gtgtgcatgt gcctggctgg   6720

gtgcacaccc cgcaaggcgg cggcgccagg acgcggagcg ctccccagag cccggctgcc   6780

tcgcacagct cccgcggctg cgaccatgtt ccagcccgcg gccaagcgcg gctttaccat   6840

agagtccttg gtggccaagg acggcggcac cggcgggggc actggcggcg gggcgcggg   6900

ctcccatctc ctggcggcgg ccgcctccga ggaaccgctc cggcccacgg cgctcaacta   6960

ccctcacccc agcgcggccg aggcggcctt cgtgagtggc ttccctgccg cggccgccgc   7020

gggcgcgggc cgctcgctct acggtgggcc cgagctcgtg ttccccgagg ccatgaacca   7080

ccccgcgctg accgtgcatc cggcgcacca gctgggcgcc tccccgctgc agcccccgca   7140

ctccttcttc ggcgcccagc accgggaccc tctccatttc taccccctggg tcctgcggaa   7200

ccgcttcttc ggccaccgct tccagggtga gtgtccacgc tgtgcccgcc gaggcggccg   7260

gccggcgccc gtgctgcggc gatgcggggg aggctcgggg gcgcgcgggg ctgtttagaa   7320

gttactgccg ggaaggctgc aggtccgcgg aggtagattc ccaggcaggg aagagctgtg   7380

cggcatccac ccgcgccttc gccgcgtagg tctccctccc aggaaagcag gtggagacct   7440

ccaggctttt ctagaaaata taccagttcg gacgcaagcc caggcgcgtc ctcggagcct   7500

gtgctggccc tcgccacagc ctgcccaatt ctctctccca gctgagccag tctcagacca   7560

gagtacaact cctcccgctc tccctccgcc cggcttaacc tcgcaccacg cttctctcgc   7620

aagtccacca ccacctccga gacctcagcc ttcgctggcg cgtccgggcg ggggaaagtc   7680

cattcgcgtg ccccagctct gggggaagca agggcagcag ggagggcgaa tcggagagtt   7740

aatgttcagt gtggagggcc tggctgtctt gggatgtttc tcggcaacct tggcccgact   7800

tctccaagtc acacgtgcct ctcctaccca aggtggggaa ggtttgcagt aagcaaactg   7860

gcttccgccg ttgctcgccg ccttcgggag ggagcccacc cggctgctgg aataccgagg   7920

acagttttcc cgggcagggg gcgggggcag agggctttta aggtcgtagc cagtccgaac   7980

cccggagttt gcatccagca atcggcttgc taataaagat cctccactgg ccctacacac   8040

acacacacac acacacacac acacacacac acgtttcaat tatttgtctt tcccggagaa   8100

aagagagttg catttgttgg agttcgtttt cttccttgaa atttgttgga gtttgttttt   8160
```

-continued

```
ttcttttctt ttttttaaa ttttatttta aagagtggcc ttgatttgta caggcatcac   8220
tttagtttcc agttttattt tgttagtgta gaccagacca cagccttgtg agaagggtct   8280
atggctcaga gctaggtaac ccggctttta gagaaacaaa tgaaagggac atggctggag   8340
cttcggctcc aggagctaat gtgacggtct gtagtctagg tctacagtca attagatgtt   8400
tggcacagtt gtttagataa taaaatgaaa attatctctt gacactttga ctttcacaga   8460
aaaccgcttt cccaggtccc gatttgtcag gcaatttttt cagtcccacc tggccaatag   8520
atgctgacct ggcagatacc acaaaaccag agaatgtaat tactagaata agaattgttg   8580
tgggtagcct tgcctcctct ttgaagattt caaagacttg cccaaatcca aatccgaaaa   8640
aacaaaaatg ctacaatgtc atctgccttg ggcaagagtt tctgccactt aaaaataaat   8700
gtttactgat aacatgagga tatctttaaa attgagcaat ctaccctggt cctccgtggg   8760
ctcgatccga agcctgggtc tcgaaacctg gcgcccaggg gccgagttgt agttggggcg   8820
gtgtgtgagc ccgcgggccg ccgcggccga ggggctggcg ggttggaggc ttgtggaggg   8880
ataggggctc ggaggagagg gcggggtcgt tcctaagtcc tgtggcctcc agccgttcag   8940
cttgtccgga gtcggcatcc tgggccgcac cctcggcttc gaatccagcc cctgacgccc   9000
tccgcaccgc ggttcctgcc tccgggcgcc gagggccggg ggcgcctgga gagaaatcca   9060
gctccggctc tgagcgtctc cagtcaggcg aggcggataa atccttcgca aaaccctctt   9120
ggaaattgcc gccgcttcct gagccatcag tcccagcggg tacgttatcg agtagcacaa   9180
acagttggat ttttccctca agaaccgagt ctggacgcgg agatggagcc aagtgtggct   9240
gcattttcgg acccggaaat ccgttgggca ctgaaggact tttcgaaccc tgtagcgctg   9300
ttgcttcgcg gtccatcgtc gccgctgcag acggatgcgc tccccggcgg ctctacgccc   9360
tccagtcccg gccaggcctc tgggctggga gccgagccgt ctcgggccct ccggcgccgc   9420
gttttctaga gaaccgggtc tcagcgatgc tcatttcagc cccgtcttaa tgcaacaaac   9480
gaaaccccac acgaacgaaa aggaacatgt ctgcgctctc tgcgcagcgc ttgggcggcg   9540
cggtcccggc gcgcggggaa gcggcgtctc cgctaaccga ggcgctggaa ggggaaaagc   9600
gaatgcggaa tcgtccagga ctccgaaggt cggggccgct cgcgagcacc gaaggggagg   9660
agccgacgaa gaccaggagt gggccgcatt tcggtactgt ttccccgaga tcaggaactt   9720
tccgggtcta ggagcaacgc ctggaggggg ctgtagagac ccagcccccc gggacccgca   9780
actacaatgg gccggagctt ctaaggtcgc ctttgttctg gcaggaggac ggggaatgag   9840
gttatctccg ccgcctgtcc tgcctctccc tctcctagcc ctagggccct ccgcccagcc   9900
gtccggccct gagcccctgg ccggcggcgg cctctccagc gaagactgcg gctcgaagac   9960
tgcagctcgg accccgggtg cttcggatcc ctagctccca cctccagctc cctcattcct  10020
gggaatctct tgtgctagtt cccagccatt gccttgaagg ggccctaaaa gagtggctgt  10080
agaaaaatcg gaggggtagg gaagcaggga ggagaggggt attcatttcc ctagctccag  10140
ggacggctat accagtccct ttccactttg ctaactgtcc tagtccgaaa ctgacagccc  10200
gttctcacag cccagaatta ctgcgtccaa acaggccgca ccctagaccc aagtttgttc  10260
tgcccttgtg gtccaggcaa gggaaactga acccctggta ggggtggttc aggcctcctt  10320
cccacaggtc ggggggcggg gcggtacagg tacctgtgca cctaaggcat cacccttgtc  10380
tttgcagaaa catgtagcaa ttgatctgtt tctcaggatg tttggtgttg tactaaacat  10440
cctctttcta acagggaaac gtccttattc ttttggaatc aaataacctg tcatcactta  10500
```

-continued

```
gcatcttgac tcatcctgca gtctcctgct tctctgtgat agggttagaa ggacccctgt  10560
atttttgcac atgcatgtga atataccctt taggacacat gctgtctacc acaactggac  10620
atgacaatga cctggggcca ttttctcagt aaggtagacc caaagcaacc tagcatcccc  10680
ctaaaataac cagacttgag gcaaaggggc atgtatgttg gtacagaagc ttgttgcctt  10740
catcctctca tctgggttta taaagacaaa cacagagcac tccaccacac aggtgactga  10800
catataccac ataattacaa aataatcact aagtcagaga cactggggca gactgcagac  10860
ctgcttcctc agccccacac tgcccttcac acctctgcct cctattcata cacacttacg  10920
gggctttcca cactgcagcc tcacttctga ccaacctggg ccagcccagc atctgaggcc  10980
aaaccctgcc aatgctggga tgagctaggc tttctctctc cctctctggt tcatttgtcc  11040
agaggaaacc actgttggga cttcacccag gttcataaca atgttgtttt ttgaagcaag  11100
ttattaacat taacaagaag catttgcttt ccacccacct ttccctggcc tacctcactg  11160
gccccacccc agagacttta atcttcctta ttccccacct ggagcaggct ccatattttt  11220
ctgcccttta ctcatctctg ccagaccacc tcccctgacc atctgtctat tccactatcc  11280
caagtcaaac ttctcttcag tcggacctga gggccctaga tctgcgccac ttgaataatc  11340
aaatggggtg tccctcaccc atctccctgt gatgtggtcc caccattttt gtggctgcac  11400
agatccaacc agttgaaatt gataaggtga ctggagatta ttgactgacc ccttccaggc  11460
actagccccg caatcctagc aactctgttc cacagaaaac tccagcaaaa acttggcttc  11520
tttaggtaac caaagcccag agacttggag gaagtaaggt cagggagttt ccaccaacag  11580
agggacaaga acagttacct ggagagtttt agctacagca tctcaattat ctgcttttga  11640
ttcacttaca tagatgtttc cagagatggg agatgttaac tgaattatcc aggtgattgt  11700
cttagagcaa agcaacaggt caaatcaagt ccaaccagta gccatctctg aagaaattaa  11760
ttggatcagt caatcccaac agctaattct gtcaaaataa tccatctagg gttccgtgtt  11820
tttggtgcat caggaggctg ttatgtgccc ttacatgaga atccatgggt gattttgtca  11880
gggcctgtta tgagtctgtt agcatgtgca accaagccag agattgtgtg agggcctagt  11940
ggggtgttca ttgagacagg cgctgtgggt agaggcttgt tttggcattg atagtttctg  12000
accccatctc ccctacccca gcttcatcca gtccagtgtt atcccttcct cctgcatgtg  12060
ggagctgagt ccctatgctg gccaacattt gctaagggac agtcacactc taaaaatcct  12120
atacagtaga taggaaaaaa gacagtaggg aggctggaac atatatttac acacgcccat  12180
gcagaaacca atatatctat atctatatat attagagaga aagatgacat ctagatattt  12240
atacacatgt ttctttagca agggactatt cagggatgaa gcagggatga agcttttccc  12300
accagacagt acttggagtc tccagtgtgt gtgttgggat agggggttgg gggcttaccc  12360
tagaggctgg gtctctggac cgccaaggcc tgggggagag agaggtggag aaaggggaag  12420
aaggagcctg actttccact tccaggtgct gcctggacca ctgacctagc cactggccta  12480
tttatacccc ctgcaagaca gagctagagc gtgctggcag gagtttttaa tgagttagta  12540
gcctgagcat tcagccgcaa gactagtgca agcaggtgtg aagggattgc tccttgtgta  12600
ccttctagtt cttgaatctg tgtttggcaa aggtgtgcct agcaccccgc tgctcccctt  12660
atcacgttcc tgacccccag ccctgcctct accctgggtc ctcttggagg gagatgcttt  12720
gcgaccagtt aactgaaagc aaatcgttgg ggctggcggc cagggcagcg cccctgggaa  12780
agggcggaga aagagcgcca tggacttttc ttccccaccc cttggcctct tccgctgccc  12840
caggcattgt gaatgtgggt ccacgcctcg tccggcctgc cccatctctt ggcttaacag  12900
```

agggatctgg agagctgtta ttccccgcgt tcccccgcgg agtggctctc gagtgcgggg 12960
aggtgttgcg gaggggagtg gacttaggga aggggcggca aaagggcaaa gggagaaatg 13020
gcgtgtgtgt gcgtgtcaag gaatggagag ggcagggcgc ttgggagcag ggcgcgaggc 13080
caggctctgt tgggccccgg ctcacggcgc cccttctctc tgtctgtacc tgcgtgtgtt 13140
gccgtcggcg gcggggccgc agccagcgac gtgccccagg acgggctgct tctgcacggc 13200
cccttcgcac gcaagcccaa gcggatccgc acggccttct cgccctcgca gctgctgcgg 13260
ctggagcgcg ccttcgagaa gaaccactac gtggtgggcg ccgagcggaa gcagctggcc 13320
ggcagtctca gcctctccga gacgcaggta atcacccccg gtcgcggcct gccctgcgcc 13380
cggagcccgg gtggaggtga gggtgcgcgg gtgcaggaga ggccctgagc ccgccccagc 13440
ccagccctgc tgggttccaa aaggccccca ttccccgcgg cgctgcggtc aagcccgtct 13500
ttagagcctc ttcctcgaga ctgcgtgcag cctgctgagc ccgcaggact tttgtcaagc 13560
gctaaagacc tagcaggagg cagagtaaat gcaaactgta tcccgagccc ggctcccaaa 13620
gctcctcacg gggggaccag gttccctgga ggaagcgggt cgcctcggga gcgggcagcg 13680
caggcagcac cgaggccact ggagctggct ccagccctgg cattcctgca gcccttttcc 13740
cgccactgtg tcggggcgct catagtcctg cggggagccg gtccgcactg gctttgctgc 13800
tgttcctggg caaaactggc ggggccttgg ctgcccacca gccaggagcg tctggggaga 13860
aagcccaggt gtcctcagac taccaacaga ggggcttaac cagggagggg ccagcccctg 13920
cttggggccc gagggttgct ctgatccggc ccaggccggc tgatagggct gtggaagcca 13980
cggtgtgcgc gcgcagagca tctgagtggc ctgggcctgg tgggaaatag accccgggta 14040
ctcaggtgct tctctgaatc actggaaagg ctgtcgaatg ggagaaggaa taaactccaa 14100
cggcgcctgg gcttgaactg agtgaaatta acaattaccg tgtagtgttt ttgtaactga 14160
tcgttaattt aagggaaaaa attaaagaat tagatgaaag ttatagggag gtggatttgg 14220
gttcattgta agtagacttt gccataaata aatgctgcct gggatcactg cataagctct 14280
tggtccaccc aggtccgacg tgttggagtg gggctcagcg accctcagcc tagctgctgc 14340
cctggaggtg gatttcagtc tctgcgtgcc ggccggctcc cagagttgcg agaggccggc 14400
tccgcggtct cccagctacc tcccggctga cttttcacct tccgctcccc tttcctccta 14460
gtctcgaccc tactacacca ccgtcccctc ccaagtcccg ggcagtgaga agatgcccgg 14520
catggggggc agccggagcc tccctttagc agccagagta ggaagggggc ttagtgaggg 14580
agcccagacc caaacttcat ccgcagcttt cttcggcgga ccttaccctc tcctccttca 14640
gtggcatttt ggcatctatt gtcgtcatat ctgtctgctg ccccacttaa tctacaaatc 14700
gctcacgggt cggaggcagg acccgtgcgt tttcagatgt actagctggg ctgttctaac 14760
tgcagggaaa aagcttacaa aacaagagtt aattttaaaa acgtttcaaa gaaagatgtg 14820
tttttaaaaa taagttaata aaataacact cccttttccc tcctggcagt gttttaaaat 14880
tattgtttga aacaaggtgt cagtttaaga atggtgttta taattaactt catttaaaca 14940
gtaatattta ttaaatttta attgcagaac tgtaagaaaa caaaaatggt ttttaatcct 15000
accacccaca gattaacact tgttgaaata atgtcattgt ttttaaactt tcaatttttt 15060
agctcagtga gagcattttt aattaactct ctttcaaact gaacctagct gcctgtcaat 15120
atttgctcct aacaatgcca gttagtaaac ggactgattg tttctttcat ttttattatg 15180
agacatttca aacatatatt taaaacaaaa ccagatagaa taacataaac gtatcctgct 15240

-continued tcattaacta tcaaaactca gggctaatct tcttcccgtc tgtaaatgag ctgctttttg 15300
catatggtac aacaaaaaga atgaggggag gtttgagcct ggggaacctg ccgtggcagc 15360
ctgtccttcc aggtgaagac cctgagatgg agagatggtt tggacagagc ttcccaggtg 15420
ggcaaacacg attttaaata cctgcctccc tgctaactta ctgtgtaacc ctgggcaagt 15480
cacttaacct ctctgagctc tggtttcctc attgagaaaa tagttgttta atgattaaag 15540
gtacctcata tgagctcaaa taatattaat ccccatccct agtcccttcc ctttaaggta 15600
gtatgtcaga ttagtagcat aagaagatcc aaacctgtgt gtcctcttag tccagcgttc 15660
ttcctccctt atgcagtttc cgtcatcaac attgcctttc tgttgccctc ataacttatc 15720
atacggagcc aggctatata attagctact tctctatccg cctcttggta cttaccaggc 15780
aagcttacct gtcatttcca gctatcagct atttgtcaag catcagtcac ccccaacagc 15840
ccccctgcca tgcatttcta ctgttaatat ctgtatctgt ctccagagct ctctaatctg 15900
tcccaccccg tagctgtttt acatctagcc atatacttct gtctgctctc attaaactgc 15960
ctccccaaaa ctggctaatt tatatttccg attttctatt agttatatgt tcttcctaac 16020
aataagaact atttacccat ttgttcatta tctttgtcat ctattttacc ttctgtgttt 16080
ccaccattca tctcaaactt catctccata gagctatttc gcaactgaca aacagtatat 16140
tcatatgtct ggtaatggtt atctattatt ggctctggct ttgtcttctc tctgggtctg 16200
ggcctcagtt tctgtatctg tgagattgaa tgacacaaat tccagggttt tttctagtgc 16260
tgagtttctg tgactcctct acattctact tctctgtgtt tctgtatact acctcctcca 16320
cattctcaga gctcaccaca caacccctgc ctatcatgat atgcatcaaa ctttgttgtt 16380
attacttaat tatctgccat gtccaaacat caatctgtag accagcagta tgcgtctctc 16440
agggagatct taaaatacag attcctgggt ttcacccagg agattctctt aggaagtcca 16500
ggatagggtg caggaaaaag tttaaaaaca gttatttggg tgatcatgat taataacagg 16560
cctgagcatc ttagctctgg gaggcagagg ccaagcctgt ctgtttctta caggacccag 16620
ctcagtgccc gggatggagt acatgctcaa taaacatgta ttgaattaat gagcacattt 16680
ctctttgccc atacaaatac acactaactt tatcagtcat tccccttgct ctctgctgtc 16740
attgctccct ccctgtccct ctccttctat ctttcccttg tactttcaca gctgattgtt 16800
gatttagatt atgcatatac cagtttgtgg ataaaacttc tcggagggtt actcagatca 16860
gtgtgtgaat gagctcttaa tccagatctc agaagtctgt gcactcccca agctttagcc 16920
gggtgctagg aggtgggcaa cctgggtgac tctgtgtgtt tagtgggagt ggggtattcg 16980
tgctgggatg gccagtgcct caatctagga gatgagggaa gagccctggg caagggctag 17040
ttctcccttc aggttctaat gacttgttcc tcactgcttg ggtgccgccc tggagtatga 17100
ccaggaaggt accagtctaa gcttcagtcc tggtggctgg ttgggcagac ctgggcctgg 17160
gtcattgcag aggctcaagt ttaatgagta tgtgtaatgg gtgtgtgcaa catgtgtctg 17220
cccatgtggg gcaccaacgg gctttatgtg attgatgccc aaaggtcaga tgatagcata 17280
ggtacacatt agatgccatt aggcagtcat atgacatgga gtgcagcttg catgcttttg 17340
tgtgtgttcg tgtgtgtgtc gggggcaggg gtaagttagt tttaggggga gtgagagaaa 17400
gcacctggtt gctccaggct gatcaactgg tcagtgtttc cagctactcc ttctgctctg 17460
aacagatcag caggtgtttc ttgaccttgc ctgggttaga gtttagctga gcggtgaagg 17520
caaagggtac agaaacgtgg cctgtggctt tgaagatttc ttactgagtg atgaaggcta 17580
agtgcaaagc ttgcacattt gtgaaacatg cacaggaaga atgactaggg tccccctttga 17640

-continued

```
ggtcacagct gtgggctgag gggtgtcagg atagaaacgc ttgagaagat ggctccagga  17700
ggcctcagac ctggaagact tggggggatg cctaggatcc taggttggag ggaaagaagg  17760
gcagggtttg aggcaggcag atgaagatag agccaccatc ttggagccca agggcaggga  17820
gatcttggga ggcaggagtt acggtcacct gcctatggct ttttcccctc agaggcatgg  17880
aaaggaggat ttggagggtc ctttcctgct ctggaatgtt ctggccttag agggatggat  17940
aagaggggga tatccaagtg acctgaattt tagggaaaaa tcaagagaca tttgttccta  18000
gctcacggtg tgtccacatc tcttctctaa gtcttggctt ttcttcaaga acttctgcat  18060
ctcatgttcc aggagtcctg tgtgggagga tgagggggag ataaaggaga ttagagtggt  18120
tctgtgagga gctgggacca acatgtcctg aggtgaatct tatgatgtct ccctgagaga  18180
gacagaggaa gggtccaggc tgggctgaaa gaggaggaga cagggaggct tagggagatc  18240
atggttatgg ttggtgggga gctggaggtg acctcagctt actgaggtga aggttgaact  18300
tagcatggca ttgattgggc ttgaccttga gagtgggaac agcccacatg atcaaatgat  18360
aggaaatggg tccccaggga agagagaaag ctgaggggtg acttgactga tatctccagg  18420
ctcctgtcca ttctgggata tttgaaatct ttgaagacag gacacgtatt cacctgaaag  18480
tgtgcagggg cctggagcca cagacttttc catttgcagg agtggtgaaa aagaagggat  18540
ccagacctcg ttcattcaga atagcagatt attccaaagt aaagtctgat tagttctgaa  18600
atatcggctg gagccatagt ttgcttgttt gttagttcat ttttcccttt gttcttgcat  18660
gcatgtcttc atttattaat gcatacattg atcagtcctc tagcaaactg atacattcat  18720
tcatccatag cagtttcacc ttcttcattc tgcctgactc aagccaaccc ttcttctgcc  18780
cagcagtagg tgtccctcct ccaacttccc ctaaaagtgg ccaatccaat ttaccatgtg  18840
gaatattaaa aactggccct cttgcaaaag tgtccacaaa actaagaaaa agatccagtt  18900
tctccatcat tgagcacttc tcaaagcctt tgctgattag aattctaccc ctcttctgtt  18960
cattttctcc tgttttccag gtctggccca ggtacctctt gcctagagca taggcttgtc  19020
cagccagatg actatacatg gaacatgtcc tctgggcagg gcactgggac taacataaca  19080
gtttggctct ccagtctcat agtctggtga ggaggcagac gtaaataaat aaattagtgc  19140
acagtggggg tcactgttac tgagactggg aagaggtact aaggaactac aggcaggtga  19200
tggggcagga ccattaagga acatcaggac agggtcttga aggctaagga gagtattcca  19260
gggttggtaa gtcaggagaa tggagacttt tggaaggatg tggcctctga gaaactgaga  19320
tgttcacttc acagtgaaat gaggacttgg gagaccacaa gggacctctt gctacagcag  19380
agaggtcaga gtgggcaagg ggtcctccag ctaacattcc aactgtacct cggggcttag  19440
agagaggtga gtagtgtgtt tgtgttgggg atggggaggc atgtgcagga cagatccagc  19500
ctccaagcca taccatatga cccagctcct ttccagggcc tgttttctct agggaagggg  19560
ctctgaagga tccagagttg cctggctggg ttggagaggt catgaaatgt cactctcatc  19620
tcctaataca ctcagagccc agttcctttt ctttttccaa gtaaaaaata actaccatta  19680
tcaataatct attaaggaaa attcagaaaa gtagaaagaa gaaagaaaca tcacccacac  19740
tttaggtata tttccttcta gtcttttttc cccgtgtgta gattttgttt ttctatggtt  19800
gtgatcacac tgtgccagcc ttgtgcatcc tggcgtttcc attaatgcta tgaagtcata  19860
agcactaccc tgttattgca gtctttgtaa acagcatctg gacactcagc ccaaggctgt  19920
tctccggaag atggccaggc tgcacaggga gagggtttat gtccctgcct ctagagagat  19980
```

-continued gcctacttga ccccagtatt tttcatggag aaaatattca gaatcacctt tcacttgggt 20040
gccctaggaa gctgcctctg gcctatcctg tgcctgaagt cgccatccaa agctttcctt 20100
ctttgagcca gtgttgctag tcaagggcag catgctgggc ccgtcccact acaggccaat 20160
gtgaccgtca gtctccttcc tgaaggacac ttggaaatgc atgtggaaag aggaaggtac 20220
agaaaagggc ccccggtccc tggtactgcc cgcatcacct gacagtcacc ttcggccagc 20280
ccacttgggc ttctcaggaa tgacaccccg gccctgcatc tggccctgag tcacgcacag 20340
gaggcagggt gagctcaccc gcccactgac tggcacagtc atagcaggct ccagggtggg 20400
gggcaggggc caggctgctg ccaaatggtt gtgctgagaa ccacccaggg tccaggtggc 20460
cctgcgccca aagataggtg ggcttggagt ccagcagcct gtgcccagag cctctgccat 20520
cctccacggc cggcctaggt gagatgtgca ggctatgggc ttggaaatga ggggagaatc 20580
cccttgccct cactccatcc atcgaggccg ggcaccaacc cttcctgggc cagctttcca 20640
gcccctggct ggctgctctg caggcactga atgccagctg cccccatccc catgccagtg 20700
ctctaaaatc agtgctctca aacaagggca gatggcgcag tggaagttct ggcaagaggg 20760
gactgtgagg ggaagtcctg gggtaggtgg gacagagagg actgcctggg aagggtgtag 20820
gggcagcacc tcctgggcat gaaaccatct gcagggcaca ggggccaggc ctgcctctgc 20880
atgcactgct tggccttgtg gctaaggcct gtgctttacc cagttctctg ggagcaggag 20940
cagtctttct gaggcctgcc ctcagccctg cccagggttc aaggatctct cctcagcatc 21000
attgctgctg ccaaaaccaa gaggctaccc accattcctc acccgcaact ctgccacgca 21060
gcaccgtctg cacagctgca gttggccaca tccacttgct tttaaatgtg ctgtcatttc 21120
ctggaaacca tccaggcctt gtagcctgcc ctctgcacct cctccccaag gggggcctct 21180
ggagcaagaa tccaagaggt gccctggcag ctgcaagtgt ccccagaaca tttcctctat 21240
gcatgaagga ctgaagccca gagggggaag ggacttagct gagaatcagt acccaggatc 21300
ctcctgccaa cgctgaagat ggtttgggtc tggcctgact ctgcaaagcc aagtaaagaa 21360
ccacggagtc agggagagtt gacagatgaa ggctttctcc acagcccaca agcactaagt 21420
ccagtccagg agccaggatg agcctcccag attatgcatg agaggacatt aagggctgtg 21480
tcctggacac tgaacagatg ctggaggagg agggaaaaga ggcttcctgg aggagatggc 21540
ttagaaccat agacctgccc tctgcctcat gcctcctcca tcatggagga tggttgtcca 21600
gtttctgttt gaaccccacc ccataccttg ccagggctct cactgccaga cacagaatag 21660
ggggctccct gggttcaaag tagagctcac ttctgtcccc tgggcttctc ctgactgttc 21720
cttgtgtgac ctgttcccac atctggatgg gctgcaggag ccagtgctgt ggggacagaa 21780
ggtctggagc tgcccgtgaa gggcagaatg ctgccctcag acccgcttcc tccctgtcct 21840
tgtctgtcca aggagaatga ggtctcactg gtggatttcg gactaccctg aggagctggc 21900
acctgaggga caaggccccc cacctgccca gctccagcct ctgatgaggg gtgggagaga 21960
gctacatgag gttgctaaga aagcctcccc tgaaggagac cacacagtgt gtgaggttgg 22020
agtctctagc agcgggttct gtgcccccag ggatagtctg gctgtccagg cactgctctt 22080
gatataaaca ccacctccta gttatgaaac catgcccatt ctgcctctct gtatggaaaa 22140
gagcatgggg ctggcccgtg gggtggtgtc cactttaggc cctgtgggag atcatgggaa 22200
cccacgcagt gggtcatagg ctctctcatt tactactcac atccactctg tgaagaagcg 22260
attatgatct ctcctctaga aactcgtaga gtcccatgtc tgccggcttc cagagcctgc 22320
actcctccac cttggcttgg ctttgctggg gctagaggag ctaggatgca cagcagctct 22380
gtgacccttt gtttgagagg aacaggaaaa ccacccttct ctctggccca ctgtgtcctc 22440
ttcctgccct gccatcccct tctgtgaatg ttagacccat gggagcagct ggtcagaggg 22500
gaccccggcc tggggcccct aaccctatgt agcctcagtc ttcccatcag gctctcagct 22560
cagcctgagt gttgaggccc cagtggctgc tctgggggcc tcctgagttt ctcatctgtg 22620
cccctccctc cctggcccag gtgaaggtgt ggttccagaa ccggaggaca aagtacaaac 22680
ggcagaagct ggaggaggaa gggcctgagt ccgagcagaa gaagaagggc tcccatcaca 22740
tcaaccggtg gcgcattgcc acgaagcagg ccaatgggga ggacatcgat gtcacctcca 22800
atgactaggg tgggcaacca caaacccacg agggcagagt gctgcttgct gctggccagg 22860
cccctgcgtg ggcccaagct ggactctggc cactccctgg ccaggctttg gggaggcctg 22920
gagtcatggc cccacagggc ttgaagcccg gggccgccat tgacagaggg acaagcaatg 22980
ggctggctga ggcctgggac cacttggcct tctcctcgga gagcctgcct gcctgggcgg 23040
gcccgcccgc caccgcagcc tcccagctgc tctccgtgtc tccaatctcc cttttgtttt 23100
gatgcatttc tgttttaatt tattttccag gcaccactgt agtttagtga tccccagtgt 23160
cccccttccc tatgggaata ataaaagtct ctctcttaat gacacgggca tccagctcca 23220
gccccagagc ctggggtggt agattccggc tctgagggcc agtgggggct ggtagagcaa 23280
acgcgttcag ggcctgggag cctggggtgg ggtactggtg gagggggtca agggtaattc 23340
attaactcct ctcttttgtt gggggaccct ggtctctacc tccagctcca cagcaggaga 23400
aacaggctag acatagggaa gggccatcct gtatcttgag ggaggacagg cccaggtctt 23460
tcttaacgta ttgagaggtg ggaatcaggc ccaggtagtt caatgggaga gggagagtgc 23520
ttccctctgc ctagagactc tggtggcttc tccagttgag gagaaaccag aggaaagggg 23580
aggattgggg tctgggggag ggaacaccat tcacaaaggc tgacggttcc agtccgaagt 23640
cgtgggccca ccaggatgct cacctgtcct tggagaaccg ctgggcaggt tgagactgca 23700
gagacagggc ttaaggctga gcctgcaacc agtccccagt gactcagggc ctcctcagcc 23760
caagaaagag caacgtgcca gggcccgctg agctcttgtg ttcacctgcc cttctgtttg 23820
tcccacttgt caggatgaag gtttcctgac aagcaaatct gcattcctaa gtctttccct 23880
tacgacatcc agacccctct ctttcttctt cacctcccat gtgctcatga aacctctgct 23940
ctttggcctc catgccacca ttctgccggt gctaatgaca gtcaccaacc acagtcactg 24000
gccaccccct tgtggccaaa ctcaaccact tcctgttggg ttcacctgct ccctgatctg 24060
ttggctatgc cctcctggat tctcccaccc cgctctgcct tcatttcggt agctctgact 24120
cctccttcag cctgagttca ttcagtgtga tccatgcctt gtcacctctg gccaccccca 24180
ggtcagtcct tgctctccct gactcctcat tatgtccttt gccttgtggg gatcacatcc 24240
acttccagga cttctctttg gctccctggc ctgtgtcttt agctgacctc tgctgagctg 24300
cagacccgtc aagccagctg cctgctccac cccctgcccc tcagcacctc aaagcccata 24360
catccacagc cggacgcacc tacccatctg tgcttctcca ggatcaccca cctcgacaaa 24420
cagcattaga catgtacaca gtttcccaag ctacaggaaa tctgggaatc ttcctcaagc 24480
ttcctctcct cttccccagc cccatccatt cccatctagt gggttgagtc tagactggct 24540
tcccaaccac acctccctaa tgcagcaccc cctacccccc tgcccagctc cctctgccac 24600
cggcctggcc tgggccctgc tcctctaggg aggtttctgt gaatgtcaag gatgaggtcc 24660
acttcaaagg aggccctcca tgttgcagct aggtttctct tccttgcacc caaacagggc 24720

```
agactcaccc ccttctgagc cccttttgccc catcttcttg ccttgctccc ggtacccttt   24780

gcttcagcat ccccatccct gtccctgagt gagccacagg ttttccctgt gctgtgcctt   24840

cgctcatgct gttcttccca cctggaatgt cgggtgcttg atcaatgtgg aactcactgg   24900

aaagatgtca gagacccagc cttgctgtct gggccacatg cagggatcca agcacacaag   24960

gtccttctgc tgggagcaca gacccaggtc ccactcgcac tctcagcgtc tctctcccac   25020

ctctgcccac ctcacttgtg tccagtcagt gctagaaacc aaagggcttt gtcccatccc   25080

aacacccct ctccctccat cagtcaggaa tgcattctgc acatcttgaa agtcctaaca    25140

tggataagtc cagattaacc cacatggcga ccctcactgc caagcaggtg ggatcacttc   25200

tgggagcaca catgcccagg tgtggaagga aggtgggagg aagagtcatc cttttggccc   25260

cagtggggga cagagaaagg ggtgagctgt tcctctcaag atcctgcctc acttggtagg   25320

gggagggggt ccaggaagat cacagcagag caccccctgt catccgaata aagggctgga   25380

agggacccaa ggaaacctgc cagtctcccg aggccaggcc tgcggggggc ggggcgggga   25440

gtccctgccg cactcccatc caccccccat gttgtgcctc tccctgcaga cggtaaatat   25500

tggtgttgtg acttcattaa taaaggcttc tgtgagcctg aaaaa               25545
```

```
<210> SEQ ID NO 50
<211> LENGTH: 30
<212> TYPE: DNA
<213> ORGANISM: Artificial Sequence
<220> FEATURE:
<223> OTHER INFORMATION: Synthetic sequence,   primer1 (EMX1)

<400> SEQUENCE: 50

gggcttctcc tgactgttcc ttgtgtgacc                                    30

<210> SEQ ID NO 51
<211> LENGTH: 30
<212> TYPE: DNA
<213> ORGANISM: Artificial Sequence
<220> FEATURE:
<223> OTHER INFORMATION: Synthetic sequence,   primer2 (EMX1)

<400> SEQUENCE: 51

caggatggcc cttccctatg tctagcctgt                                    30

<210> SEQ ID NO 52
<211> LENGTH: 7
<212> TYPE: PRT
<213> ORGANISM: Artificial Sequence
<220> FEATURE:
<223> OTHER INFORMATION: Synthetic sequence,   NLS (protein)

<400> SEQUENCE: 52

Pro Lys Lys Lys Arg Lys Val
1               5

<210> SEQ ID NO 53
<211> LENGTH: 21
<212> TYPE: DNA
<213> ORGANISM: Artificial Sequence
<220> FEATURE:
<223> OTHER INFORMATION: Synthetic sequence,   NLS (nucleotide)

<400> SEQUENCE: 53

cccaagaaga agcggaaggt g                                             21

<210> SEQ ID NO 54
```

<211> LENGTH: 19
<212> TYPE: PRT
<213> ORGANISM: Artificial Sequence
<220> FEATURE:
<223> OTHER INFORMATION: Synthetic sequence, BPNLS (protein)

<400> SEQUENCE: 54

Lys Arg Thr Ala Asp Gly Ser Glu Phe Glu Ser Pro Lys Lys Lys Arg
1 5 10 15

Lys Val Glu

<210> SEQ ID NO 55
<211> LENGTH: 57
<212> TYPE: DNA
<213> ORGANISM: Artificial Sequence
<220> FEATURE:
<223> OTHER INFORMATION: Synthetic sequence, BPNLS (nucleotide)

<400> SEQUENCE: 55
aagcggactg ctgatggcag tgaatttgag tccccaaaga agaagagaaa ggtggaa 57

<210> SEQ ID NO 56
<211> LENGTH: 44
<212> TYPE: DNA
<213> ORGANISM: Artificial Sequence
<220> FEATURE:
<223> OTHER INFORMATION: Synthetic sequence, BPNLS insert upper

<400> SEQUENCE: 56
agatcttaat acgactcact atagggagag ccgccaccat ggcc 44

<210> SEQ ID NO 57
<211> LENGTH: 13
<212> TYPE: DNA
<213> ORGANISM: Artificial Sequence
<220> FEATURE:
<223> OTHER INFORMATION: Synthetic sequence, BPNLS insert lower

<400> SEQUENCE: 57
taatatcctc gag 13

<210> SEQ ID NO 58
<211> LENGTH: 22
<212> TYPE: PRT
<213> ORGANISM: Artificial Sequence
<220> FEATURE:
<223> OTHER INFORMATION: Synthetic sequence, 2A (protein)

<400> SEQUENCE: 58

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 59
<211> LENGTH: 66
<212> TYPE: DNA
<213> ORGANISM: Artificial Sequence
<220> FEATURE:
<223> OTHER INFORMATION: Synthetic sequence, 2A (nucleotide Cse1-Cse2)

<400> SEQUENCE: 59
ggaagcggag caaccaactt cagcctgctg aagcaggccg gcgatgtgga ggagaatcca 60
ggcccc 66

<210> SEQ ID NO 60
<211> LENGTH: 66
<212> TYPE: DNA
<213> ORGANISM: Artificial Sequence
<220> FEATURE:
<223> OTHER INFORMATION: Synthetic sequence, 2A(nucleotide Cse2-Cas7)

<400> SEQUENCE: 60
ggctccggcg ccaccaattt ttctctgctg aagcaggcag gcgatgtgga ggagaaccca 60
ggacct 66

<210> SEQ ID NO 61
<211> LENGTH: 66
<212> TYPE: DNA
<213> ORGANISM: Artificial Sequence
<220> FEATURE:
<223> OTHER INFORMATION: Synthetic sequence, 2A(nucleotide Cas7-Cas5)

<400> SEQUENCE: 61
ggatctggag ccaccaattt cagcctgctg aagcaagcag gcgacgtgga agaaaaccca 60
ggacca 66

<210> SEQ ID NO 62
<211> LENGTH: 66
<212> TYPE: DNA
<213> ORGANISM: Artificial Sequence
<220> FEATURE:
<223> OTHER INFORMATION: Synthetic sequence, 2A(nucleotide Cas5-Cas6)

<400> SEQUENCE: 62
ggatctgggg ctactaattt ttctctgctg aagcaagccg gcgacgtgga agagaatcca 60
ggaccg 66

<210> SEQ ID NO 63
<211> LENGTH: 1388
<212> TYPE: DNA
<213> ORGANISM: Homo sapiens

<400> SEQUENCE: 63
tgaatgggta tgatgcttag aacagtgatt ggcatccagt atgtgccctc gaggcctctt 60
aattattact ggcttgctca tagtgcatgt tctttgtggg ctaactctag cgtcaataaa 120
aatgttaaga ctgagttgca gccgggcatg gtggctcatg cctgtaatcc cagcattcta 180
ggaggctgag gcaggaggat cgcttgagcc caggagttcg agaccagcct gggcaacata 240
gtgtgatctt gtatctataa aaataaacaa aattagcttg gtgtggtggc gcctgtagtc 300
cccagccact tggagggggtg aggtgagagg attgcttgag cccgggatgg tccaggctgc 360
agtgagccat gatcgtgcca ctgcactcca gcctgggcga cagagtgaga ccctgtctca 420
caacaacaac aacaacaaca aaaaggctga gctgcaccat gcttgaccca gtttcttaaa 480
attgttgtca aagcttcatt cactccatgg tgctatagag cacaagattt tatttggtga 540
gatggtgctt tcatgaattc ccccaacaga gccaagctct ccatctagtg gacagggaag 600
ctagcagcaa accttccctt cactacaaaa cttcattgct tggccaaaaa gagagttaat 660
tcaatgtaga catctatgta ggcaattaaa aacctattga tgtataaaac agtttgcatt 720
catggagggc aactaaatac attctaggac tttataaaag atcacttttt atttatgcac 780
agggtggaac aagatggatt atcaagtgtc aagtccaatc tatgacatca attattatac 840
atcggagccc tgccaaaaaa tcaatgtgaa gcaaatcgca gcccgcctcc tgcctccgct 900
ctactcactg gtgttcatct ttggttttgt gggcaacatg ctggtcatcc tcatcctgat 960
aaactgcaaa aggctgaaga gcatgactga catctacctg ctcaacctgg ccatctctga 1020
cctgtttttc cttcttactg tccccttctg ggctcactat gctgccgccc agtgggactt 1080
tggaaataca atgtgtcaac tcttgacagg gctctatttt ataggcttct tctctggaat 1140
cttcttcatc atcctcctga caatcgatag gtacctggct gtcgtccatg ctgtgtttgc 1200
tttaaaagcc aggacggtca cctttggggt ggtgacaagt gtgatcactt gggtggtggc 1260
tgtgtttgcg tctctcccag gaatcatctt taccagatct caaaaagaag gtcttcatta 1320
cacctgcagc tctcattttc catacagtca gtatcaattc tggaagaatt tccagacatt 1380
aaagatag 1388

<210> SEQ ID NO 64
<211> LENGTH: 987
<212> TYPE: DNA
<213> ORGANISM: Artificial Sequence
<220> FEATURE:
<223> OTHER INFORMATION: Synthetic sequence, CCR5 Gene with CRISPR induced deletion.
<220> FEATURE:
<221> NAME/KEY: Deleted Nucleotides
<222> LOCATION: (76)..(476)

<400> SEQUENCE: 64
ccacttggag gggtgaggtg agaggattgc ttgagcccgg gatggtccag gctgcagtga 60
gccatgatcg tgccactgca ctccagcctg ggcgacagag tgagaccctg tctcacaaca 120
acaacaacaa caacaaaaag gctgagctgc accatgcttg acccagtttc ttaaaattgt 180
tgtcaaagct tcattcactc catggtgcta tagagcacaa gattttattt ggtgagatgg 240
tgctttcatg aattccccca acagagccaa gctctccatc tagtggacag ggaagctagc 300
agcaaacctt cccttcacta caaaacttca ttgcttggcc aaaaagagag ttaattcaat 360
gtagacatct atgtaggcaa ttaaaaacct attgatgtat aaaacagttt gcattcatgg 420
agggcaacta aatacattct aggactttat aaaagatcac tttttattta tgcacagggt 480
ggaacaagat ggattatcaa gtgtcaagtc caatctatga catcaattat tatacatcgg 540
agccctgcca aaaaatcaat gtgaagcaaa tcgcagcccg cctcctgcct ccgctctact 600
cactggtgtt catctttggt tttgtgggca acatgctggt catcctcatc ctgataaact 660
gcaaaaggct gaagagcatg actgacatct acctgctcaa cctggccatc tctgacctgt 720
ttttccttct tactgtcccc ttctgggctc actatgctgc cgcccagtgg gactttggaa 780
atacaatgtg tcaactcttg acagggctct attttatagg cttcttctct ggaatcttct 840
tcatcatcct cctgacaatc gataggtacc tggctgtcgt ccatgctgtg tttgctttaa 900
aagccaggac ggtcaccttt ggggtggtga caagtgtgat cacttgggtg gtggctgtgt 960
ttgcgtctct cccaggaatc atcttta 987

<210> SEQ ID NO 65
<211> LENGTH: 987
<212> TYPE: DNA
<213> ORGANISM: Artificial Sequence
<220> FEATURE:
<223> OTHER INFORMATION: Synthetic sequence, CCR5 Gene with CRISPR induced deletion.
<220> FEATURE:
<221> NAME/KEY: Deleted Nucleotides
<222> LOCATION: (120)..(460)

<400> SEQUENCE: 65

```
ccacttggag gggtgaggtg agaggattgc ttgagcccgg gatggtccag gctgcagtga     60
gccatgatcg tgccactgca ctccagcctg ggcgacagag tgagaccctg tctcacaaca    120
acaacaacaa caacaaaaag gctgagctgc accatgcttg acccagtttc ttaaaattgt    180
tgtcaaagct tcattcactc catggtgcta tagagcacaa gattttattt ggtgagatgg    240
tgctttcatg aattccccca acagagccaa gctctccatc tagtggacag ggaagctagc    300
agcaaacctt cccttcacta caaaacttca ttgcttggcc aaaaagagag ttaattcaat    360
gtagacatct atgtaggcaa ttaaaaacct attgatgtat aaaacagttt gcattcatgg    420
agggcaacta aatacattct aggactttat aaaagatcac tttttattta tgcacagggt    480
ggaacaagat ggattatcaa gtgtcaagtc caatctatga catcaattat tatacatcgg    540
agccctgcca aaaaatcaat gtgaagcaaa tcgcagcccg cctcctgcct ccgctctact    600
cactggtgtt catctttggt tttgtgggca acatgctggt catcctcatc ctgataaact    660
gcaaaaggct gaagagcatg actgacatct acctgctcaa cctggccatc tctgacctgt    720
tttccttct tactgtcccc ttctgggctc actatgctgc cgcccagtgg gactttggaa     780
atacaatgtg tcaactcttg acagggctct attttatagg cttcttctct ggaatcttct    840
tcatcatcct cctgacaatc gataggtacc tggctgtcgt ccatgctgtg tttgctttaa    900
aagccaggac ggtcaccttt ggggtggtga caagtgtgat cacttgggtg gtggctgtgt    960
ttgcgtctct cccaggaatc atcttta                                        987
```

<210> SEQ ID NO 66
<211> LENGTH: 988
<212> TYPE: DNA
<213> ORGANISM: Artificial Sequence
<220> FEATURE:
<223> OTHER INFORMATION: Synthetic sequence, CCR5 Gene with CRISPR induced deletion.
<220> FEATURE:
<221> NAME/KEY: Deleted Nucleotides
<222> LOCATION: (115)..(382)

<400> SEQUENCE: 66

```
ccacttggag gggtgaggtg agaggattgc ttgagcccgg gatggtccag gctgcagtga     60
gccatgatcg tgccactgca ctccagcctg ggcgacagag tgagaccctg tctcacaaca    120
acaacaacaa caacaaaaag gctgagctgc accatgcttg acccagtttc ttaaaattgt    180
tgtcaaagct tcattcactc catggtgcta tagagcacaa gattttattt ggtgagatgg    240
tgctttcatg aattccccca acagagccaa gctctccatc tagtggacag ggaagctagc    300
agcaaacctt cccttcacta caaaacttca ttgcttggcc aaaaagagag ttaattcaat    360
gtagacatct atgtaggcaa ttaaaaacct attgatgtat aaaacagttt gcattcatgg    420
agggcaacta aatacattct aggactttat aaaagatcac tttttattta tgcacagggt    480
ggaacaagat ggattatcaa gtgtcaagtc caatctatga catcaattat tatacatcgg    540
agccctgcta aaaaaatcaa tgtgaagcaa atcgcagccc gcctcctgcc tccgctctac    600
tcactggtgt tcatctttgg ttttgtgggc aacatgctgg tcatcctcat cctgataaac    660
tgcaaaaggc tgaagagcat gactgacatc tacctgctca acctggccat ctctgacctg    720
tttttccttc ttactgtccc cttctgggct cactatgctg ccgcccagtg ggactttgga    780
aatacaatgt gtcaactctt gacagggctc tattttatag gcttcttctc tggaatcttc    840
ttcatcatcc tcctgacaat cgataggtac ctggctgtcg tccatgctgt gtttgcttta    900
```

aaagccagga cggtcacctt tggggtggtg acaagtgtga tcacttgggt ggtggctgtg 960
tttgcgtctc tcccaggaat catcttta 988

<210> SEQ ID NO 67
<211> LENGTH: 987
<212> TYPE: DNA
<213> ORGANISM: Artificial Sequence
<220> FEATURE:
<223> OTHER INFORMATION: Synthetic sequence, CCR5 Gene with CRISPR
induced deletion.
<220> FEATURE:
<221> NAME/KEY: Deleted Nucleotides
<222> LOCATION: (61)..(404)

<400> SEQUENCE: 67
ccacttggag gggtgaggtg agaggattgc ttgagcccgg gatggtccag gctgcagtga 60
gccatgatcg tgccactgca ctccagcctg ggcgacagag tgagaccctg tctcacaaca 120
acaacaacaa caacaaaaag gctgagctgc accatgcttg acccagtttc ttaaaattgt 180
tgtcaaagct tcattcactc catggtgcta tagagcacaa gattttattt ggtgagatgg 240
tgctttcatg aattccccca acagagccaa gctctccatc tagtggacag ggaagctagc 300
agcaaacctt cccttcacta caaaacttca ttgcttggcc aaaaagagag ttaattcaat 360
gtagacatct atgtaggcaa ttaaaaacct attgatgtat aaaacagttt gcattcatgg 420
agggcaacta aatacattct aggactttat aaaagatcac tttttattta tgcacagggt 480
ggaacaagat ggattatcaa gtgtcaagtc caatctatga catcaattat tatacatcgg 540
agccctgcca aaaaatcaat gtgaagcaaa tcgcagcccg cctcctgcct ccgctctact 600
cactggtgtt catctttggt tttgtgggca acatgctggt catcctcatc ctgataaact 660
gcaaaaggct gaagagcatg actgacatct acctgctcaa cctggccatc tctgacctgt 720
ttttccttct tactgtcccc ttctgggctc actatgctgc cgcccagtgg gactttggaa 780
atacaatgtg tcaactcttg acagggctct attttatagg cttcttctct ggaatcttct 840
tcatcatcct cctgacaatc gataggtacc tggctgtcgt ccatgctgtg tttgctttaa 900
aagccaggac ggtcaccttt ggggtggtga caagtgtgat cacttgggtg gtggctgtgt 960
ttgcgtctct cccaggaatc atcttta 987

<210> SEQ ID NO 68
<211> LENGTH: 2130
<212> TYPE: DNA
<213> ORGANISM: Homo sapiens

<400> SEQUENCE: 68
agggaaaaga ggcttcctgg aggagatggc ttagaaccat agacctgccc tctgcctcat 60
gcctcctcca tcatggagga tggttgtcca gtttctgttt gaaccccacc ccataccttg 120
ccagggctct cactgccaga cacagaatag ggggctccct gggttcaaag tagagctcac 180
ttctgtcccc tgggcttctc ctgactgttc cttgtgtgac ctgttcccac atctggatgg 240
gctgcaggag ccagtgctgt ggggacagaa ggtctggagc tgcccgtgaa gggcagaatg 300
ctgccctcag acccgcttcc tccctgtcct tgtctgtcca aggagaatga ggtctcactg 360
gtggatttcg gactaccctg aggagctggc acctgaggga caaggccccc cacctgccca 420
gctccagcct ctgatgaggg gtgggagaga gctacatgag gttgctaaga aagcctcccc 480
tgaaggagac cacacagtgt gtgaggttgg agtctctagc agcgggttct gtgcccccag 540
ggatagtctg gctgtccagg cactgctctt gatataaaca ccacctccta gttatgaaac 600
catgcccatt ctgcctctct gtatggaaaa gagcatgggg ctggcccgtg gggtggtgtc 660
cactttaggc cctgtgggag atcatgggaa cccacgcagt gggtcatagg ctctctcatt 720
tactactcac atccactctg tgaagaagcg attatgatct ctcctctaga aactcgtaga 780
gtcccatgtc tgccggcttc cagagcctgc actcctccac cttggcttgg ctttgctggg 840
gctagaggag ctaggatgca cagcagctct gtgacccttt gtttgagagg aacaggaaaa 900
ccacccttct ctctggccca ctgtgtcctc ttcctgccct gccatcccct tctgtgaatg 960
ttagacccat gggagcagct ggtcagaggg gaccccggcc tggggcccct aaccctatgt 1020
agcctcagtc ttcccatcag gctctcagct cagcctgagt gttgaggccc cagtggctgc 1080
tctgggggcc tcctgagttt ctcatctgtg cccctccctc cctggcccag gtgaaggtgt 1140
ggttccagaa ccggaggaca aagtacaaac ggcagaagct ggaggaggaa gggcctgagt 1200
ccgagcagaa gaagaagggc tcccatcaca tcaaccggtg gcgcattgcc acgaagcagg 1260
ccaatgggga ggacatcgat gtcacctcca atgactaggg tgggcaacca caaacccacg 1320
agggcagagt gctgcttgct gctggccagg cccctgcgtg ggcccaagct ggactctggc 1380
cactccctgg ccaggctttg gggaggcctg gagtcatggc cccacagggc ttgaagcccg 1440
gggccgccat tgacagaggg acaagcaatg ggctggctga ggcctgggac cacttggcct 1500
tctcctcgga gagcctgcct gcctgggcgg gcccgcccgc caccgcagcc tcccagctgc 1560
tctccgtgtc tccaatctcc cttttgtttt gatgcatttc tgttttaatt tattttccag 1620
gcaccactgt agtttagtga tccccagtgt ccccccttccc tatgggaata ataaaagtct 1680
ctctcttaat gacacgggca tccagctcca gccccagagc ctggggtggt agattccggc 1740
tctgagggcc agtgggggct ggtagagcaa acgcgttcag ggcctgggag cctggggtgg 1800
ggtactggtg gagggggtca agggtaattc attaactcct ctcttttgtt gggggaccct 1860
ggtctctacc tccagctcca cagcaggaga aacaggctag acatagggaa gggccatcct 1920
gtatcttgag ggaggacagg cccaggtctt tcttaacgta ttgagaggtg ggaatcaggc 1980
ccaggtagtt caatgggaga gggagagtgc ttccctctgc ctagagactc tggtggcttc 2040
tccagttgag gagaaaccag aggaaagggg aggattgggg tctgggggag ggaacaccat 2100
tcacaaaggc tgacggttcc agtccgaagt 2130

<210> SEQ ID NO 69
<211> LENGTH: 1730
<212> TYPE: DNA
<213> ORGANISM: Artificial Sequence
<220> FEATURE:
<223> OTHER INFORMATION: Synthetic sequence, EMX1 Gene with CRISPR induced deletion.
<220> FEATURE:
<221> NAME/KEY: Deleted Nucleotides
<222> LOCATION: (163)..(675)
<220> FEATURE:
<221> NAME/KEY: Deleted Nucleotides
<222> LOCATION: (1030)..(1392)

<400> SEQUENCE: 69
gggcttctcc tgactgttcc ttgtgtgacc tgttcccaca tctggatggg ctgcaggagc 60
cagtgctgtg gggacagaag gtctggagct gcccgtgaag ggcagaatgc tgccctcaga 120
cccgcttcct ccctgtcctt gtctgtccaa ggagaatgag gtctcactgg tggatttcgg 180
actaccctga ggagctggca cctgagggac aaggcccccc acctgcccag ctccagcctc 240
tgatgagggg tgggagagag ctacatgagg ttgctaagaa agcctcccct gaaggagacc 300
acacagtgtg tgaggttgga gtctctagca gcgggttctg tgcccccagg gatagtctgg 360
ctgtccaggc actgctcttg atataaacac cacctcctag ttatgaaacc atgcccattc 420
tgcctctctg tatggaaaag agcatggggc tggcccgtgg ggtggtgtcc actttaggcc 480
ctgtgggaga tcatgggaac ccacgcagtg ggtcataggc tctctcattt actactcaca 540
tccactctgt gaagaagcga ttatgatctc tcctctagaa actcgtagag tcccatgtct 600
gccggcttcc agagcctgca ctcctccacc ttggcttggc tttgctgggg ctagaggagc 660
taggatgcac agcagctctg tgaccctttg tttgagagga acaggaaaac cacccttctc 720
tctggcccac tgtgtcctct tcctgccctg ccatcccctt ctgtgaatgt tagacccatg 780
ggagcagctg gtcagagggg accccggcct ggggccccta accctatgta gcctcagtct 840
tcccatcagg ctctcagctc agcctgagtg ttgaggcccc agtggctgct ctgggggcct 900
cctgagtttc tcatctgtgc ccctccctcc ctggcccagg tgaaggtgtg gttccagaac 960
cggaggacaa agtacaaacg gcagaagctg gaggaggaag ggcctgagtc cgagcagaag 1020
aagaagggct cccatcacat caaccggtgg cgcattgcca cgaagcaggc caatggggag 1080
gacatcgatg tcacctccaa tgactagggt gggcaaccac aaacccacga gggcagagtg 1140
ctgcttgctg ctggccaggc ccctgcgtgg gcccaagctg gactctggcc actccctggc 1200
caggctttgg ggaggcctgg agtcatggcc ccacagggct tgaagcccgg ggccgccatt 1260
gacagaggga caagcaatgg gctggctgag gcctgggacc acttggcctt ctcctcggag 1320
agcctgcctg cctgggcggg cccgcccgcc accgcagcct cccagctgct ctccgtgtct 1380
ccaatctccc ttttgttttg atgcatttct gttttaattt attttccagg caccactgta 1440
gtttagtgat ccccagtgtc cccccttccct atgggaataa taaaagtctc tctcttaatg 1500
acacgggcat ccagctccag ccccagagcc tggggtggta gattccggct ctgagggcca 1560
gtgggggctg gtagagcaaa cgcgttcagg gcctgggagc ctggggtggg gtactggtgg 1620
agggggtcaa gggtaattca ttaactcctc tcttttgttg gggggacctg gtctctacct 1680
ccagctccac agcaggagaa acaggctaga catagggaag ggccatcctg 1730

<210> SEQ ID NO 70
<211> LENGTH: 1730
<212> TYPE: DNA
<213> ORGANISM: Artificial Sequence
<220> FEATURE:
<223> OTHER INFORMATION: Synthetic sequence, EMX1 Gene with CRISPR induced deletion.
<220> FEATURE:
<221> NAME/KEY: Deleted Nucleotides
<222> LOCATION: (296)..(989)

<400> SEQUENCE: 70
gggcttctcc tgactgttcc ttgtgtgacc tgttcccaca tctggatggg ctgcaggagc 60
cagtgctgtg ggacagaag gtctggagct gcccgtgaag ggcagaatgc tgccctcaga 120
cccgcttcct ccctgtcctt gtctgtccaa ggagaatgag gtctcactgg tggatttcgg 180
actaccctga ggagctggca cctgagggac aaggcccccc acctgcccag ctccagcctc 240
tgatgagggg tgggagagag ctacatgagg ttgctaagaa agcctcccct gaaggagacc 300
acacagtgtg tgaggttgga gtctctagca gcgggttctg tgcccccagg gatagtctgg 360
ctgtccaggc actgctcttg atataaacac cacctcctag ttatgaaacc atgcccattc 420
tgcctctctg tatggaaaag agcatggggc tggcccgtgg ggtggtgtcc actttaggcc 480
ctgtgggaga tcatgggaac ccacgcagtg ggtcataggc tctctcattt actactcaca 540
tccactctgt gaagaagcga ttatgatctc tcctctagaa actcgtagag tcccatgtct 600
gccggcttcc agagcctgca ctcctccacc ttggcttggc tttgctgggg ctagaggagc 660
taggatgcac agcagctctg tgaccctttg tttgagagga acaggaaaac caccccttctc 720 tctggcccac tgtgtcctct tcctgccctg ccatcccctt ctgtgaatgt tagacccatg 780
ggagcagctg gtcagagggg accccggcct ggggccccta accctatgta gcctcagtct 840
tcccatcagg ctctcagctc agcctgagtg ttgaggcccc agtggctgct ctgggggcct 900
cctgagtttc tcatctgtgc ccctccctcc ctggcccagg tgaaggtgtg gttccagaac 960
cggaggacaa agtacaaacg gcagaagctg gaggaggaag ggcctgagtc cgagcagaag 1020
aagaagggct cccatcacat caaccggtgg cgcattgcca cgaagcaggc caatggggag 1080
gacatcgatg tcacctccaa tgactagggt gggcaaccac aaacccacga gggcagagtg 1140
ctgcttgctg ctggccaggc ccctgcgtgg gcccaagctg gactctggcc actccctggc 1200
caggctttgg ggaggcctgg agtcatggcc ccacagggct tgaagcccgg ggccgccatt 1260
gacagaggga caagcaatgg gctggctgag gcctgggacc acttggcctt ctcctcggag 1320
agcctgcctg cctgggcggg cccgcccgcc accgcagcct cccagctgct ctccgtgtct 1380
ccaatctccc ttttgttttg atgcatttct gttttaattt attttccagg caccactgta 1440
gtttagtgat ccccagtgtc ccccttccct atgggaataa taaaagtctc tctcttaatg 1500
acacgggcat ccagctccag ccccagagcc tggggtggta gattccggct ctgagggcca 1560
gtgggggctg gtagagcaaa cgcgttcagg gcctgggagc ctggggtggg gtactggtgg 1620
agggggtcaa gggtaattca ttaactcctc tcttttgttg ggggaccctg gtctctacct 1680
ccagctccac agcaggagaa acaggctaga catagggaag ggccatcctg 1730

<210> SEQ ID NO 71
<211> LENGTH: 176
<212> TYPE: DNA
<213> ORGANISM: Artificial Sequence
<220> FEATURE:
<223> OTHER INFORMATION: Synthetic sequence, pre-crRNA(LRSR)

<400> SEQUENCE: 71
tggatgtgtt gtttgtgtga tactataaag ttggtagatt gtgactggct taaaaaatca 60
ttaattaata ataggttatg tttagagtgt tccccgcgcc agcggggata aaccgcaggc 120
caatggggag gacatcgatg tcacctcgtg ttccccgcgc cagcggggat aaaccg 176

<210> SEQ ID NO 72
<211> LENGTH: 90
<212> TYPE: DNA
<213> ORGANISM: Artificial Sequence
<220> FEATURE:
<223> OTHER INFORMATION: Synthetic sequence, pre-crRNA(RSR)

<400> SEQUENCE: 72
gtgttccccg cgccagcggg gataaaccgc aggccaatgg ggaggacatc gatgtcacct 60
cgtgttcccc gcgccagcgg ggataaaccg 90

<210> SEQ ID NO 73
<211> LENGTH: 61
<212> TYPE: DNA
<213> ORGANISM: Artificial Sequence
<220> FEATURE:

<223> OTHER INFORMATION: Synthetic sequence, mature crRNA

<400> SEQUENCE: 73
ataaaccgca ggccaatggg gaggacatcg atgtcacctc gtgttccccg cgccagcggg 60
g 61

<210> SEQ ID NO 74
<211> LENGTH: 35
<212> TYPE: DNA
<213> ORGANISM: Homo sapiens

<400> SEQUENCE: 74
aagcaggcca atggggagga catcgatgtc acctc 35

<210> SEQ ID NO 75
<211> LENGTH: 34
<212> TYPE: DNA
<213> ORGANISM: Homo sapiens
<220> FEATURE:
<221> NAME/KEY: Seed
<222> LOCATION: (1)..(8)
<220> FEATURE:
<221> NAME/KEY: Spacer
<222> LOCATION: (9)..(32)

<400> SEQUENCE: 75
tcacatcaac cggtggcgca ttgccacgaa gcag 34

<210> SEQ ID NO 76
<211> LENGTH: 10
<212> TYPE: DNA
<213> ORGANISM: Artificial Sequence
<220> FEATURE:
<223> OTHER INFORMATION: Synthetic sequence, Emx1 deletion mutant

<400> SEQUENCE: 76
ctgccctacc 10

<210> SEQ ID NO 77
<211> LENGTH: 10
<212> TYPE: DNA
<213> ORGANISM: Artificial Sequence
<220> FEATURE:
<223> OTHER INFORMATION: Synthetic sequence, Emx1 deletion mutant

<400> SEQUENCE: 77
gcccacctgg 10

<210> SEQ ID NO 78
<211> LENGTH: 10
<212> TYPE: DNA
<213> ORGANISM: Artificial Sequence
<220> FEATURE:
<223> OTHER INFORMATION: Synthetic sequence, Emx1 deletion mutant

<400> SEQUENCE: 78
gagctgagga 10

<210> SEQ ID NO 79
<211> LENGTH: 10
<212> TYPE: DNA
<213> ORGANISM: Artificial Sequence
<220> FEATURE:
<223> OTHER INFORMATION: Synthetic sequence, Emx1 deletion mutant

<400> SEQUENCE: 79

-continued

```
accctcagct                                                         10


<210> SEQ ID NO 80
<211> LENGTH: 10
<212> TYPE: DNA
<213> ORGANISM: Artificial Sequence
<220> FEATURE:
<223> OTHER INFORMATION: Synthetic sequence,   Emx1 deletion mutant

<400> SEQUENCE: 80

tgaggtctca                                                         10


<210> SEQ ID NO 81
<211> LENGTH: 10
<212> TYPE: DNA
<213> ORGANISM: Artificial Sequence
<220> FEATURE:
<223> OTHER INFORMATION: Synthetic sequence,   Emx1 deletion mutant

<400> SEQUENCE: 81

ggactaggcc                                                         10


<210> SEQ ID NO 82
<211> LENGTH: 10
<212> TYPE: DNA
<213> ORGANISM: Artificial Sequence
<220> FEATURE:
<223> OTHER INFORMATION: Synthetic sequence,   Emx1 deletion mutant

<400> SEQUENCE: 82

ggactaagaa                                                         10


<210> SEQ ID NO 83
<211> LENGTH: 17
<212> TYPE: DNA
<213> ORGANISM: Artificial Sequence
<220> FEATURE:
<223> OTHER INFORMATION: Synthetic sequence,   Emx1 deletion mutant

<400> SEQUENCE: 83

tgatgcaggc caatggg                                                 17
```